United States Patent
Barth et al.

(10) Patent No.: US 8,410,137 B2
(45) Date of Patent: Apr. 2, 2013

(54) THIOPHENE-2-CARBOXAMIDE DERIVATIVES, PREPARATION THEREOF AND THERAPEUTIC USE THEREOF

(75) Inventors: Francis Barth, Paris (FR); Jean-Philippe Ducoux, Paris (FR); Patrick Gueule, Paris (FR); Murielle Rinaldi-Carmona, Paris (FR); Arnaud Rouquette, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/057,043

(22) PCT Filed: Jul. 30, 2009

(86) PCT No.: PCT/FR2009/051540
§ 371 (c)(1), (2), (4) Date: Apr. 8, 2011

(87) PCT Pub. No.: WO2010/012964
PCT Pub. Date: Feb. 4, 2010

(65) Prior Publication Data
US 2011/0183960 A1 Jul. 28, 2011

(30) Foreign Application Priority Data

Aug. 1, 2008 (FR) ...................... 08 04384

(51) Int. Cl.
*A61K 31/445* (2006.01)
*C07D 409/06* (2006.01)
(52) U.S. Cl. ........ 514/326; 546/184; 546/192; 546/207; 546/212; 514/315; 514/317
(58) Field of Classification Search .................. 546/184, 546/192, 207, 212; 514/315, 317, 326
See application file for complete search history.

(56) References Cited

U.S. PATENT DOCUMENTS

| | | | | |
|---|---|---|---|---|
| 7,462,631 | B2 * | 12/2008 | Barth et al. | 514/326 |
| 7,589,120 | B2 * | 9/2009 | Barth et al. | 514/438 |
| 7,674,821 | B2 * | 3/2010 | Barth et al. | 514/438 |
| 7,687,537 | B2 * | 3/2010 | Ducoux et al. | 514/438 |

FOREIGN PATENT DOCUMENTS

FR 2 860 792 4/2005

OTHER PUBLICATIONS

International Search Report dated Mar. 19, 2010.

* cited by examiner

*Primary Examiner* — Golam M M Shameem
(74) *Attorney, Agent, or Firm* — Scully, Scott, Murphy & Presser, P.C.

(57) ABSTRACT

The subject matter of the invention is compounds corresponding to formula (I), in which: $R_1$ and $R_2$, together with the nitrogen atom to which they are attached, constitute a saturated heterocyclic radical containing from 4 to 7 atoms, which is preferably substituted; one of the two substituents $R_3$ and $R_6$ is a group $Y-A-R_9$; $Y$ is an oxygen atom or an $-S(O)_n-$, or $-OSO_2$ group; $A$ is an unsubstituted ($C_1-C_4$) alkylene group; $R_9$ is an $-OR_{19}$, $-CH_3$, $-NR_{19}R_{20}$, $-CONR_{19}R_{20}$, $-NR_{15}COR_{19}$, $-S(O)_nR_{21}$, or $-NR_{13}SO_2R_{21}$ group; $-R_{10}$ is a hydrogen atom or a ($C_1-C_4$) alkyl group. The present invention also relates to the methods of preparation and the therapeutic uses of the compounds of formula (I).

(I)

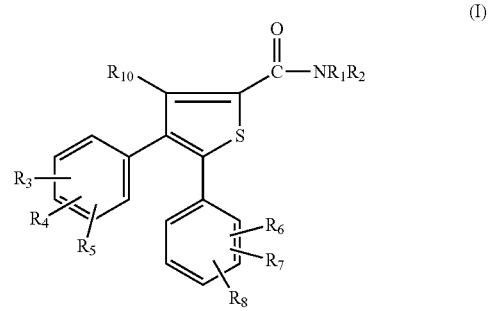

12 Claims, No Drawings

THIOPHENE-2-CARBOXAMIDE DERIVATIVES, PREPARATION THEREOF AND THERAPEUTIC USE THEREOF

A subject-matter of the present invention is 4,5-diarylthiophene-2-carboxamide derivatives, their preparation and their therapeutic application.

Diphenylpyrazole derivatives exhibiting an affinity for $CB_1$, cannabinoid receptors have been described, in particular in U.S. Pat. No. 5,624,941, EP 0 576 357, EP 0 656 354 and EP 1 150 961.

5,6-Diphenyl-2-pyrazinecarboxamide derivatives are described in International Application WO 03/051850 as $CB_1$ receptor antagonists.

1,2-Diphenyl-4-imidazolecarboxamide derivatives are described in International Application WO 03/027076 as agonists of $CB_1$ receptors, partial agonists or antagonists.

4,5-Diarylthiophene derivatives having analgesic properties are described in International Application WO 91/19708.

Other 4,5-diarylthiophene derivatives are described in International Application WO 2005/035488 as $CB_1$ receptor antagonists.

Novel 4,5-diarylthiophene-2-carboxamide derivatives carrying a specific substituent on one of the aryl groups have now been found which have antagonist properties for $CB_1$ cannabinoid receptors at the central level and at the peripheral level.

In particular, these novel derivatives have antagonist properties for peripheral $CB_1$ and exhibit a low penetration in the brain.

Thus, a subject-matter of the present invention is compounds corresponding to the formula (I):

(I)

in which:

$R_1$ and $R_2$, together with the nitrogen atom to which they are bonded, form:

either a saturated heterocyclic radical of 5 to 7 atoms comprising two nitrogen atoms which is unsubstituted or substituted by a phenyl, benzyl, benzodioxolyl, benzodioxolylmethyl, tetrahydrofuranylcarbonyl, —$COR_{11}$ and/or —$CH_2COR_{11}$ group, the phenyl group being itself unsubstituted or substituted one or more times by a substituent each independently chosen from a halogen atom or a ($C_1$-$C_4$)alkyl, trifluoromethyl, hydroxyl, ($C_1$-$C_4$)alkoxy and/or cyano group;

or a saturated heterocyclic radical of 4 to 7 atoms comprising a nitrogen atom which is unsubstituted or substituted once or twice by a substituent each independently chosen from:

a cyano, —$COR_{11}$, —$CH_2NHR_{12}$, —($C_3$-$C_7$)cycloalkyl, —$CH_2COR_{11}$, —$NR_{12}R_{13}$, —$NHCOR_{14}$, —$SO_2R_{14}$ and/or —$SO_2NR_{12}R_{13}$ group;

and/or a phenyl, benzyl or pyridinyl group; the said groups being unsubstituted or substituted one or more times by a substituent each independently chosen from a halogen atom or a ($C_1$-$C_4$)alkyl, trifluoromethyl, hydroxyl, ($C_1$-$C_4$)alkoxy and/or cyano group;

and/or a piperidin-1-yl, pyrrolidin-1-yl or azetidin-1-yl group, the said groups being unsubstituted or substituted one or more times by a substituent each independently chosen from a fluorine atom or a ($C_1$-$C_4$)alkyl, ($C_1$-$C_4$)alkoxy, hydroxyl, trifluoromethyl and/or $OCF_3$ group;

and/or a phenylamino or benzylamino group, the said groups being unsubstituted or substituted one or more times by a substituent each independently chosen from a halogen atom or a ($C_1$-$C_4$)alkyl, trifluoromethyl, hydroxyl, ($C_1$-$C_4$)alkoxy and/or cyano group;

and/or an amino($C_1$-$C_6$)alkyl group which is unsubstituted or substituted one or more times by a substituent each independently chosen from a halogen atom or a hydroxyl, ($C_1$-$C_4$)alkoxy, ($C_3$-$C_7$)cycloalkyl and/or cyano group;

and/or an amino($C_3$-$C_7$)cycloalkyl group which is unsubstituted or substituted one or more times by a substituent each independently chosen from a halogen atom or a hydroxyl, ($C_1$-$C_4$)alkyl, ($C_1$-$C_4$)alkoxy and/or cyano group, the said ($C_1$-$C_4$)alkyl group being unsubstituted or substituted one or more times by a fluorine atom;

$R_3$, $R_4$, $R_5$, $R_6$, $R_7$ and $R_8$ each independently represent a hydrogen atom, a halogen atom, a —CN, —$S(O)_nR_{14}$, —$OSO_2R_{14}$ or ($C_1$-$C_6$)alkyl group and/or a ($C_1$-$C_6$) alkoxy group, the said groups being unsubstituted or substituted one or more times by a fluorine atom, provided that one of the two substituents $R_3$ and $R_6$ represents a Y-A-$R_9$ group;

Y represents an oxygen atom or an —$S(O)_n$— or —$OSO_2$— group;

A represents a ($C_1$-$C_4$)alkylene group which is unsubstituted or substituted one or more times by a ($C_1$-$C_3$)alkyl group and/or by a fluorine atom;

$R_9$ represents an —$OR_{19}$, —CN, —$CH_3$, —$CF_3$, —$NR_{19}R_{20}$, —$CO_2R_{19}$, —$CONR_{19}R_{20}$, —$NR_5COR_{19}$, —$CONHNH_2$, —CONHOH, —$CONHSO_2R_2$, —$S(O)_nR_{21}$, —$SO_2NR_{19}R_{20}$, —$NR_{18}SO_2R_{21}$ or —$NR_{15}SO_2NR_{19}R_{20}$ group;

$R_{10}$ represents a hydrogen atom or a ($C_1$-$C_4$)alkyl group and preferably a hydrogen atom;

$R_{11}$ represents:

a ($C_1$-$C_4$)alkyl, phenyl, benzyl, ($C_1$-$C_4$)alkoxy or ($C_1$-$C_3$)alkylene-O—($C_1$-$C_3$)alkyl group, the said groups being unsubstituted or substituted by a substituent each independently chosen from a ($C_1$-$C_4$)alkoxy group and/or a hydroxyl group and/or by one or more fluorine atoms;

and/or an —$NR_{16}R_{17}$ group;

$R_{12}$ and $R_{13}$ each independently represent a hydrogen atom or a ($C_1$-$C_6$)alkyl group optionally substituted one or more times by a substituent each independently chosen from a fluorine atom, an —OH group and/or an —OR$_{14}$ group;

or R$_{12}$ and R$_{13}$, together with the nitrogen atom to which they are bonded, form a 4- to 7-membered heterocyclic radical which can comprise a second heteroatom chosen from a nitrogen, oxygen or sulphur atom;

n represents 0, 1 or 2;

n' represents 0, 1 or 2;

R$_{14}$ represents a (C$_1$-C$_4$)alkyl group which is unsubstituted or substituted one or more times by a fluorine atom;

R$_{15}$ represents a hydrogen atom or a (C$_1$-C$_4$)alkyl group;

R$_{16}$ and R$_{17}$ each independently represent:
  a hydrogen atom;
  and/or a benzyl group which is unsubstituted or substituted one or more times by a substituent each independently chosen from a halogen atom or a (C$_1$-C$_4$) alkyl, trifluoromethyl, hydroxyl, (C$_1$-C$_4$)alkoxy and/or cyano group;
  and/or a (C$_1$-C$_6$)alkyl group optionally substituted one or more times by a substituent each independently chosen from a halogen atom or an —OH and/or —OR$_{14}$ group;

R$_{18}$ represents a hydrogen atom or a (C$_1$-C$_4$)alkyl group which is unsubstituted or substituted one or more times by a fluorine atom;

R$_{19}$ and R$_{20}$ each independently represent a hydrogen atom or a (C$_1$-C$_6$)alkyl group optionally substituted one or more times by a substituent each independently chosen from a fluorine atom, an —OH group and/or an —OR$_{14}$ group;

or R$_{19}$ and R$_{20}$, together with the nitrogen atom to which they are bonded, form a 4- to 7-membered heterocyclic radical which can comprise a second heteroatom chosen from a nitrogen, oxygen or sulphur atom;

R$_{21}$ represents a (C$_1$-C$_4$)alkyl group which is unsubstituted or substituted one or more times by a fluorine atom;

in the form of bases (=corresponding to the free forms of the compounds) and their pharmaceutically acceptable salts or salts acceptable in the purification and/or isolation of the said compounds of formula (I).

The compounds of formula (I) can comprise one or more asymmetric carbon atoms. They can thus exist in the form of enantiomers or diastereoisomers. These enantiomers, diastereoisomers and their mixtures, including the racemic mixtures, come within the invention.

The compounds of formula (I) can exist in the form of bases (that is to say, such as in their free forms), of addition salts with acids or of addition salts with bases. These salts are advantageously prepared with pharmaceutically acceptable salts; the salts of other acids, for example of use in the purification or isolation of the compounds of formula (I), also come within the invention.

Alkyl group is understood to mean a linear or branched carbon-comprising radical, such as, in particular: methyl, ethyl, propyl, isopropyl, butyl, isobutyl, tert-butyl, n-pentyl, isopentyl, n-hexyl or isohexyl. The methyl group is preferred for a (C$_1$-C$_4$)alkyl and for a (C$_1$-C$_6$)alkyl.

Aminoalkyl group is understood to mean an amino group bonded to a linear or branched carbon-comprising radical, such as, for example: methyl, ethyl, propyl, isopropyl, butyl, isobutyl, tert-butyl, n-pentyl, isopentyl, n-hexyl, isohexyl, heptyl or isoheptyl.

Alkylene group is understood to mean a linear divalent carbon-comprising radical, such as —(CH$_2$)—, —(CH$_2$)$_2$—, —(CH$_2$)$_3$—, —(CH$_2$)$_4$— or —(CH$_2$)$_5$—.

(C$_1$-C$_4$)alkoxy and (C$_1$-C$_6$)alkoxy are understood to mean respectively an oxygen atom bonded to a linear or branched carbon-comprising radical of one to four carbon atoms and of one to six carbon atoms, such as the methoxy, ethoxy, propoxy, isopropoxy, butoxy, sec-butoxy, tert-butoxy, pentoxy or hexyloxy radical, the methoxy group being preferred.

Halogen atom is understood to mean a fluorine, chlorine, bromine or iodine atom, fluorine, chlorine or bromine atoms being preferred.

Cycloalkyl group is understood to mean a cyclopropyl, cyclobutyl, cyclopentyl, cyclohexyl or cycloheptyl carbon-comprising radical.

Aminocycloalkyl group is understood to mean an amino group bonded to a cyclic carbon-comprising radical, such as, for example: cyclopropyl, cyclobutyl, cyclopentyl, cyclohexyl or cycloheptyl.

Saturated 4- to 7-membered heterocyclic radical comprising 1 or 2 nitrogen atoms is understood to mean in particular radicals such as azetidin-1-yl, pyrrolidin-1-yl, piperidin-1-yl, homopiperidin-1-yl, imidazolin-1-yl, piperazin-1-yl and 1,4-diazepan-1-yl.

According to the present invention, the following are distinguished:
  the compounds of formula (IA) in which Y represents an oxygen atom;
  the compounds of formula (IB) in which Y represents an —S(O)$_{n'}$— group;
  the compounds of formula (IC) in which Y represents an —O(SO$_2$)— group; the other substituents being as defined for the compounds of formula (I).

Within the compounds of formulae (I), (IA), (IB) and (IC), the following in particular are distinguished:
  the compounds in which the R$_3$ substituent represents a Y-A-R$_9$ group and the R$_6$ substituent represents a hydrogen atom, a halogen atom, a —CN, —S(O)$_n$R$_{14}$ or —OSO$_2$R$_{14}$ group, a (C$_1$-C$_6$)alkyl group or a (C$_1$-C$_6$) alkoxy group, the said groups being unsubstituted or substituted by one or more fluorine atoms;
  and the compounds in which the R$_6$ substituent represents a Y-A-R$_9$ group and the R$_6$ substituent represents a hydrogen atom, a halogen atom, a —CN, —S(O)$_n$R$_{14}$ or —OSO$_2$R$_{14}$ group, a (C$_1$-C$_6$)alkyl group or a (C$_1$-C$_6$) alkoxy group, the said groups being unsubstituted or substituted by one or more fluorine atoms;

the other substituents being as defined above for the compounds of formula (I).

Preferably, for the compounds in which the R$_3$ substituent represents a Y-A-R$_9$ group, R$_4$, R$_5$, R$_6$, R$_7$ and R$_8$ each independently represent a hydrogen atom, a halogen atom, a —CN group and/or a (C$_1$-C$_6$)alkyl group, the said group being unsubstituted or substituted one or more times by a fluorine atom.

Preferably, for the compounds in which the $R_6$ substituent represents a Y-A-$R_9$ group, $R_3$, $R_4$, $R_5$, $R_7$ and $R_8$ each independently represent a hydrogen atom, a halogen atom, a —CN group and/or a ($C_1$-$C_6$)alkyl group, the said group being unsubstituted or substituted one or more times by a fluorine atom.

For both these preferred forms, the other substituents are as defined above for the compounds of formula (I).

For the compounds in which the $R_3$ substituent represents a Y-A-$R_9$ group, the $R_4$ substituent and/or the $R_5$ substituent preferably correspond to a hydrogen atom. More preferably, $R_3$ is in the 4 position on the phenyl. For this alternative form of the compounds of formula (I) according to the invention, it is preferable in addition for $R_6$ to correspond to a hydrogen or halogen atom, such as chlorine or fluorine, for $R_7$ to correspond to a halogen atom, preferably a chlorine atom, and for $R_8$ to correspond to a hydrogen atom.

According to the present invention, preference is given to the compounds of formula (I) in which:
   A represents an unsubstituted ($C_1$-$C_4$)alkylene group;
   $R_9$ represents an —$OR_{19}$, —$CH_3$, —$CF_3$, —$NR_{19}R_{20}$, —$CONR_{19}R_{20}$, —$NR_{15}COR_{19}$, —$S(O)_nR_{21}$ or —$NR_{18}SO_2R_{21}$ group;
   and the other substituents are as defined above for the compounds of formula (I).

In particular for Y, preference is given to an oxygen atom or a sulphur atom.

In particular for $R_9$, preference is given to an —$OR_{19}$, —$NR_{19}R_{20}$, —$CONR_{19}R_{20}$, —$S(O)_nR_{21}$ or —$NR_{19}SO_2R_{21}$ group.

According to the present invention, preference is given to the compounds of formula (I) in which:
   $R_1$ and $R_2$, together with the nitrogen atom to which they are bonded, form a homopiperidin-1-yl, piperidin-1-yl, pyrrolidin-1-yl or azetidin-1-yl radical, the said radicals being substituted once or twice by a substituent each independently chosen from:
      a cyano, —$COR_{11}$, —$NR_{12}R_{13}$, —$NHCOR_{14}$, —$CH_2COR_{11}$, —$SO_2R_{14}$ and/or —$SO_2NR_{12}R_{13}$ group;
      and/or a phenyl, benzyl or pyridinyl group; the said groups being unsubstituted or substituted one or more times by a substituent each independently chosen from a halogen atom or a ($C_1$-$C_4$)alkyl, trifluoromethyl, hydroxyl, ($C_1$-$C_4$)alkoxy and/or cyano group;
      and/or a piperidin-1-yl, pyrrolidin-1-yl or azetidin-1-yl group, the said groups being unsubstituted or substituted one or more times by a substituent each independently chosen from a fluorine atom or a ($C_1$-$C_4$)alkyl, ($C_1$-$C_4$)alkoxy, hydroxyl, trifluoromethyl and/or $OCF_3$ group;
      and/or a phenylamino or benzylamino group, the said groups being unsubstituted or substituted one or more times by a substituent each independently chosen from a halogen atom or a ($C_1$-$C_4$)alkyl, trifluoromethyl, hydroxyl, ($C_1$-$C_4$)alkoxy and/or cyano group;
      and/or an amino($C_1$-$C_6$)alkyl group which is unsubstituted or substituted one or more times by a substituent each independently chosen from a halogen atom or a hydroxyl, ($C_1$-$C_4$)alkoxy and/or cyano group;
      and/or an amino($C_3$-$C_7$)cycloalkyl group which is unsubstituted or substituted one or more times by a substituent each independently chosen from a halogen atom or a hydroxyl, ($C_1$-$C_4$)alkyl, ($C_1$-$C_4$)alkoxy and/or cyano group, the said ($C_1$-$C_4$)alkyl group being unsubstituted or substituted one or more times by a fluorine atom;
   the other substituents are as defined for the compounds of formula (I).

In particular, preference is given to the compounds of formula (I) in which:
   $R_1$ and $R_2$, together with the nitrogen atom to which they are bonded, form a homopiperidin-1-yl, piperidin-1-yl, pyrrolidin-1-yl or azetidin-1-yl radical, the said radical being gem-disubstituted:
      the first substituent of the said radical being chosen from a cyano, —$COR_{11}$, —$NHCOR_{14}$ or —$SO_2R_{14}$ group;
      the second substituent of the said radical being chosen from:
         $NR_{12}R_{13}$;
         and/or a phenyl group, the said group being unsubstituted or substituted one or more times by a substituent each independently chosen from a halogen atom or a ($C_1$-$C_4$)alkyl, trifluoromethyl, hydroxyl, ($C_1$-$C_4$)alkoxy and/or cyano group;
         and/or a piperidin-1-yl group, the said group being unsubstituted or substituted one or more times by a substituent each independently chosen from a fluorine atom or a ($C_1$-$C_4$)alkyl, ($C_1$-$C_4$)alkoxy, hydroxyl, trifluoromethyl and/or $OCF_3$ group;
         and/or a benzylamino group, the said group being unsubstituted or substituted one or more times by a substituent each independently chosen from a halogen atom or a ($C_1$-$C_4$)alkyl, trifluoromethyl, hydroxyl, ($C_1$-$C_4$)alkoxy and/or cyano group;
   the other substituents are as defined for the compounds of formula (I).

More particularly, preference is given to the compounds of formula (I) in which $R_1$ and $R_2$, together with the nitrogen atom to which they are bonded, form a piperidin-1-yl or azetidin-1-yl radical. In this case:
   the first substituent of the piperidin-1-yl or azetidin-1-yl radical is preferably —$COR_{11}$;
   and the second substituent of the piperidin-1-yl or azetidin-1-yl radical is preferably chosen from —$NR_{12}R_{13}$, a phenyl group, a benzylamino group or a piperidin-1-yl group, the said piperidin-1-yl group being unsubstituted or substituted one or more times by a substituent each independently chosen from a fluorine atom or a ($C_1$-$C_4$)alkyl, ($C_1$-$C_4$)alkoxy, hydroxyl, trifluoromethyl and/or $OCF_3$ group;
   the other substituents are as defined for the compounds of formula (I).

Mention may in particular be made, among the compounds according to the invention, of the compounds below, as is and also their salts:

| IUPAC Name | Chemical Structure |
| --- | --- |
| 1-({4-(2,4-dichlorophenyl)-5-[4-(3-hydroxypropoxy)phenyl]-2-thienyl}carbonyl)-4-phenylpiperidine-4-carboxamide | 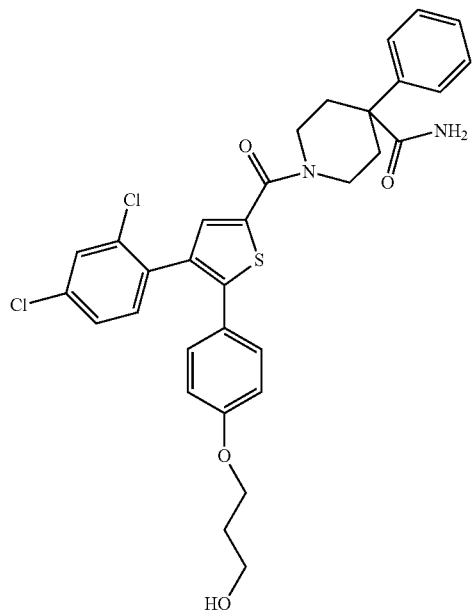 [SMILES: NC(=O)C1(c2ccccc2)CCN(C(=O)c2cc(-c3ccc(Cl)cc3Cl)c(-c3ccc(OCCCO)cc3)s2)CC1] |
| 1-({5-[4-(3-aminopropoxy)phenyl]-4-(2,4-dichlorophenyl)-2-thienyl}carbonyl)-4-phenylpiperidine-4-carboxamide | 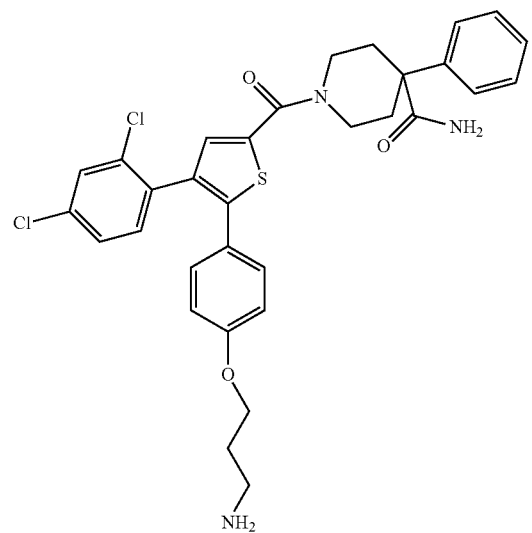 [SMILES: NCCCOc1ccc(-c2sc(C(=O)N3CCC(C(N)=O)(c4ccccc4)CC3)cc2-c2ccc(Cl)cc2Cl)cc1] |

-continued
| IUPAC Name | Chemical Structure |
|---|---|
| 1-{[4-(2,4-dichlorophenyl)-5-(4-{3-[(methylsulphonyl)amino]propoxy}phenyl)-2-thienyl]carbonyl}-4-phenylpiperidine-4-carboxamide | 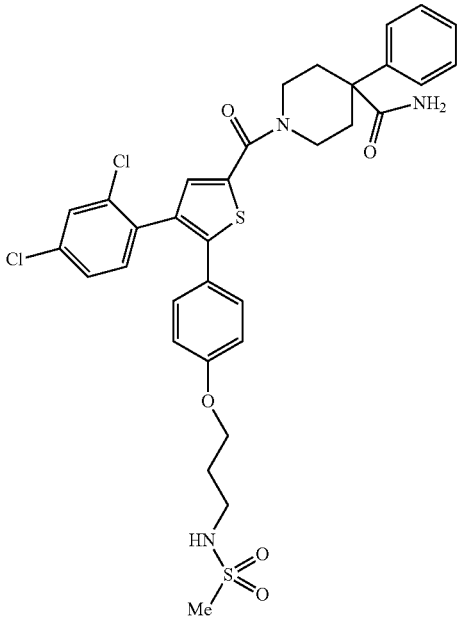 [SMILES: CS(=O)(=O)NCCCOc1ccc(-c2sc(C(=O)N3CCC(C(N)=O)(c4ccccc4)CC3)cc2-c2ccc(Cl)cc2Cl)cc1] |
| 1-{[4-(2,4-dichlorophenyl)-5-{4-[3-(methylthio)propoxy]phenyl}-2-thienyl]carbonyl}-4-phenylpiperidine-4-carboxamide | 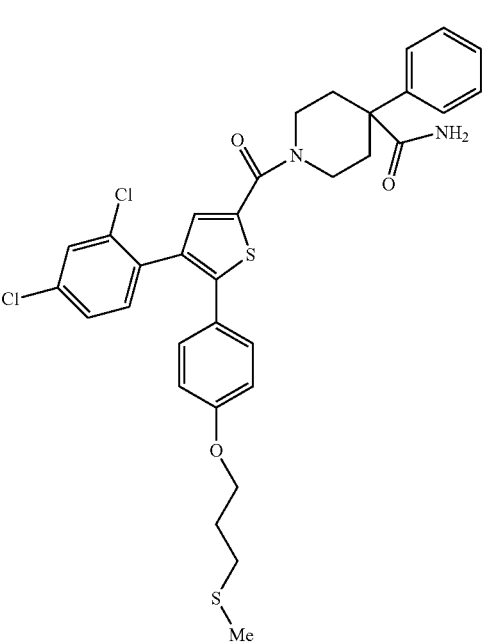 [SMILES: CSCCCOc1ccc(-c2sc(C(=O)N3CCC(C(N)=O)(c4ccccc4)CC3)cc2-c2ccc(Cl)cc2Cl)cc1] |

-continued

| IUPAC Name | Chemical Structure |
|---|---|
| 1-{[4-(2,4-dichlorophenyl)-5-{4-[3-(methylsulphonyl)propoxy]phenyl}-2-thienyl]carbonyl}-4-phenylpiperidine-4-carboxamide | 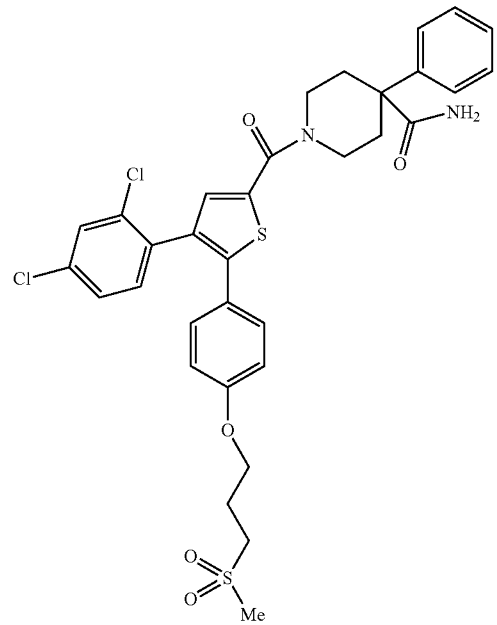 [SMILES: CS(=O)(=O)CCCOc1ccc(-c2sc(C(=O)N3CCC(C(N)=O)(c4ccccc4)CC3)cc2-c2ccc(Cl)cc2Cl)cc1] |
| 1-({4-(2,4-dichlorophenyl)-5-[4-(2-hydroxyethoxy)phenyl]-2-thienyl}carbonyl)-4-phenylpiperidine-4-carboxamide | 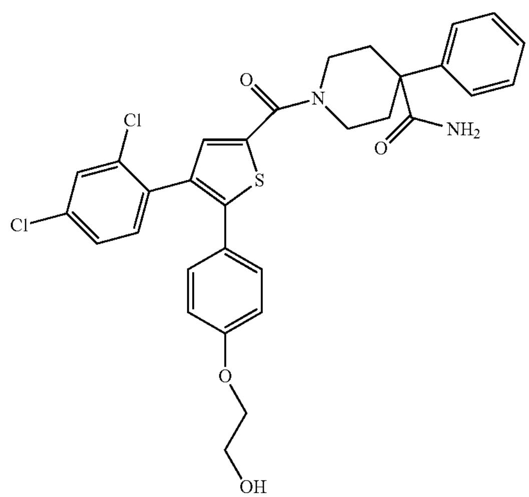 [SMILES: NC(=O)C1(c2ccccc2)CCN(C(=O)c2cc(-c3ccc(Cl)cc3Cl)c(-c3ccc(OCCO)cc3)s2)CC1] |
| 1'-({4-(2,4-dichlorophenyl)-5-[4-(3-hydroxypropoxy)phenyl]-2-thienyl}carbonyl)-4,4-difluoro-1,4'-bipiperidine-4'-carboxamide | 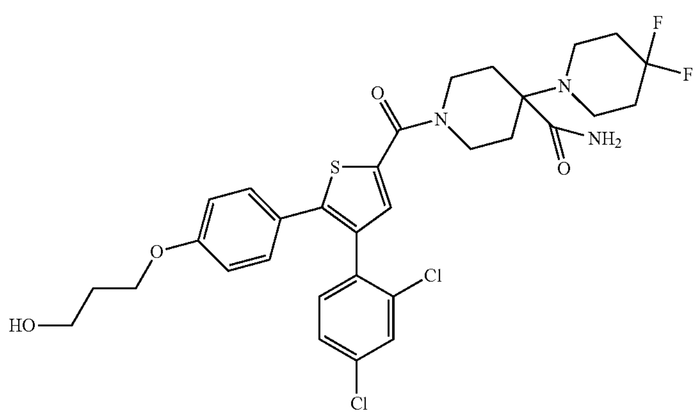 [SMILES: NC(=O)C1(N2CCC(F)(F)CC2)CCN(C(=O)c2cc(-c3ccc(Cl)cc3Cl)c(-c3ccc(OCCCO)cc3)s2)CC1] |

-continued

| IUPAC Name | Chemical Structure |
| --- | --- |
| 1-({5-(2,4-dichlorophenyl)-4-[4-(3-hydroxypropoxy)phenyl]-2-thienyl}carbonyl)-4-phenylpiperidine-4-carboxamide | 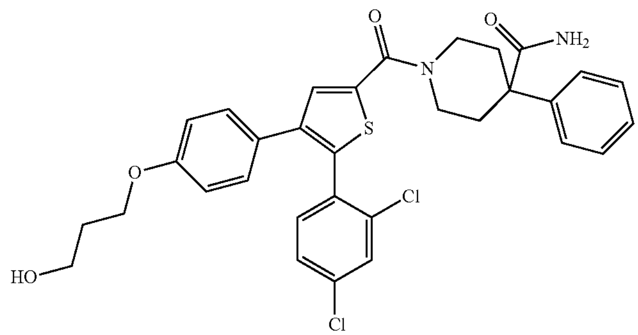 [SMILES: NC(=O)C1(c2ccccc2)CCN(C(=O)c2cc(-c3ccc(OCCCO)cc3)c(-c3ccc(Cl)cc3Cl)s2)CC1] |
| 1-{[5-(2,4-dichlorophenyl)-4-(4-{3-[(methylsulphonyl)amino]propoxy}phenyl)-2-thienyl]carbonyl}-4-phenylpiperidine-4-carboxamide | 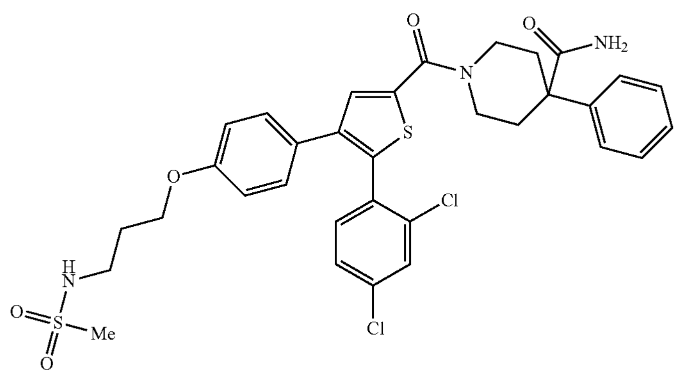 [SMILES: CS(=O)(=O)NCCCOc1ccc(-c2cc(C(=O)N3CCC(C(N)=O)(c4ccccc4)CC3)sc2-c2ccc(Cl)cc2Cl)cc1] |
| 1-({5-(2,4-dichlorophenyl)-4-[4-(3-{pyrrolidin-1-yl}propoxy)phenyl]-2-thienyl}carbonyl)-4-phenylpiperidine-4-carboxamide | 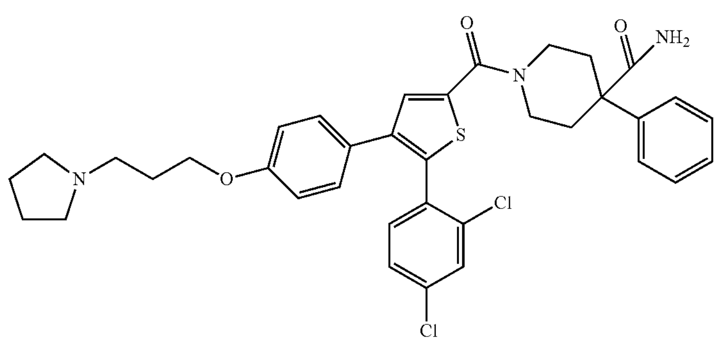 [SMILES: NC(=O)C1(c2ccccc2)CCN(C(=O)c2cc(-c3ccc(OCCCN4CCCC4)cc3)c(-c3ccc(Cl)cc3Cl)s2)CC1] |
| 1-{[5-(2,4-dichlorophenyl)-4-{4-[(4-hydroxybutyl)thio]phenyl}-2-thienyl]carbonyl}-4-phenylpiperidine-4-carboxamide | 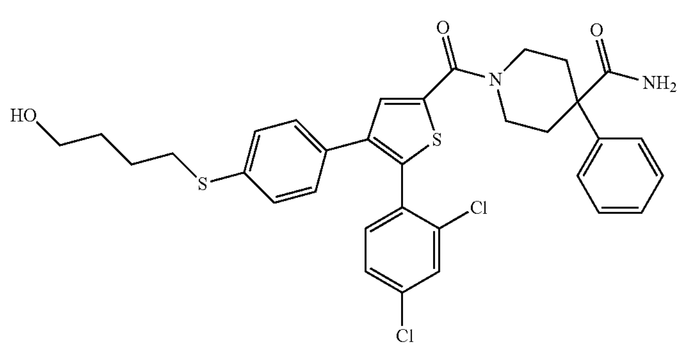 [SMILES: NC(=O)C1(c2ccccc2)CCN(C(=O)c2cc(-c3ccc(SCCCCO)cc3)c(-c3ccc(Cl)cc3Cl)s2)CC1] |

-continued

| IUPAC Name | Chemical Structure |
|---|---|
| 1-{[5-(2,4-dichlorophenyl)-4-{4-[(4-hydroxybutyl)sulphinyl]phenyl}-2-thienyl]carbonyl}-4-phenylpiperidine-4-carboxamide | 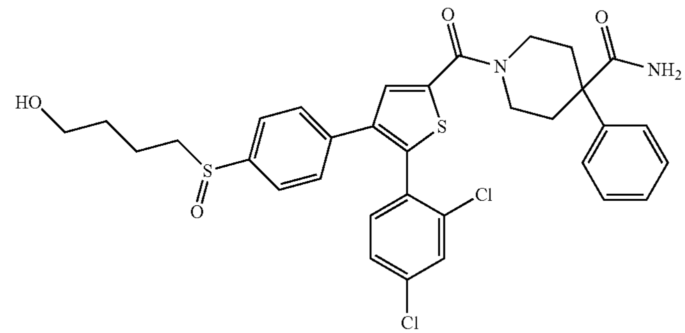 [SMILES: NC(=O)C1(c2ccccc2)CCN(C(=O)c2cc(-c3ccc(S(=O)CCCCO)cc3)c(-c3ccc(Cl)cc3Cl)s2)CC1] |
| 1-{[5-(2,4-dichlorophenyl)-4-{4-[(4-hydroxybutyl)sulphonyl]phenyl}-2-thienyl]carbonyl}-4-phenylpiperidine-4-carboxamide | 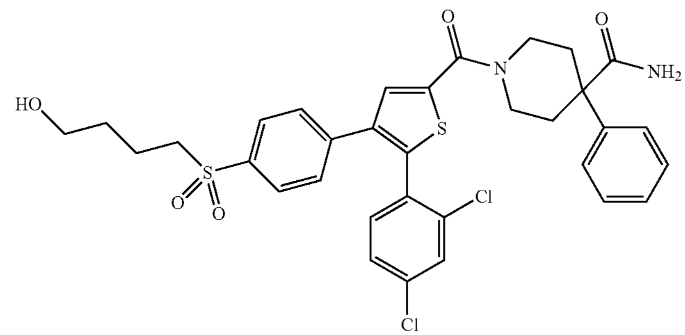 [SMILES: NC(=O)C1(c2ccccc2)CCN(C(=O)c2cc(-c3ccc(S(=O)(=O)CCCCO)cc3)c(-c3ccc(Cl)cc3Cl)s2)CC1] |
| 4-{5-[(4-carbamoyl-4-phenylpiperidin-1-yl)carbonyl]-2-(2-chlorophenyl)thien-3-yl}phenyl propane-1-sulphonate | 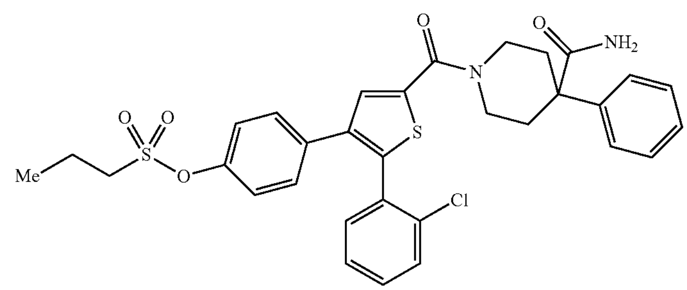 [SMILES: CCCS(=O)(=O)Oc1ccc(-c2cc(C(=O)N3CCC(C(N)=O)(c4ccccc4)CC3)sc2-c2ccccc2Cl)cc1] |
| 4-{5-[(4-carbamoyl-4-phenylpiperidin-1-yl)carbonyl]-2-(2-chlorophenyl)thien-3-yl}phenyl 3,3,3-trifluoropropane-1-sulphonate | 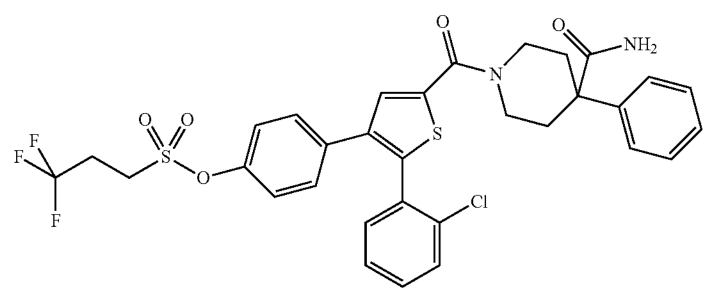 [SMILES: NC(=O)C1(c2ccccc2)CCN(C(=O)c2cc(-c3ccc(OS(=O)(=O)CCC(F)(F)F)cc3)c(-c3ccccc3Cl)s2)CC1] |
| 1-{[5-(2,4-dichlorophenyl)-4-(4-[(4,4,4-trifluorobutyl)thio]phenyl}-2-thienyl]carbonyl}-4-phenylpiperidine-4-carboxamide | 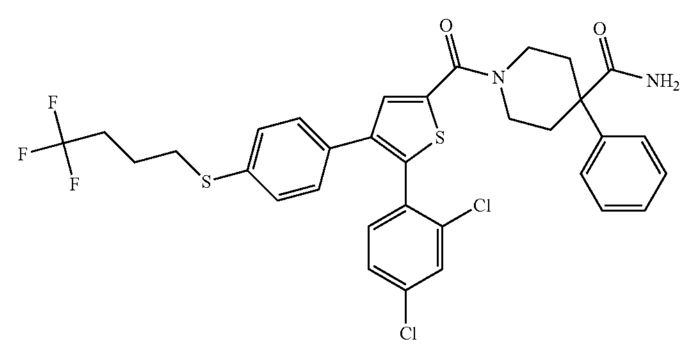 [SMILES: NC(=O)C1(c2ccccc2)CCN(C(=O)c2cc(-c3ccc(SCCCC(F)(F)F)cc3)c(-c3ccc(Cl)cc3Cl)s2)CC1] |

-continued

| IUPAC Name | Chemical Structure |
|---|---|
| 1-{[5-(2,4-dichlorophenyl)-4-{4-[(4,4,4-trifluorobutyl)sulphonyl]phenyl}-2-thienyl]carbonyl}-4-phenylpiperidine-4-carboxamide | |
| 1-({5-(2-chloro-4-fluorophenyl)-4-[4-(3-hydroxypropoxy)phenyl]-2-thienyl}carbonyl)-4-phenylpiperidine-4-carboxamide | 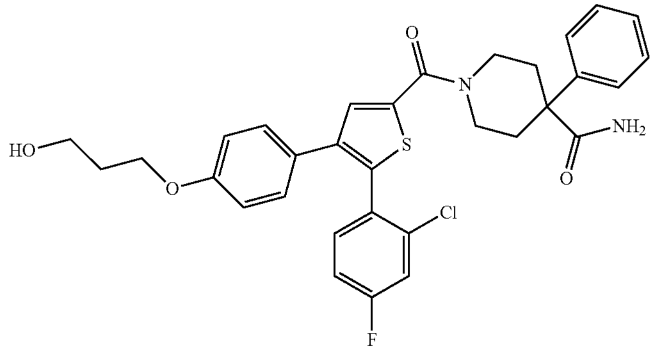 [SMILES: NC(=O)C1(c2ccccc2)CCN(C(=O)c2cc(-c3ccc(OCCCO)cc3)c(-c3ccc(F)cc3Cl)s2)CC1] |
| 1'-({5-(2-chloro-4-fluorophenyl)-4-[4-(3-hydroxypropoxy)phenyl]-2-thienyl}carbonyl)-4,4-difluoro-1,4'-bipiperidine-4'-carboxamide | 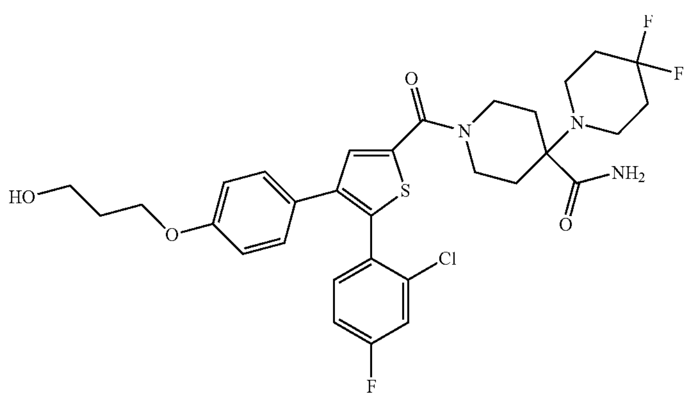 [SMILES: NC(=O)C1(N2CCC(F)(F)CC2)CCN(C(=O)c2cc(-c3ccc(OCCCO)cc3)c(-c3ccc(F)cc3Cl)s2)CC1] |
| 1-({5-(2-chloro-4-fluorophenyl)-4-[4-(3-hydroxypropoxy)phenyl]-2-thienyl}carbonyl)-4-[(3,3,3-trifluoropropyl)amino]piperidine-4-carboxamide | 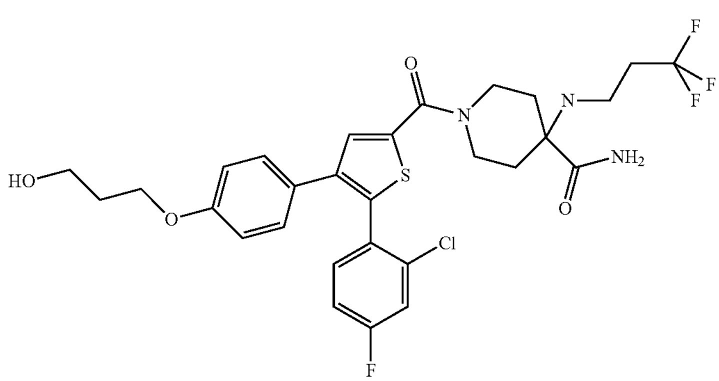 [SMILES: NC(=O)C1(NCCC(F)(F)F)CCN(C(=O)c2cc(-c3ccc(OCCCO)cc3)c(-c3ccc(F)cc3Cl)s2)CC1] |

| IUPAC Name | Chemical Structure |
|---|---|
| 1-{[5-(2-chloro-4-fluorophenyl)-4-{4-[3-(methylthio)propoxy]phenyl}-2-thienyl]carbonyl}-4-phenylpiperidine-4-carboxamide | 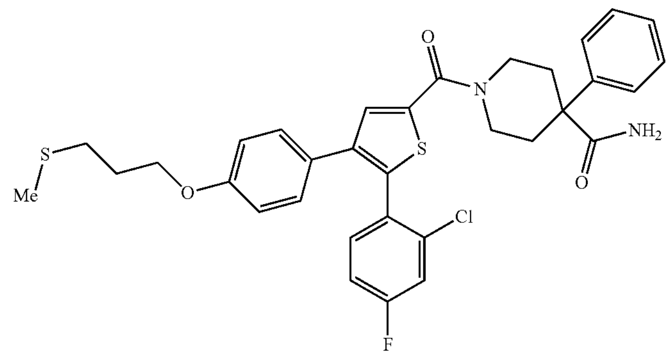 [SMILES: CSCCCOc1ccc(-c2cc(C(=O)N3CCC(C(N)=O)(c4ccccc4)CC3)sc2-c2ccc(F)cc2Cl)cc1] |
| 1-{[5-(2-chloro-4-fluorophenyl)-4-{4-[3-(methylsulphonyl)propoxy]phenyl}-2-thienyl]carbonyl}-4-phenylpiperidine-4-carboxamide | 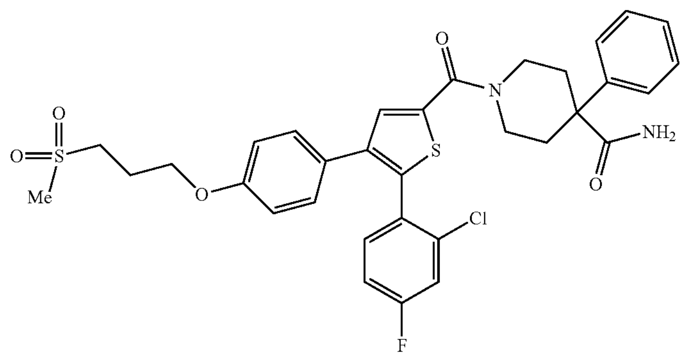 [SMILES: CS(=O)(=O)CCCOc1ccc(-c2cc(C(=O)N3CCC(C(N)=O)(c4ccccc4)CC3)sc2-c2ccc(F)cc2Cl)cc1] |
| 1'-{[5-(2-chloro-4-fluorophenyl)-4-{4-[3-(methylthio)propoxy]phenyl}-2-thienyl]carbonyl}-4,4-difluoro-1,4'-bipiperidine-4'-carboxamide | 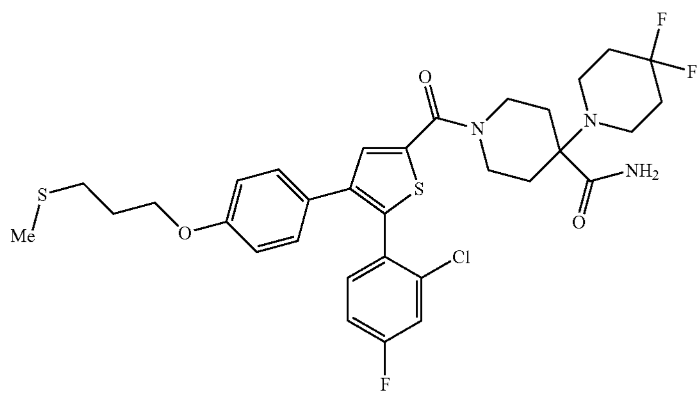 [SMILES: CSCCCOc1ccc(-c2cc(C(=O)N3CCC(C(N)=O)(N4CCC(F)(F)CC4)CC3)sc2-c2ccc(F)cc2Cl)cc1] |
| 1'-{[5-(2-chloro-4-fluorophenyl)-4-{4-[3-(methylsulphonyl)propoxy]phenyl}-2-thienyl]carbonyl}-4,4-difluoro-1,4'-bipiperidine-4'-carboxamide | 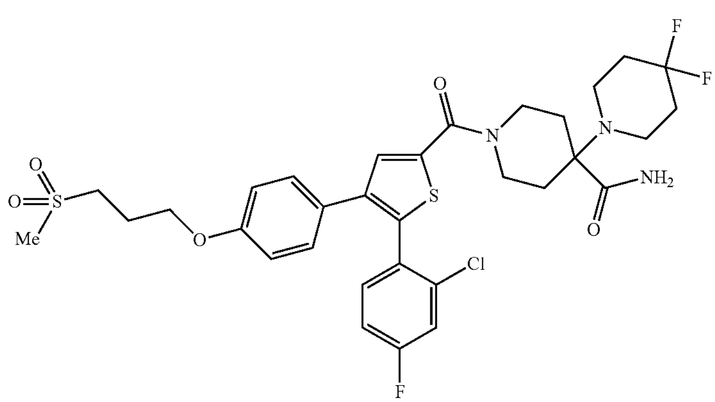 [SMILES: CS(=O)(=O)CCCOc1ccc(-c2cc(C(=O)N3CCC(C(N)=O)(N4CCC(F)(F)CC4)CC3)sc2-c2ccc(F)cc2Cl)cc1] |

| IUPAC Name | Chemical Structure |
| --- | --- |
| 1-{[4-{4-[(2-aminoethyl)thio]phenyl}-5-(2,4-dichlorophenyl)-2-thienyl]carbonyl}-4-phenylpiperidine-4-carboxamide | 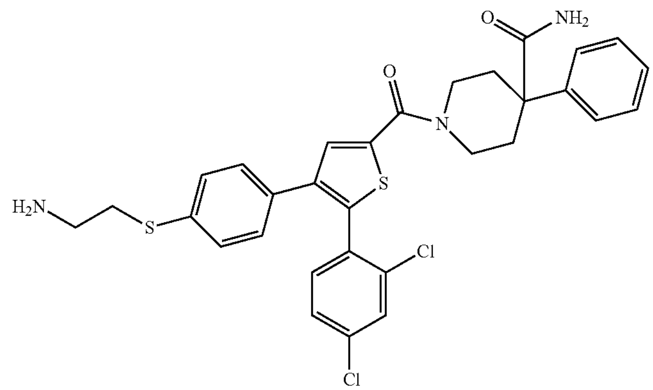 [SMILES: NCCSc1ccc(-c2cc(C(=O)N3CCC(C(N)=O)(c4ccccc4)CC3)sc2-c2ccc(Cl)cc2Cl)cc1] |
| 1-({5-(2,4-dichlorophenyl)-4-[4-({2-[(methylsulphonyl)amino]ethyl}thio)phenyl]-2-thienyl}carbonyl)-4-phenylpiperidine-4-carboxamide | 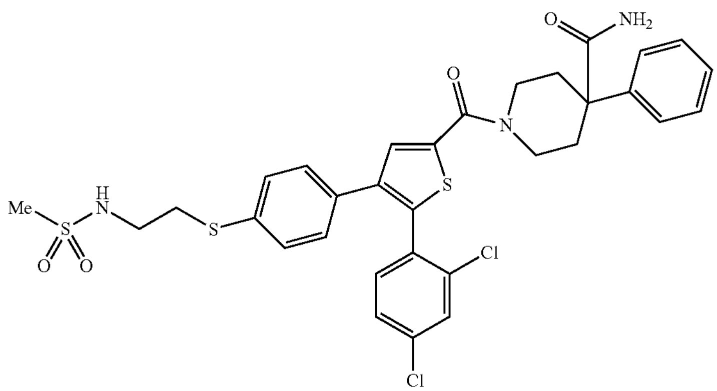 [SMILES: CS(=O)(=O)NCCSc1ccc(-c2cc(C(=O)N3CCC(C(N)=O)(c4ccccc4)CC3)sc2-c2ccc(Cl)cc2Cl)cc1] |
| 1-({5-(2,4-dichlorophenyl)-4-[4-(2-hydroxyethoxy)phenyl]-2-thienyl}carbonyl)-4-phenylpiperidine-4-carboxamide | 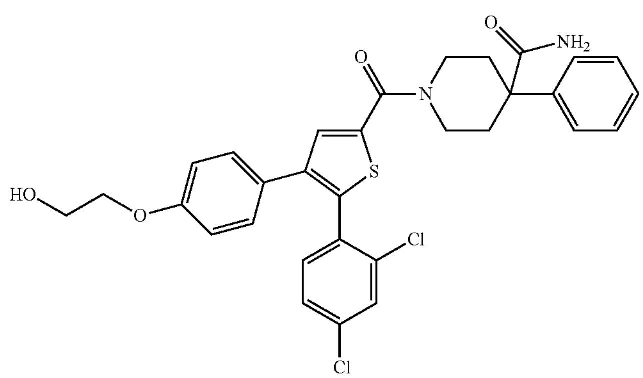 [SMILES: NC(=O)C1(c2ccccc2)CCN(C(=O)c2cc(-c3ccc(OCCO)cc3)c(-c3ccc(Cl)cc3Cl)s2)CC1] |
| 1'-({5-(2,4-dichlorophenyl)-4-[4-(3-hydroxypropoxy)phenyl]-2-thienyl}carbonyl)-4,4-difluoro-1,4'-bipiperidine-4'-carboxamide | 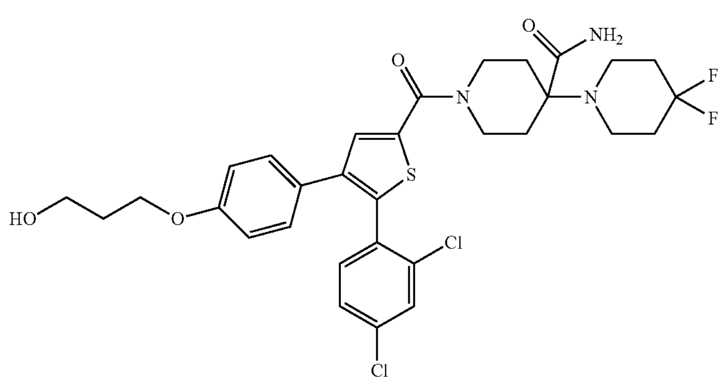 [SMILES: NC(=O)C1(N2CCC(F)(F)CC2)CCN(C(=O)c2cc(-c3ccc(OCCCO)cc3)c(-c3ccc(Cl)cc3Cl)s2)CC1] |

-continued

| IUPAC Name | Chemical Structure |
|---|---|
| 1-({5-(2,4-dichlorophenyl)-4-[4-(3-hydroxypropoxy)phenyl]-2-thienyl}carbonyl)-4-[(2,2,2-trifluoroethyl)amino]piperidine-4-carboxamide | 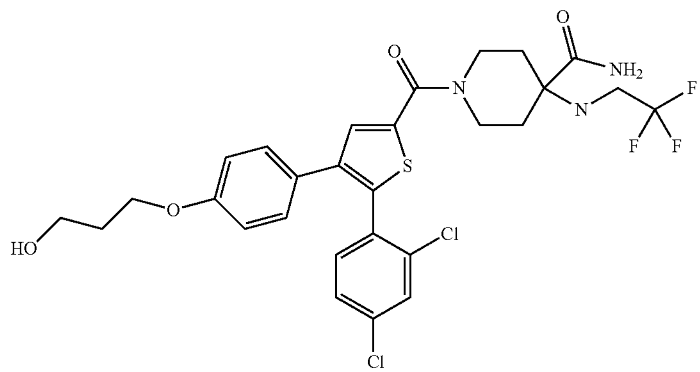 [SMILES: NC(=O)C1(NCC(F)(F)F)CCN(C(=O)c2cc(-c3ccc(OCCCO)cc3)c(-c3ccc(Cl)cc3Cl)s2)CC1] |
| 1'-({5-(2,4-dichlorophenyl)-4-[4-(2-hydroxyethoxy)phenyl]-2-thienyl}carbonyl)-4,4-difluoro-1,4'-bipiperidine-4'-carboxamide | 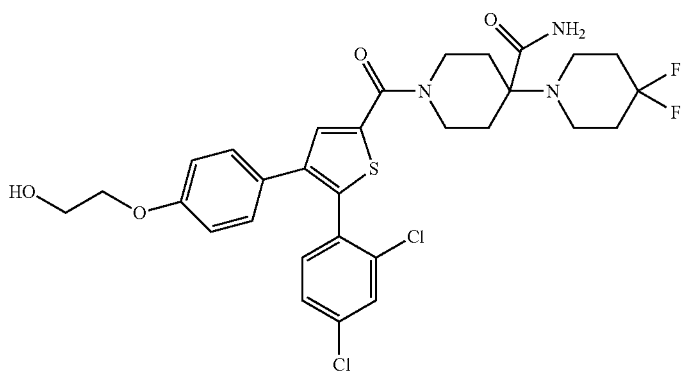 [SMILES: NC(=O)C1(N2CCC(F)(F)CC2)CCN(C(=O)c2cc(-c3ccc(OCCO)cc3)c(-c3ccc(Cl)cc3Cl)s2)CC1] |
| 4-{5-[(4-carbamoyl-4-phenylpiperidin-1-yl)carbonyl]-2-(2,4-dichlorophenyl)thien-3-yl}phenyl propane-1-sulphonate | 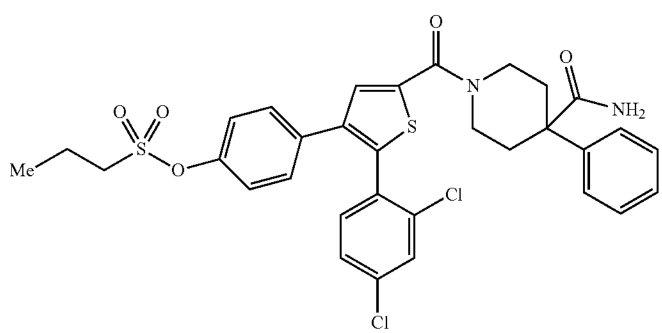 [SMILES: CCCS(=O)(=O)Oc1ccc(-c2cc(C(=O)N3CCC(C(N)=O)(c4ccccc4)CC3)sc2-c2ccc(Cl)cc2Cl)cc1] |
| 1-{[5-(2,4-dichlorophenyl)-4-{4-[(3-hydroxypropyl)sulphonyl]phenyl}-2-thienyl]carbonyl}-4-phenylpiperidine-4-carboxamide | 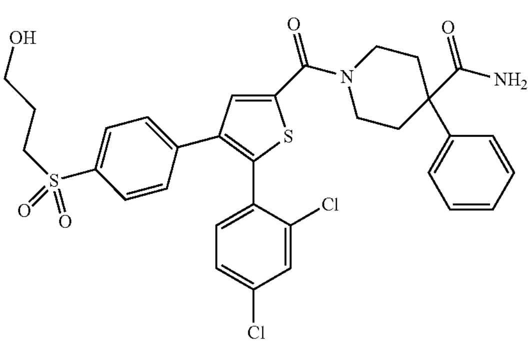 [SMILES: NC(=O)C1(c2ccccc2)CCN(C(=O)c2cc(-c3ccc(S(=O)(=O)CCCO)cc3)c(-c3ccc(Cl)cc3Cl)s2)CC1] |

| IUPAC Name | Chemical Structure |
| --- | --- |
| 1-{[5-(2,4-dichlorophenyl)-4-{4-[(3-hydroxypropyl)thio]phenyl}-2-thienyl]carbonyl}-4-phenylpiperidine-4-carboxamide | 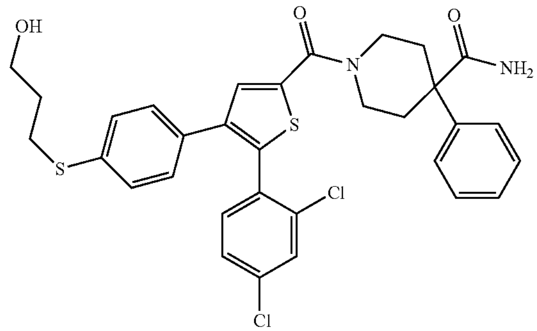 [SMILES: NC(=O)C1(c2ccccc2)CCN(C(=O)c2cc(-c3ccc(SCCCO)cc3)c(-c3ccc(Cl)cc3Cl)s2)CC1] |
| 1-({4-[4-(3-amino-3-oxopropoxy)phenyl]-5-(2-chlorophenyl)-2-thienyl}carbonyl)-4-phenylpiperidine-4-carboxamide | 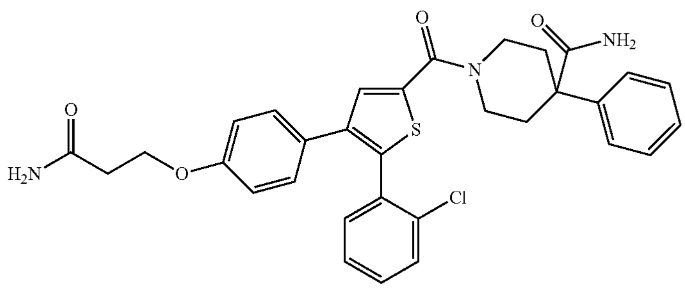 [SMILES: NC(=O)CCOc1ccc(-c2cc(C(=O)N3CCC(C(N)=O)(c4ccccc4)CC3)sc2-c2ccccc2Cl)cc1] |
| 1-{[5-(2,4-dichlorophenyl)-4-{4-[3-(methylthio)propoxy]phenyl}-2-thienyl]carbonyl}-4-phenylpiperidine-4-carboxamide | 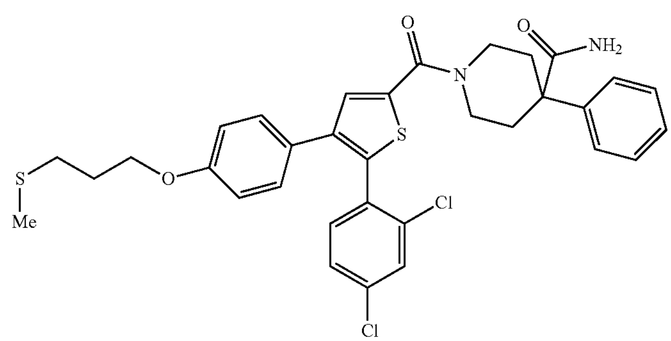 [SMILES: CSCCCOc1ccc(-c2cc(C(=O)N3CCC(C(N)=O)(c4ccccc4)CC3)sc2-c2ccc(Cl)cc2Cl)cc1] |
| 1-{[5-(2,4-dichlorophenyl)-4-{4-[3-(methylsulphonyl)propoxy]phenyl}-2-thienyl]carbonyl}-4-phenylpiperidine-4-carboxamide | 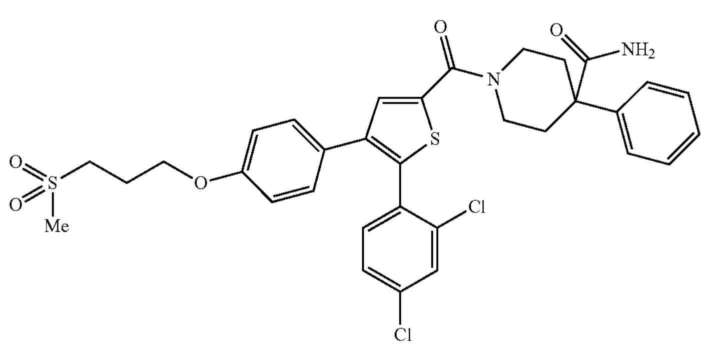 [SMILES: CS(=O)(=O)CCCOc1ccc(-c2cc(C(=O)N3CCC(C(N)=O)(c4ccccc4)CC3)sc2-c2ccc(Cl)cc2Cl)cc1] |

-continued

| IUPAC Name | Chemical Structure |
|---|---|
| 1-{[5-(2,4-dichlorophenyl)-4-{4-[(4-hydroxybutyl)thio]phenyl}-2-thienyl]carbonyl}-4-[(3,3,3-trifluoropropyl)amino]piperidine-4-carboxamide | 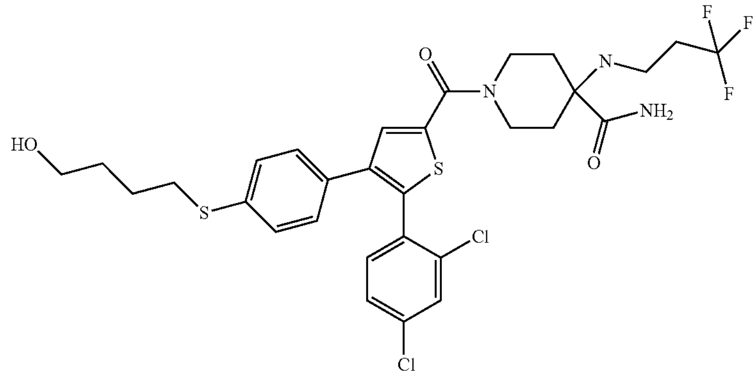 [SMILES: NC(=O)C1(NCCC(F)(F)F)CCN(C(=O)c2cc(-c3ccc(SCCCCO)cc3)c(-c3ccc(Cl)cc3Cl)s2)CC1] |
| 1-({5-(2,4-dichlorophenyl)-4-[4-(2-hydroxyethoxy)phenyl]thien-2-yl}carbonyl)-4-[(3,3,3-trifluoropropyl)amino]piperidine-4-carboxamide | 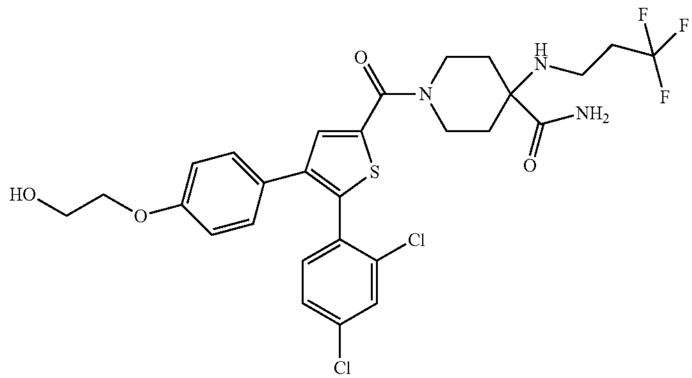 [SMILES: NC(=O)C1(NCCC(F)(F)F)CCN(C(=O)c2cc(-c3ccc(OCCO)cc3)c(-c3ccc(Cl)cc3Cl)s2)CC1] |
| 1-[4-[4-(butane-1-sulphonyl)phenyl]-5-(2,4-dichlorophenyl)thiophene-2-carbonyl]-4-phenylpiperidine-4-carboxamide | 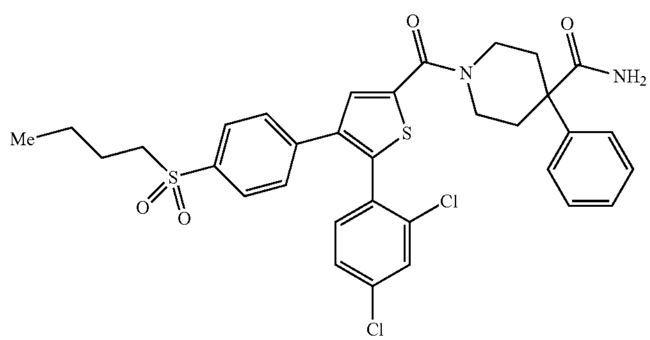 [SMILES: CCCCS(=O)(=O)c1ccc(-c2cc(C(=O)N3CCC(C(N)=O)(c4ccccc4)CC3)sc2-c2ccc(Cl)cc2Cl)cc1] |
| 1'-{5-(2,4-dichlorophenyl)-4-[4-(4-hydroxybutylsulphanyl)phenyl]thiophene-2-carbonyl}-4,4-difluoro-1,4'-bipiperidinyl-4'-carboxamide | 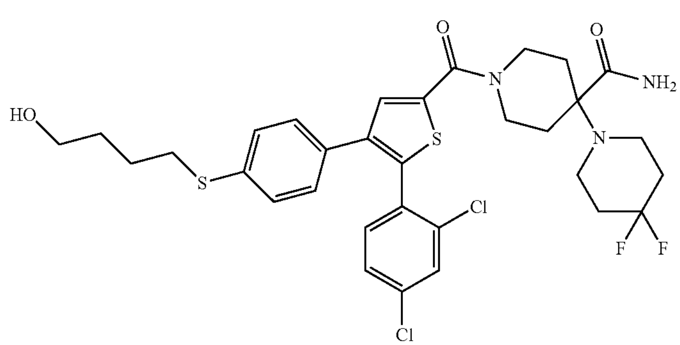 [SMILES: NC(=O)C1(N2CCC(F)(F)CC2)CCN(C(=O)c2cc(-c3ccc(SCCCCO)cc3)c(-c3ccc(Cl)cc3Cl)s2)CC1] |

| IUPAC Name | Chemical Structure |
|---|---|
| 1-({5-(2-chloro-4-fluorophenyl)-4-[4-(3-hydroxypropoxy)phenyl]thien-2-yl}carbonyl)-3-phenylazetidine-3-carboxamide | 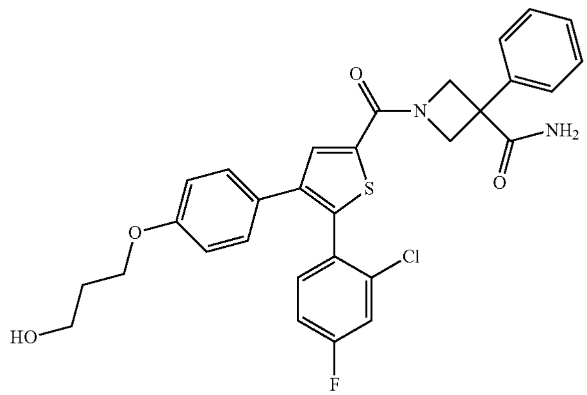 [SMILES: NC(=O)C1(c2ccccc2)CN(C(=O)c2cc(-c3ccc(OCCCO)cc3)c(-c3ccc(F)cc3Cl)s2)C1] |
| 1'-{5-(2,4-dichlorophenyl)-4-[4-(3-hydroxypropylsulphanyl)phenyl]-thiophene-2-carbonyl}-4,4-difluoro-1,4'-bipiperidinyl-4'-carboxamide | 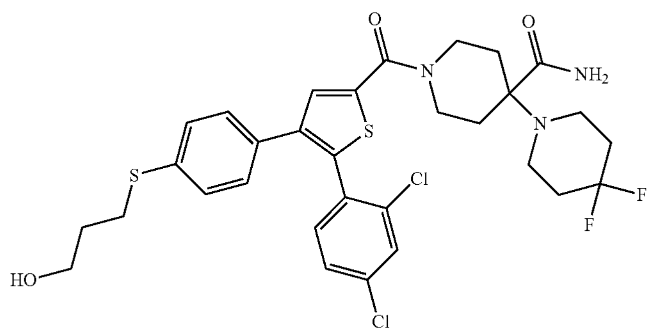 [SMILES: NC(=O)C1(N2CCC(F)(F)CC2)CCN(C(=O)c2cc(-c3ccc(SCCCO)cc3)c(-c3ccc(Cl)cc3Cl)s2)CC1] |
| 1-{5-(2,4-dichlorophenyl)-4-[4-(2-hydroxyethoxy)phenyl]thiophene-2-carbonyl}-3-phenylazetidine-3-carboxamide | 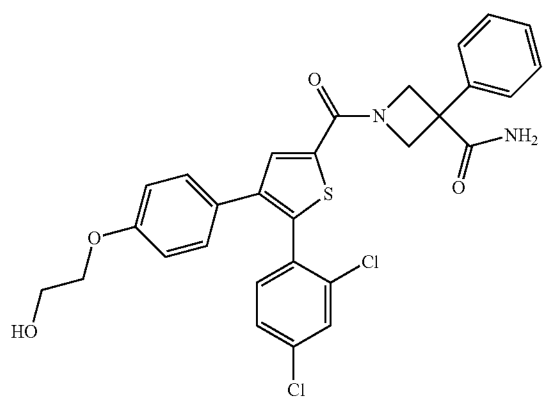 [SMILES: NC(=O)C1(c2ccccc2)CN(C(=O)c2cc(-c3ccc(OCCO)cc3)c(-c3ccc(Cl)cc3Cl)s2)C1] |
| 1-{5-(2,4-dichlorophenyl)-4-[4-(3-hydroxypropoxy)phenyl]thiophene-2-carbonyl}-3-phenylazetidine-3-carboxamide | 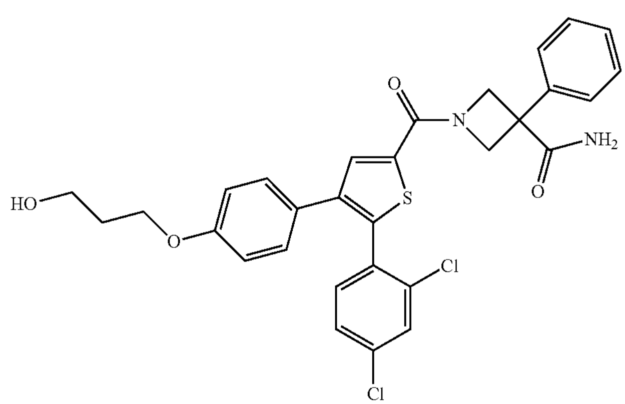 [SMILES: NC(=O)C1(c2ccccc2)CN(C(=O)c2cc(-c3ccc(OCCCO)cc3)c(-c3ccc(Cl)cc3Cl)s2)C1] |

| IUPAC Name | Chemical Structure |
|---|---|
| 1-({5-(2-chlorophenyl)-4-[4-(3-hydroxypropoxy)phenyl]thien-2-yl}carbonyl)-4-phenylpiperidine-4-carboxamide | 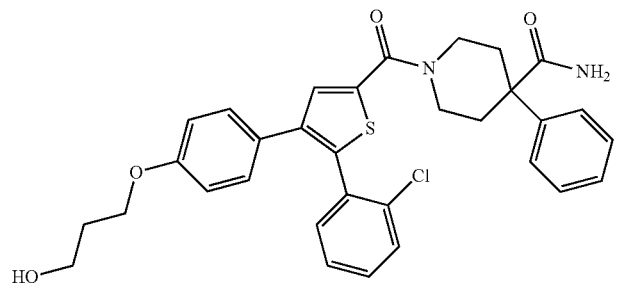 [SMILES: NC(=O)C1(c2ccccc2)CCN(C(=O)c2cc(-c3ccc(OCCCO)cc3)c(-c3ccccc3Cl)s2)CC1] |
| 1-({5-(2-chlorophenyl)-4-[4-(3-hydroxypropoxy)phenyl]thien-2-yl}carbonyl)-4-[(4-fluorobenzyl)amino]piperidine-4-carboxamide | 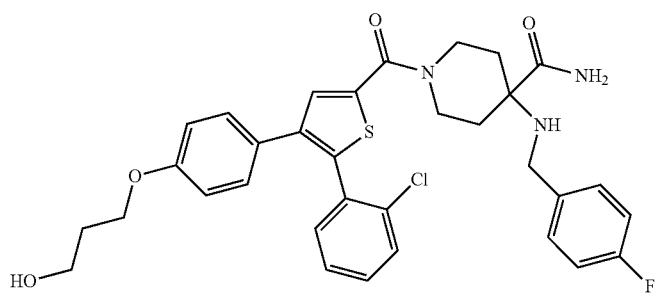 [SMILES: NC(=O)C1(NCc2ccc(F)cc2)CCN(C(=O)c2cc(-c3ccc(OCCCO)cc3)c(-c3ccccc3Cl)s2)CC1] |
| 1-({5-(2-chlorophenyl)-4-[4-(2-hydroxyethoxy)phenyl]thien-2-yl}carbonyl)-4-phenylpiperidine-4-carboxamide | 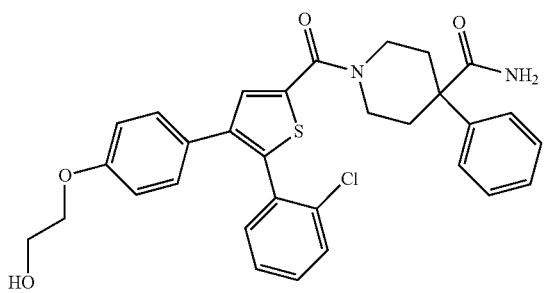 [SMILES: NC(=O)C1(c2ccccc2)CCN(C(=O)c2cc(-c3ccc(OCCO)cc3)c(-c3ccccc3Cl)s2)CC1] |
| 1-({5-(2-chlorophenyl)-4-[4-(2-hydroxyethoxy)phenyl]thien-2-yl}carbonyl)-4-[(4-fluorobenzyl)amino]piperidine-4-carboxamide | 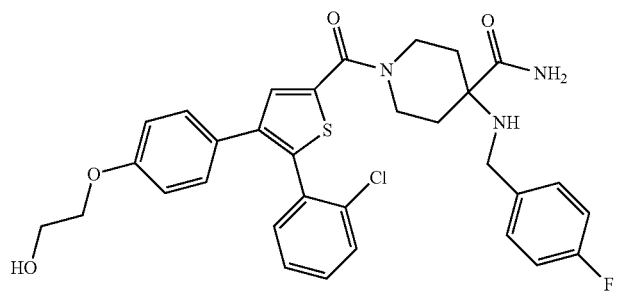 [SMILES: NC(=O)C1(NCc2ccc(F)cc2)CCN(C(=O)c2cc(-c3ccc(OCCO)cc3)c(-c3ccccc3Cl)s2)CC1] |

Another subject-matter of the present invention is a process for the preparation of the compounds according to the invention.

This process is characterized in that the acid of formula (III) or a functional derivative of this acid of formula (II):

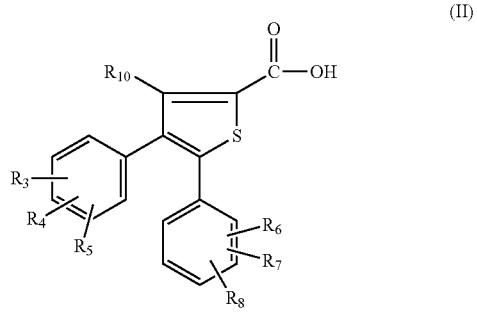

(II)

in which $R_3$, $R_4$, $R_5$, $R_6$, $R_7$, $R_8$ and $R_{10}$ are as defined for (I) and the Y-A-$R_9$ group is replaced with a Z group which is a chemical precursor of the Y-A-$R_9$ group, is treated with an amine of formula (III) $HNR_1R_2$ in which $R_1$ and $R_2$ are as defined for (I).

Z group is understood to mean chemical groups which result, after one or more reaction stages known to a person skilled in the art, in the Y-A-$R_9$ groups. For example, the Z precursor group corresponds to Y—H, a halogen atom or a Y-A-OH, Y-A-Cl, Y-A-$CO_2$Alk, Y-A-S-Alk, Y-Alk, Y-A-OPr or Y-A-NHPg group. The Alk radical corresponds to a linear or branched carbon-comprising radical comprising in particular from 1 to 6 carbon atoms and preferably corresponds to a methyl radical. The Pg group corresponds to a protective group for the amine functional group, for example tert-butyloxycarbonyl. Other examples of Pg protective groups are given in "Protective Groups in Organic Synthesis", Green et al., 4th edition, John Wiley & Sons Inc., New York, 2007. The Pr group corresponds to a protective group for the alcohol functional group, for example tetrahydropyranyl (THP), tetrabutyldimethylsilyl (TBDMS) and trimethylsilyl (TMS).

The compounds of formula (I) obtained by the various procedures can subsequently be separated from the reaction medium and purified according to conventional methods for example by crystallization or chromatography.

The compound of formula (I) thus obtained is optionally converted into one of its salts.

Use may be made, as functional derivative of the acid (II), of the acid chloride, the anhydride, the mixed anhydride, a $C_1$-$C_4$ alkyl ester in which the alkyl is straight or branched, a benzyl ester, an activated ester, for example the p-nitrophenyl ester, or the free acid opportunely activated, for example with a coupling agent, such as N,N'-dicyclohexylcarbodiimide, {benzotriazol-1-yloxy}tris(dimethylamino)phosphonium hexafluorophosphate (BOP), {benzotriazol-1-yloxy}tris(pyrrolidino)phosphonium hexafluorophosphate (PyBOP), 2-(1H-benzotriazol-1-yl)-1,1,3,3-tetramethyluronium) hexafluorophosphate (HBTU) or O-{benzotriazol-1-yl}-N,N,N',N'-tetramethyluronium tetrafluoroborate (TBTU).

Thus, in the process according to the invention, the chloride of the acid of formula (II), obtained by reaction of thionyl chloride or 1-chloro-N,N-2-trimethyl-1-propen-1-amine, carried out according to Chem. Comm., 1988, 475-477, at 0° C., with the acid of formula (II), can be reacted with an amine $HNR_1R_2$ in an inert solvent, such as a chlorinated solvent (for example dichloromethane, dichloroethane or chloroform), an ether (for example tetrahydrofuran or dioxane) or an amide (for example N,N-dimethylformamide), under an inert atmosphere, at a temperature of between 0° C. and ambient temperature, in the presence of a tertiary amine, such as triethylamine, N-methylmorpholine or pyridine.

An alternative form consists in preparing the mixed anhydride of the acid of formula (II) by reaction of ethyl chloroformate with the acid of formula (II) in the presence of a base, such as triethylamine, and in reacting it with an amine $HNR_1R_2$ in a solvent, such as dichloromethane, under an inert atmosphere, at ambient temperature, in the presence of a base, such as triethylamine.

The compounds of formula (II) can be prepared according to Scheme 1 below.

For this method of preparation, the Z precursor group is:
either present in the compound (IV); in this case, $R_3$ represents the Z group;
or present in the compound (V); in this case, $R_6$ represents the Z group.

SCHEME 1

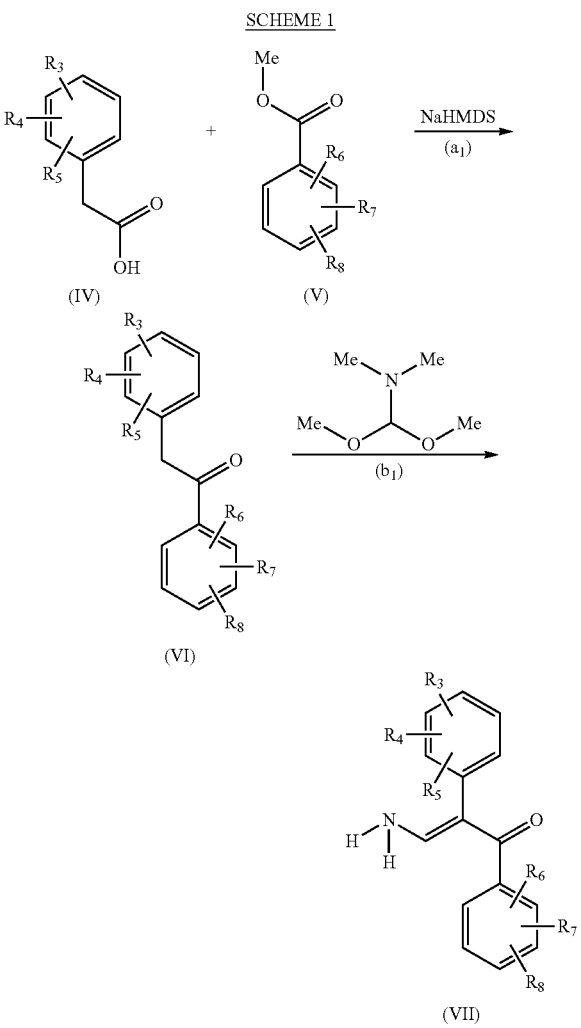

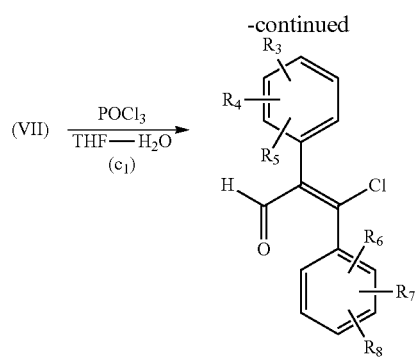
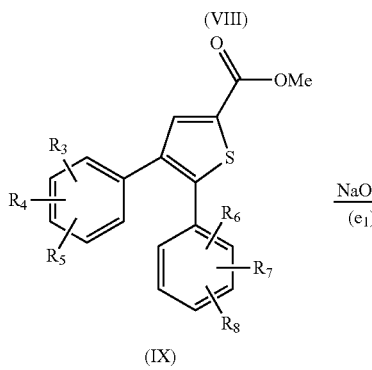
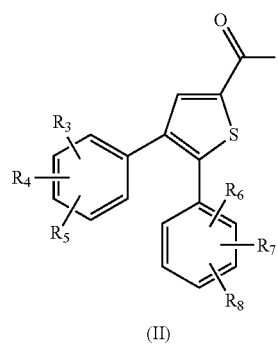

The preparation of the compounds of formula (VI) is carried out starting from the compounds of formulae (IV) and (V) in the presence of a strong base, such as, for example, sodium hexamethyldisilazane (NaHMDS), lithium hexamethyldisilazane (LiHMDS), sodium dicyclohexylamide (LiNCy$_2$) or lithium diisopropylamide (LDA).

After reaction in stage (b1) with 1,1-dimethoxy-N,N-dimethylmethanamine, the compounds (VII) are reacted with phosphoryl trichloride, followed by hydrolysis in the presence of a solvent-water mixture, such as, for example, tetrahydrofuran-water or dioxane-water.

The cyclization with methyl mercaptoacetate in stage (d1) is carried out in the presence of a base, such as, for example, a hindered amine: 1,8-diazabicyclo[5.4.0]undec-7-ene (DBU) or 1,3-diazabicyclo[5.4.0]undecane (DBN). The compounds of formula (IX) obtained are subsequently treated with sodium hydroxide to result in the compounds of formula (II).

The compounds of formula (II) and functional derivatives of the acid (II) can also be prepared according to the methods of preparation described in International Application WO 2005/035488 (see in particular page 4, line 31, to page 9, line 32).

These compounds of formula (II) and functional derivatives of the acid (II) subsequently result, in one or more stages, in the compounds of formula (I) according to the invention.

Thus, according to Scheme 2 below, the starting material is the acid of formula (IIa), in which R$_6$ is replaced with the Z group. This acid is treated with an amine of formula (III) HNR$_1$R$_2$, R$_1$ and R$_2$ being as defined for (I). An amide of formula (Xa) is obtained.

The Z group of the compound of formula (Xa) obtained is then converted, in one or more stages, to the Y-A-R$_9$ group by one of the methods known to a person skilled in the art, in order to result in the compounds of formula (I).

SCHEME 2

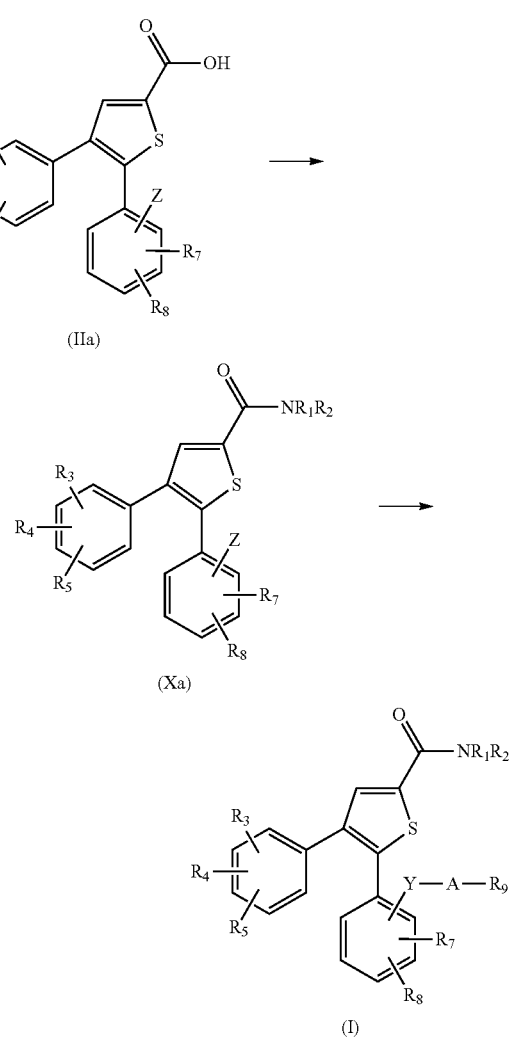

Or else, according to Scheme 2' below, the starting material is the acid of formula (IIb) in which R$_3$ is replaced with the Z group. This acid is treated with an amine of formula (III) HNR$_1$R$_2$, R$_1$ and R$_2$ being as defined for (I). An amide of formula (Xb) is obtained.

The Z group for the compound of formula (Xb) obtained is then converted, in one or more stages, to the Y-A-R$_9$ group by one of the methods known to the person skilled in the art, in order to result in the compounds of formula (I).

SCHEME 2'

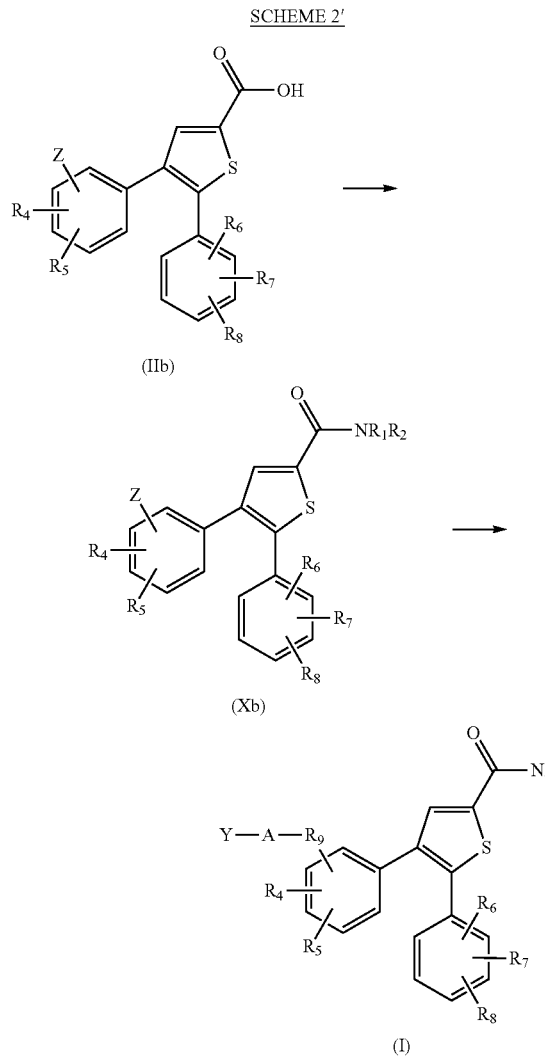

SCHEME 3

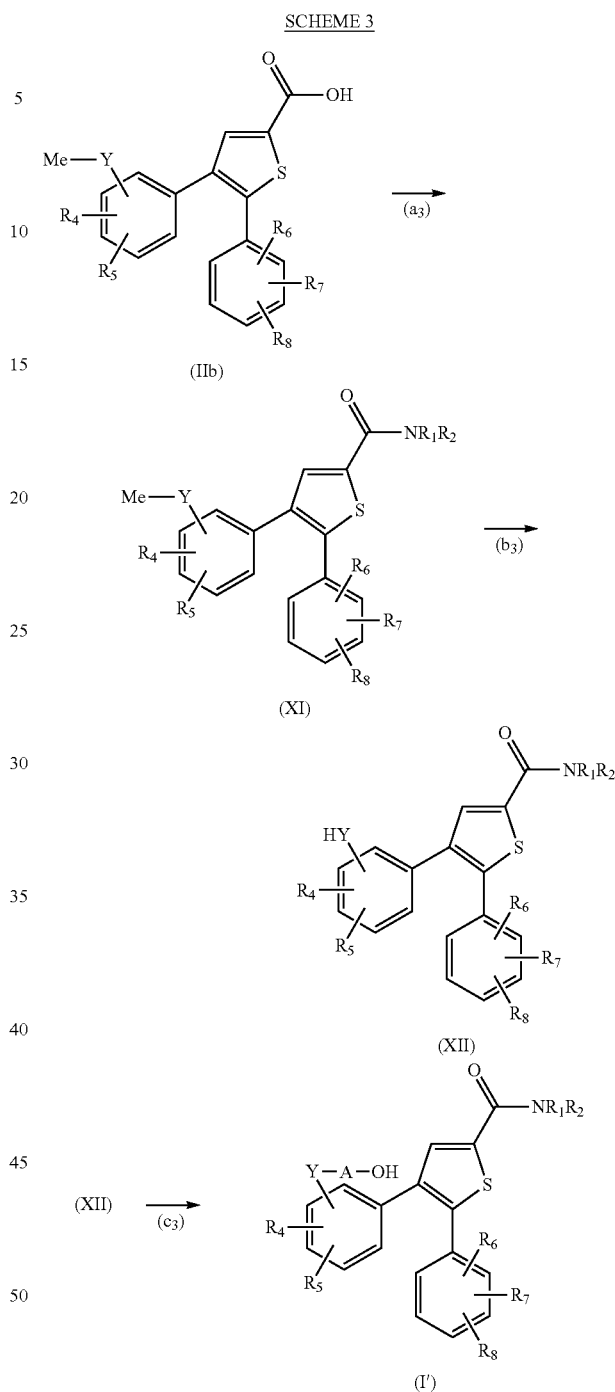

By way of examples, the compounds of formula (I) in which Y corresponds to an oxygen atom and R$_9$ represents an OR$_{19}$, CO$_2$R$_{19}$, CONR$_{19}$R$_{20}$, NR$_{19}$R$_{20}$, NR$_{18}$SO$_2$R$_{21}$ or S(O)$_n$R$_{21}$ group can be obtained from compounds of formula (IIb) in which R$_3$ is replaced with Z, and Z corresponds to Y-Alk. Alk being a linear or branched carbon-comprising radical, preferably a methyl radical.

According to Scheme 3, the compound (XI) obtained by a reaction of the compound (IIb) and the amine HNR$_1$R$_2$ is treated, in stage (b3), with boron tribromide and then the compound (XII) is treated, in stage (c3), with a chloroalkanol of formula Cl-A-OH or bromoalkanol of formula Br-A-OH in an alkaline medium (e.g.: potassium carbonate or caesium carbonate) to result in the compound of formula (I) in which R$_9$ corresponds to an —OH radical.

The compounds of formula (I) obtained on conclusion of Reaction Scheme 3, reference (I'), can result in other compounds of formula (I).

In particular, according to Scheme 4, the compounds (P) make it possible to prepare the compounds of formula (I) in which Y-A-R$_9$ corresponds to Y-A-S—R$_{21}$. In stage (a4), the compound of formula (I') is treated with mesyl chloride in the presence of an amine, such as, for example, triethylamine. The compound obtained is then treated with a sodium thioalkoxide of formula R$_{21}$SNa to result in the compound of formula (I'') in which R$_9$ corresponds to an —S—R$_{21}$ radical.

SCHEME 4

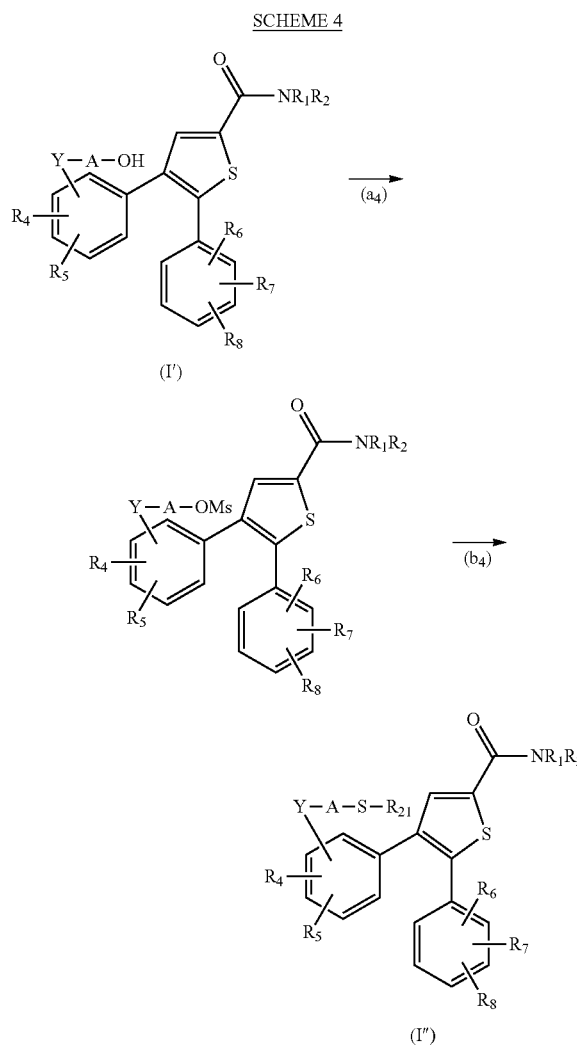

In agreement with Scheme 5, the compounds of formula (I) obtained on conclusion of Reaction Scheme 4, reference (I″), can subsequently be treated with 3-chloroperoxybenzoic acid (MCPBA) to result in the compounds of formula (I‴) in which $R_9$ corresponds to an —S(O)$_{n'}$—$R_{21}$ radical with n' equal to 1 or 2.

SCHEME 5

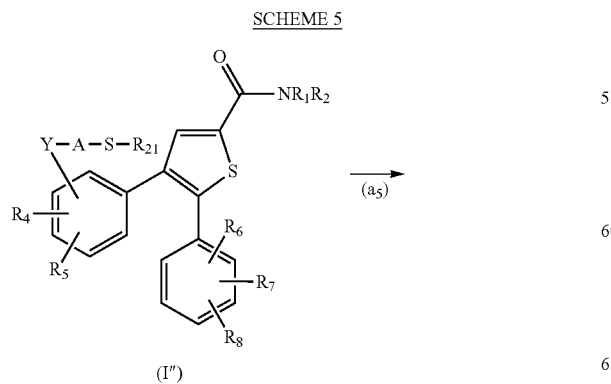

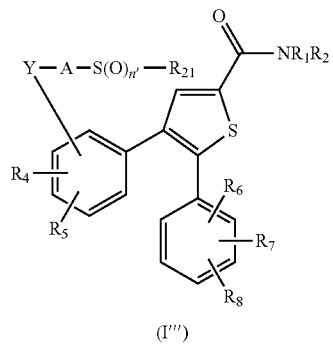

The compounds of formula (XII) can result in other compounds of formula (I). For example, in a first stage, tert-butyl (3-bromopropyl)carbamate is added to a compound of formula (XII) and then, in a second stage, TFA is added in order to obtain a compound of formula (I) in which —$R_9$ corresponds to an —$NH_2$ radical.

The compounds of formula (II) also make it possible to result in compounds of formula (I) in which Y corresponds to the divalent —S(O)$_n$— radical and —$R_9$ represents an —$OR_{19}$, —$CH_3$ or —$CF_3$ radical.

For example, the starting material is a compound of formula (IIb) in which Z corresponds to a Br atom.

According to Scheme 6, the compound of formula (IIb) with Z corresponding to Br is brought into contact with a reactant of formula HS-A-$OR_{19}$ and sodium hydride. A catalyst, such as $Pd_2(dba)_3$, and a ligand, such as the organophosphorus compound Xantphos, are subsequently added in order to arrive at a compound of formula (XIII). This compound of formula (XIII) corresponds to a compound of formula (I) in which —Y-A-$R_9$ is —S-A-$OR_{19}$.

SCHEME 6

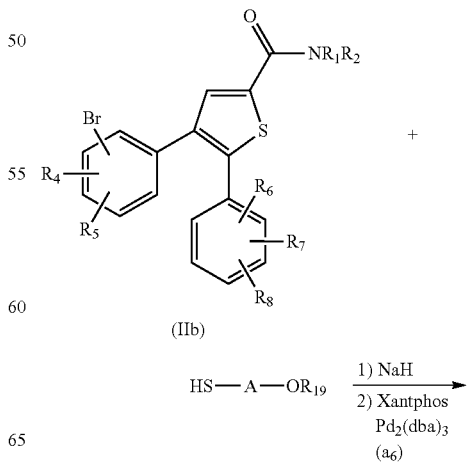

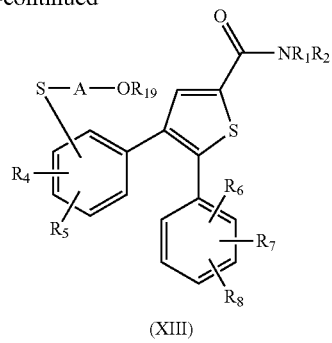

(XIII)

According to Scheme 7, the compound (XIII) obtained via the procedure of Scheme 6 can subsequently be treated with MCPBA to oxidize the sulphur present on the side chain of the phenyl and to result in compounds of formula (I) in which —Y-A-$R_9$ is —(SO)-A-$OR_{19}$ (hereinafter the compound of formula (XIV)) or —$SO_2$-A-$OR_{19}$ (hereinafter the compound of formula (XV)).

SCHEME 7

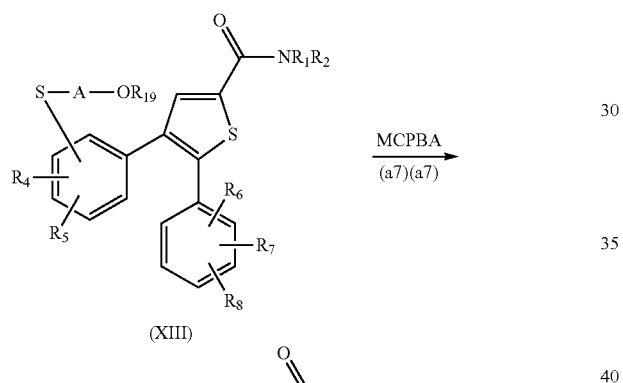

By replacing the reactant HS-A-$OR_{19}$ with a reactant of formula HS-A-$CH_3$ or HS-A-$CF_3$ in the reaction sequence of Scheme 6, the compounds of formulae (XIII') and (XIII") with n" equal to 0, 1 or 2 are prepared:

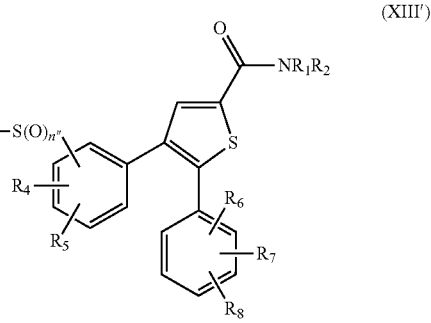

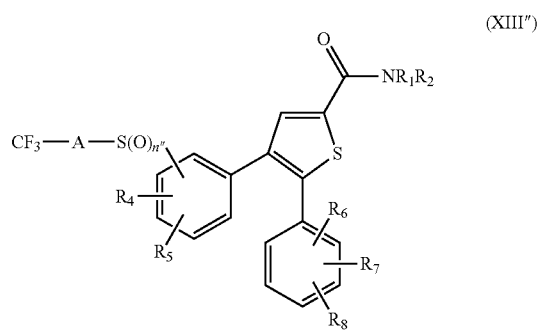

The compounds of formula (IX) where $R_3$ or $R_6$ corresponds to Z and Z is OAlk also make it possible to result in compounds of formula (I) where Y-A-$R_9$ corresponds to O-A-OH or O-A-$NHR_{19}$ according to Reaction Scheme 8 below.

Thus, according to Scheme 8, the starting material is the compound of formula (IX) where $R_3$ corresponds to Z and Z is OAlk, referenced (XVI) below.

Alternatively, it is possible to start from the compound of formula (IX) where $R_6$ corresponds to Z and Z is OAlk. In this case, the functionalized radical Y-A-$R_9$ of the final compound is present on the phenyl in the 5 position of the thiophene.

SCHEME 8

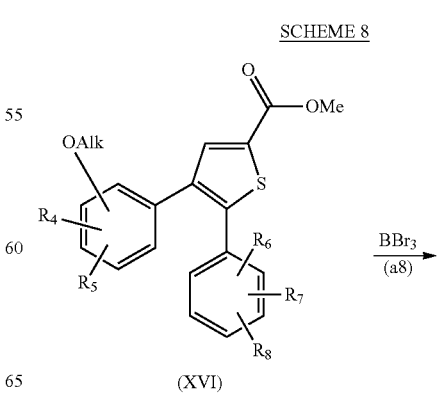

(XVI)

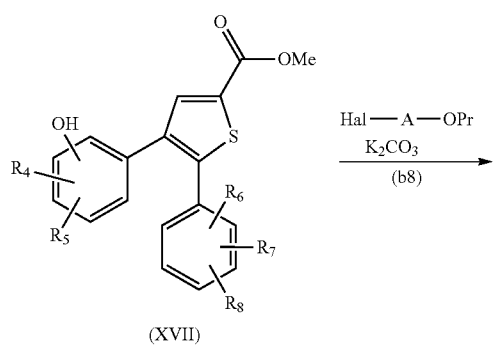

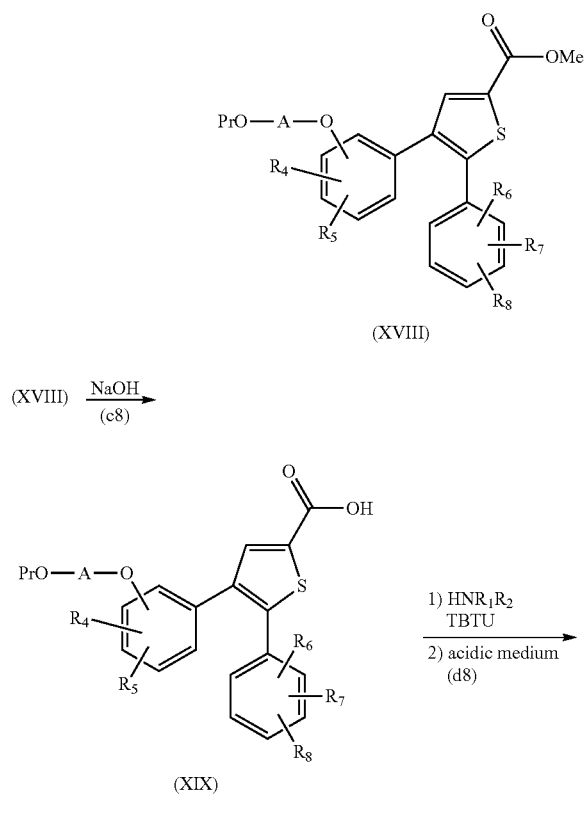

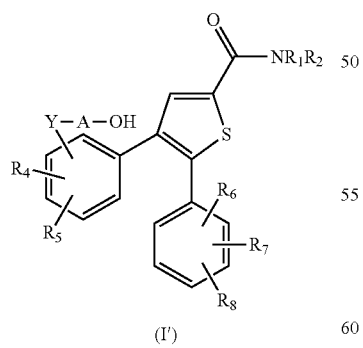

According to Scheme 8, the compound of formula (XVI) is treated with BBr₃. The compound obtained, of formula (XVII), is alkylated with a halogenated derivative of formula Hal-A-OPr, with Hal equal to Br or Cl, in order to obtain an intermediate compound of formula (XVIII) in which Z has become O-A-OPr.

After saponification, for example with NaOH, the acid of formula (XIX) is treated, in stage (d8), with an amine of formula HNR₁R₂ in the presence of a coupling agent, such as, for example, TBTU. The compound obtained is then treated in an acidic medium to result in the compound of formula (I').

In stage (b8), Hal-A-OPr can be replaced with Hal-A-NR₁₉Pg. In this case, after saponification, an intermediate compound of formula (XXI) is obtained and subsequently results in the compounds of formula (I) where Y-A-R₉ corresponds to O-A-NHR₁₉.

SCHEME 9

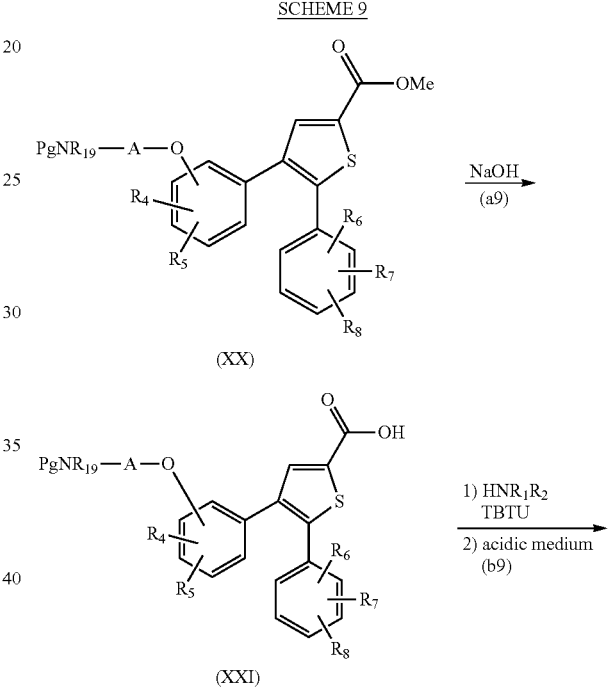

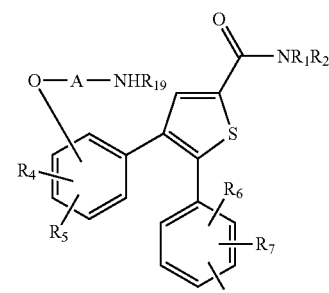

In stage (b8), Hal-A-OPr can also be replaced with Hal-A-NR₁₉R₂₀ with R₁₉ and R₂₀ other than a hydrogen atom. In this case, after saponification, an intermediate compound of formula (XXIII) is obtained and subsequently results in the compounds of formula (I) where Y-A-R₉ corresponds to O-A-NR₁₉R₂₀.

SCHEME 10

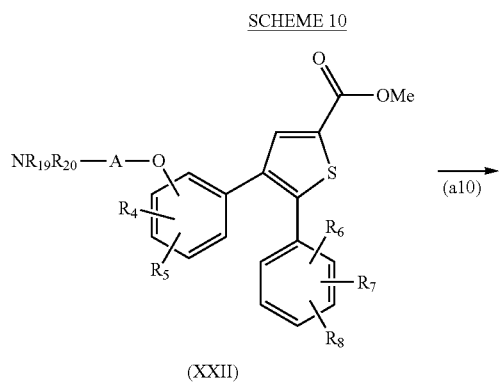

(XXII)

(a10) →

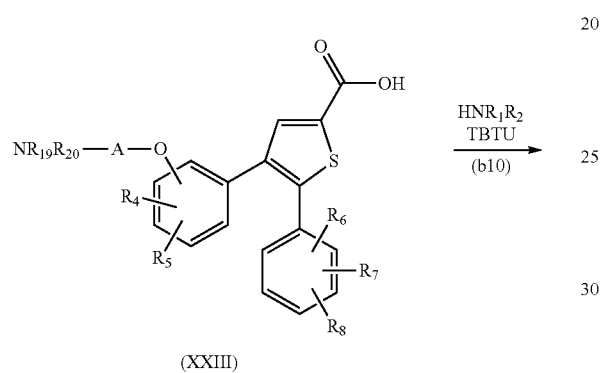

(XXIII)

HNR₁R₂
TBTU
(b10) →

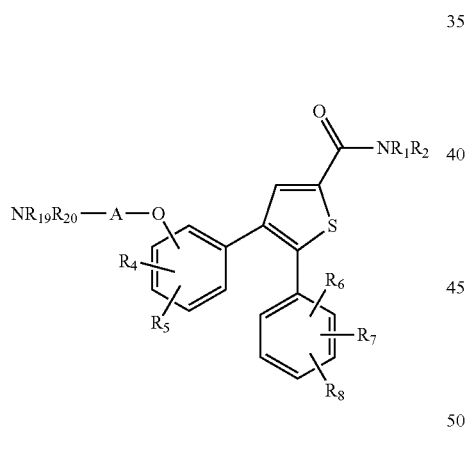

SCHEME 11

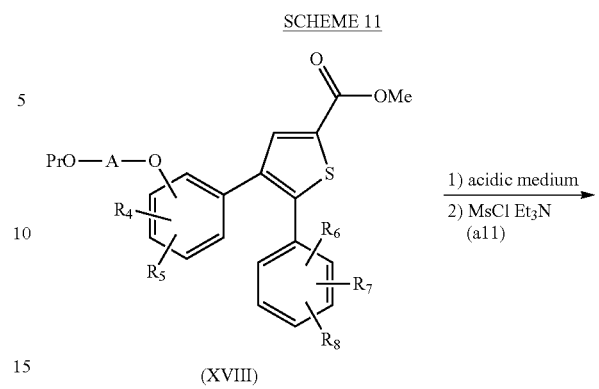

(XVIII)

1) acidic medium
2) MsCl Et₃N
(a11) →

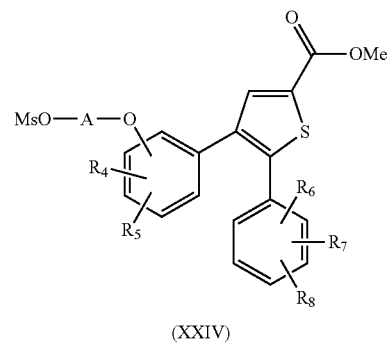

(XXIV)

R₂₁SNa
(b11) →

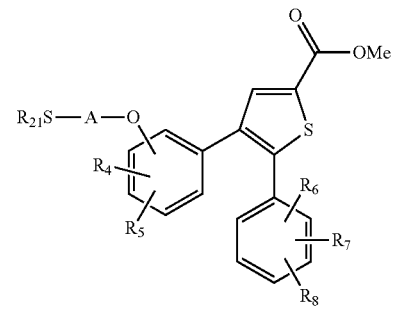

(XXV)

(XXV) $\xrightarrow[(c11)]{\text{NaOH}}$

In addition, it is possible, starting from the compounds of formula (XVIII), to prepare, by following Reaction Scheme 11, compounds of formula (I) where Y-A-R₉ corresponds to O-A-SR₂₁.

On conclusion of stage (b11), the intermediate compounds of formula (XXV) can subsequently be treated with 3-chloroperoxybenzoic acid (MCPBA) to result in intermediate compounds (XXV') in which —R₉ corresponds to an —S(O)ₙ·—R₂₁ radical with n' equal to 1 or 2. Subsequently, these compounds (XXV') follow stages (e11) and (d11) to result in compounds of formula (I''') where Y-A-R₉ corresponds to —O-A-S(O)ₙ·—R₂₁.

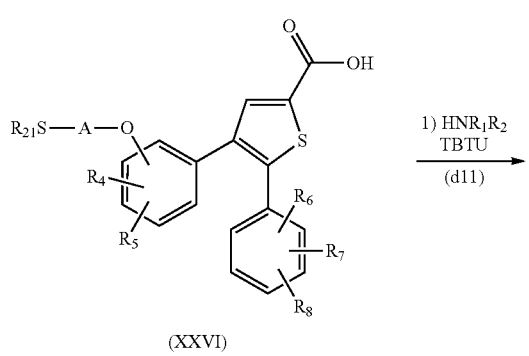

(XXVI)

1) HNR₁R₂
TBTU
(d11) →

-continued

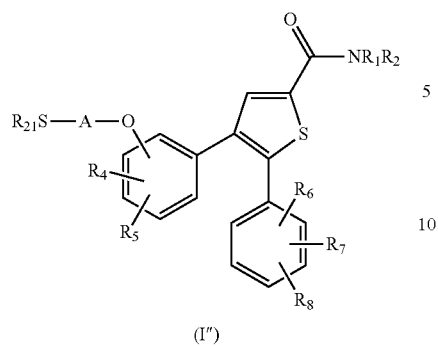

(I″)

It is possible, starting from the compounds of formula (XXVII), by following Reaction Scheme 12, to prepare compounds of formula (I) where Y-A-R$_9$ corresponds to S-A-OR$_{19}$. Stage (a12) is carried out under similar conditions to those of Reaction Scheme 6 and the saponification stage (b12) and then the coupling stage (c12) are carried out under similar conditions to those of stages (c8) and (d8) of Reaction Scheme 8.

SCHEME 12

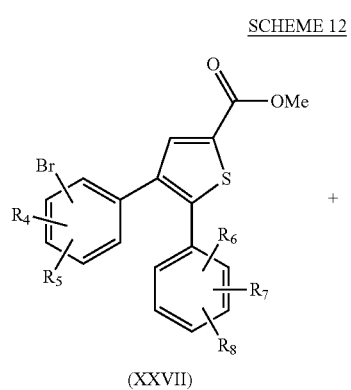

(XXVII)

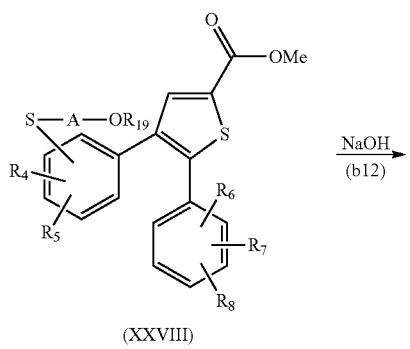

(XXVIII)

-continued

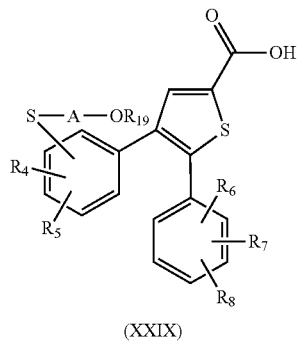

(XXIX)

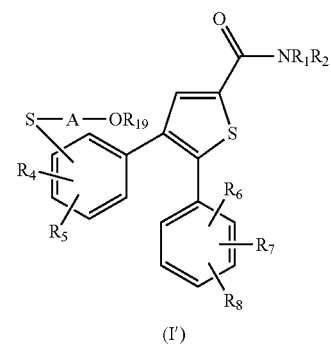

(I′)

The amines of formula (III) HNR$_1$R$_2$ are known or are prepared by known methods, for example that described in J. Med. Chem., 7, 1964, 619-622.

The intermediate compounds of formulae (XXII), (XXIII), (XXV), (XXVI), (XXVIII) and (XXIX) are novel and are used for the preparation of the compounds of formula (I).

The intermediate compounds of formula (XXVII) correspond to the compounds of formula (IX) in which R$_3$ corresponds to a bromine atom. These compounds of formula (XXVII) are prepared according to Reaction Scheme 1.

Another subject-matter of the present invention is the compounds of formulae (XXX) (XXXI) and (XXXII), including in particular compounds of formulae (XXII), (XXIII), (XXV), (XXVI), (XXVIII) and (XXIX). These compounds are used for the preparation of the compounds of formula (I) and correspond to the following formulae:

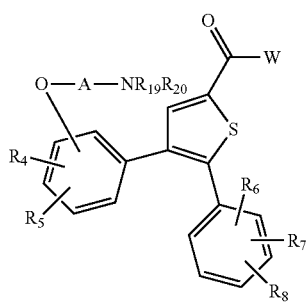

(XXX)

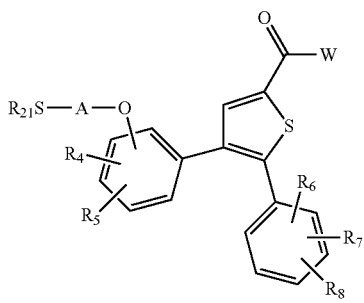

(XXXI)

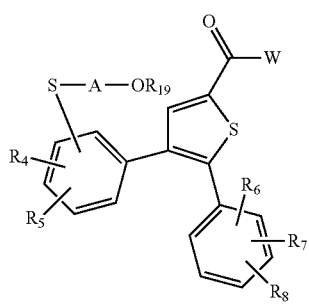

(XXXII)

in which:
W represents a $(C_1-C_4)$alkoxy group, preferably a methoxy group, a halogen, preferably a chlorine atom, or hydroxyl radical,
and other substituents are as defined for the compounds of formula (I).

When W represents a $(C_1-C_4)$alkoxy group, the compounds of formula (XXX), (XXXI) or (XXXII) are treated with a saponification agent, such as, for example, NaOH, and then with an amine of formula (III) $HNR_1R_2$, in which $R_1$ and $R_2$ are as defined for (I), in order to prepare the compounds of formula (I).

When W represents a hydroxyl radical or a chlorine atom, the compounds of formula (XXX), (XXXI) or (XXXII) are treated with an amine of formula (III) $HNR_1R_2$ in which $R_1$ and $R_2$ are as defined for (I), in order to prepare the compounds of formula (I).

The following examples describe the preparation of some compounds in accordance with the invention. These examples are not limiting and serve only to illustrate the present invention.

In the examples, the following abbreviations are used:
AcOEt: ethyl acetate
$AcONH_4$: ammonium acetate
$BBr_3$: boron tribromide
$CH_2Cl_2$: dichloromethane
DBU: 1,8-diazabicyclo[5.4.0]undec-7-ene
DIPEA: diisopropylethylamine
DCM: dichloromethane
DMF: N,N-dimethylformamide
$Et_3N$: triethylamine
HPLC: high performance liquid chromatography
LiHMDS: lithium hexamethyldisilazane
MeOH: methanol
MCPBA: 3-chloroperoxybenzoic acid
MsCl: mesyl chloride
NaHMDS: sodium hexamethyldisilazane
$NH_3$: ammonia
$NH_4OH$: aqueous ammonia
$Pd(dba)_2$: bis(dibenzylideneacetone)palladium
$Pd_2(dba)_3$: tris(dibenzylideneacetone)dipalladium
$POCl_3$: phosphoryl trichloride
$P(tBu)_3$: tri(tert-butyl)phosphine
AT: ambient temperature
TBTU: O-(benzotriazol-1-yl)-N,N,N',N-tetramethyluronium tetrafluoroborate
M.p.: melting point
TFA: trifluoroacetic acid
THF: tetrahydrofuran
HPLC: ultra performance liquid chromatography
Xantphos:

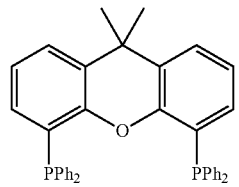

The nuclear magnetic resonance spectra are recorded at 250 MHz or 400 MHz in $d_6$-DMSO. Use is made, in the interpretation of the spectra, of the following abbreviations: s: singlet, d: doublet, t: triplet, q: quartet, qui: quintet, m: unresolved peak, bs: broad singlet, sd: split doublet.

The compounds according to the invention are analysed by coupled LC/UV/MS (liquid chromatography/UV detection/mass spectrometry). The characteristic molecular peak (MH) and the retention time (rt), in minutes (mm), are measured.

The compounds are analysed by coupled HPLC-UV-MS or else HPLC-UV-MS (liquid chromatography/UV detection/mass detection).

The analytical conditions are as follows:
Conditions A (HPLC):
A Symmetry C18 (50×2.1 mm; 3.5 μm) column is used
Eluent A: 0.005% of trifluoroacetic acid (TFA) in water at approximately pH 3.1
Eluent B: 0.005% of TFA in acetonitrile
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C.; flow rate: 0.4 ml/minute
Detection: λ=210 m–220 nm
Conditions B (HPLC):
An XTerra MS C18 (50×2.1 mm; 3.5 μm) column is used
Eluent A: 10 mM $AcONH_4$ at approximately pH 7
Eluent B: acetonitrile
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C.; flow rate: 0.4 ml/minute
Detection: λ=220 nm
Conditions C (HPLC):
An Acquity BEH C18 (50×2.1 mm; 1.7 μm) column is used
Eluent A 0.005% of TFA water at approximately pH 3.1/ acetonitrile (97/3)
Eluent B: 0.035% of TFA in acetonitrile
Gradient:

| Time (min) | % A | % B |
|---|---|---|
| 0 | 100 | 0 |
| 2.3 | 5 | 95 |
| 2.9 | 5 | 95 |
| 3 | 100 | 0 |
| 3.5 | 100 | 0 |

Column temperature: 40° C.; flow rate: 1 ml/minute
Detection: λ=220 nm
Mass Spectrometry Conditions
The mass spectra are recorded in positive electrospray (ESI) mode, in order to observe the ions resulting from the protonation of the compounds analysed (MH) or from the formulation of adducts with other cations, such as $Na^+$, $K^+$, and the like.

PREPARATIONS

Preparation 1: 4-[(3,3,3-Trifluoropropyl)amino]piperidine-4-carboxamide (i) tert-Butyl 4-carbamoyl-4-[(3,3,3-trifluoropropyl)amino]piperidine-1-carboxylate 10 g of tert-butyl 4-amino-4-carbamoylpiperidine-1-carboxylate, 4.42 g of 3,3,3-trifluoropropionaldehyde, 17.61 g of sodium triacetoxyborohydride and 4.51 ml of acetic acid are added at AT to 250 ml of $CH_2Cl_2$ and then the mixture is stirred for 3 hours. Water is added and the expected compound is extracted with $CH_2Cl_2$ and the organic phase is washed with a saturated $NaHCO_3$ solution and then with water. After drying the organic phase, filtering and evaporating to dryness, 13 g of the expected compound are obtained.

(ii) 4-[(3,3,3-Trifluoropropyl)amino]piperidine-4-carboxamide 13 g of the compound obtained in (i) are stirred in 25 ml of MeOH, then 30 ml of ethereal hydrochloric acid (2M) are added and the mixture is left stirring overnight. After filtering and drying, 9.57 g of the expected compound are obtained.

Preparation 2: 4-Phenylpiperidine-4-carboxamide hydrochloride CL (i) 1-Benzyl-4-phenylpiperidine-4-carboxamide hydrochloride 10 g of 1-benzyl-4-phenylpiperidine-4-carbonitrile are added to 77 ml of concentrated sulphuric acid and then the mixture is heated at 100° C. for one hour. The reaction mixture is subsequently added to ice and then basified with $NH_4OH$. The product is extracted with $CH_2Cl_2$ and the extract is dried and evaporated. After crystallizing the hydrochloride from ether, 5.7 g of the expected product are obtained.

(ii) 4-Phenylpiperidine-4-carboxamide hydrochloride 5.6 g of the product obtained in (i), 6.7 g of cyclohexadiene and 0.5 g of 10% palladium-on-charcoal are added to 70 ml of MeOH and the reaction mixture is heated at reflux for 6 hours. The catalyst is filtered off through Celite and the filtrate is evaporated to dryness. After crystallizing from an ether-isopropyl ether mixture, 3 g of the expected product are obtained.

Preparation 3: 3-Phenylazetidine-3-carboxamide formate (i) 1-Benzyl 3-methyl 1,3-azetidinedicarboxylate 10 g of azetidine-3-carboxylic methyl ester hydrochloride and then 23 ml of triethylamine are added to 150 ml of $CH_2Cl_2$. The mixture is cooled and 13.5 g of benzyl chloroformate are added. After leaving overnight at AT, washing is carried out with water and then with HCl (N). After drying, concentrating to dryness and purifying by chromatography on silica (eluent: heptane-AcOEt (gradient from 0% to 50%)), 13.1 g of the expected compound are obtained.

(ii) 1-Benzyl 3-methyl 3-phenyl-1,3-azetidinedicarboxylate 5.11 ml of bromobenzene, then 0.5 g of $Pd(dba)_2$, 2.15 ml of a 10% solution of tri(tert-butyl)phosphine ($P(tBu)_3$) in hexane and then 8.4 g of LiHMDS are added to 40 ml of toluene. 11 g of the compound obtained in the preceding stage (i) in 10 ml of toluene are added while maintaining the temperature between 15 and 20° C. After leaving overnight, the mixture is poured onto a saturated $NH_4Cl$ solution, extraction is carried out with ether and the extract is dried with $MgSO_4$ and concentrated to dryness. After purifying by chromatography on silica (eluent: heptane-AcOEt (gradient from 0% to 30%)), 3.25 g of the expected compound are obtained.

(iii) Benzyl ester of 3-phenylazetidine-1,3-dicarboxylic acid 3.7 g of the compound obtained in the preceding stage (ii) and then 3 ml of 30% sodium hydroxide solution are added to 40 ml of methanol. The mixture is heated at reflux for 1 hour and then concentrated to dryness. The residue is taken off in water, washing is carried out with ether and acidification is carried out with concentrated HCl. After extracting with ether, drying, concentrating to dryness and crystallizing from pentane, 2.87% of the expected compound are obtained.

(iv) Benzyl ester of 3-carbamoyl-3-phenylazetidine-1-carboxylic acid 2.87 g of the compound obtained in the preceding stage (iii), 2.4 ml of DIPEA and then 3.3 g of TBTU are added to 60 ml of $CH_2Cl_2$. $NH_3$ is sparged into the medium while maintaining the temperature at 25° C. The mixture is stirred at AT overnight. It is concentrated to dryness, the residue is taken off in ethyl acetate and washing is carried out with water, then with HCl (N) and finally with a 10% aqueous $NaHCO_3$ solution.

After drying, concentrating to dryness and then crystallizing from ether, 1.51 g of the expected compound are obtained.

(v) 3-Phenylazetidine-3-carboxamide formate 1.51 g of the compound obtained in the preceding stage (iv), 1.57 g of ammonium formate and then 0.15 g of 10% palladium-on-charcoal are added to 30 ml of ethanol. The mixture is stirred at AT for 3 hours. The catalyst is filtered off and the filtrate is concentrated to dryness. After crystallizing from acetone, 0.985 g of the expected compound is obtained.

EXAMPLES

Example 1

1-({5-(2,4-Dichlorophenyl)-4-[4-(3-hydroxypropoxy)phenyl]thien-2-yl}carbonyl)-4-phenylpiperidine-4-carboxamide 1A) 1-(2,4-Dichlorophenyl)-2-(4-methoxyphenyl)ethanone 367 ml of NaHMDS (2M in THF) are added to 250 ml of THF and the mixture is cooled to −70° C. 54 g of (4-methoxyphenyl)acetic acid are then added; the mixture is left stirring for 2 hours and then 49 g of methyl 2,4-dichlorobenzoate are added. The reaction mixture is allowed to return to 10° C. and poured onto 2 liters of ice-cold HCl (2N), and the product is extracted with ether. After drying with a saturated sodium bicarbonate solution and then a saturated NaCl solution, drying the organic phase and evaporating, the product crystallizes from heptane; 32 g of the expected compound are obtained.

1B) (2E)-1-(2,4-Dichlorophenyl)-3-(dimethylamino)-2-(4-methoxyphenyl)prop-2-en-1-one 15 g of the compound obtained in 1A) and 33.76 ml of 1,1-dimethoxy-N,N-dimethylmethanamine are added to 100 ml of THF and the mixture is heated at 80° C. overnight. After evaporating the reaction mixture to dryness, water is added and extraction is carried out with ether. The extract is dried and evaporated. After purifying by chromatography on silica (eluent: heptane-AcOEt (gradient from 0% to 30%)), 18 g of the expected compound are obtained.

1C) (2E)-3-Chloro-3-(2,4-dichlorophenyl)-2-(4-methoxyphenyl)acryl aldehyde 18 g of the compound obtained in 1B) and 12 ml of POCl$_3$ are added to 100 ml of CH$_2$Cl$_2$ and the mixture is heated at 45° C. for 3 hours. After leaving overnight at AT, the mixture is evaporated to dryness, the residue is taken off in THF and then 50 ml of water are added. Extraction is carried out with ether and the extract is washed with water and then with a saturated aqueous sodium bicarbonate solution. After drying over MgSO$_4$ and then concentrating to dryness, 15.5 g of the expected compound are obtained.

1 D) Methyl 5-(2,4-dichlorophenyl)-4-(4-methoxyphenyl)thiophene-2-carboxylate 11 g of the compound obtained in 1C) and 7.2 ml of methyl mercaptoacetate are mixed in 80 ml of acetonitrile. The mixture is heated to 60° C. and DBU is added. The temperature of the reaction medium is maintained at 60° C. and the temperature is brought back to AT overnight. The mixture is evaporated to dryness, a 1N HCl solution is added and the compound is extracted with ethyl acetate. The organic phase is dried and evaporated. After purifying by chromatography on silica (eluent: heptane-AcOEt (gradient from 0% to 30%)), 6.3 g of the expected compound are obtained.

1E) 5-(2,4-Dichlorophenyl)-4-(4-methoxyphenyl)thiophene-2-carboxylic acid 7.2 g of the compound obtained in stage 1D) and 1.83 g of NaOH are added to a 50-50 dioxane-methanol mixture. The reaction mixture is heated at 50° C. overnight. It is evaporated to dryness, distilled water is added and the organic residues are extracted with ether. The aqueous phase is acidified with concentrated HCl and then the acid is extracted with ether. The organic phase is dried and then evaporated. 5.6 g of the expected compound are obtained.

1F) 1-{[5-(2,4-Dichlorophenyl)-4-(4-methoxyphenyl)thien-2-yl]carbonyl}-4-phenylpiperidine-4-carboxamide 2 g of the compound obtained in stage 1E), 1.27 g of 4-phenylpiperidine-4-carboxamide (Preparation 2), 2.22 ml of Et$_3$N and 1.86 g of TBTU are added to 40 ml of CH$_2$Cl$_2$. The mixture is stirred at AT for 3 hours. It is evaporated to dryness, water is added and extraction is carried out with ethyl acetate. The organic phase is dried and then evaporated. After purifying by chromatography on silica (eluent: heptane-AcOEt (gradient from 0% to 30%)), 2.8 g of the expected compound are obtained.

1G) 1-{[5-(2,4-Dichlorophenyl)-4-(4-hydroxyphenyl)thien-2-yl]carbonyl}-4-phenylpiperidine-4-carboxamide 2.8 g of the compound obtained in stage 1F) and 19.8 ml of a 1M solution of BBr$_3$ in CH$_2$Cl$_2$ are added to 70 ml of CH$_2$Cl$_2$ at the temperature of melting ice. The temperature is allowed to rise to AT while continuing to stir over 3 hours. The reaction medium is subsequently poured onto water and the organic phase is recovered and subsequently dried and then evaporated. After crystallizing from an ether-ethyl acetate mixture, 1.8 g of the expected compound are obtained.

1H) 1-({5-(2,4-Dichlorophenyl)-4-[4-(3-hydroxypropoxy)phenyl]thien-2-yl}carbonyl)-4-phenylpiperidine-4-carboxamide 1.65 g of the compound obtained in stage 1G), 0.57 g of K$_2$CO$_3$ and 0.83 g of 3-chloropropan-1-ol are added to 10 ml of DMF. The reaction medium is heated at 90° C. for 3 hours. The reaction medium is then poured onto distilled water and the expected compound is extracted with ethyl acetate. The organic phase is dried and evaporated. After crystallizing in ethyl acetate, 1.2 g of the expected compound are obtained.

Example 2

1-{[5-(2,4-Dichlorophenyl)-4-(4-{3-[(methylsulphonyl)amino]-propoxy}phenyl)thien-2-yl]carbonyl}-4-phenylpiperidine-4-carboxamide 2A) 3-(4-{5-[(4-Carbamoyl-4-phenylpiperidin-1-yl)carbonyl]dichlorophenyl)thien-3-yl}phenoxy)propyl methanesulphonate 0.07 ml of MsCl and then 0.02 ml of Et$_3$N are added to 1.5 g of the compound obtained in stage 1H) placed in 10 ml of CH$_2$Cl$_2$. The mixture is left stirring for 1 hour, It is evaporated to dryness, a 0.1N HCl solution is added and the expected compound is extracted with ethyl acetate. After drying and evaporating, 0.15 g of the expected compound is obtained.

2B) 1-{[5-(2,4-Dichlorophenyl)-4-(4-{3-[(methylsulphonyl)amino]propoxy}-phenyl)thien-2-yl]carbonyl}-4-phenylpiperidine-4-carboxamide 0.029 g of methanesulphonamide and 0.016 g of sodium hydride are added to 5 ml of DMF and then the mixture is stirred for 5 minutes. 0.14 g of the compound obtained in stage 2A), dissolved in 2 ml of DMF, is then added and the mixture is stirred for 2 hours. The reaction medium is poured onto water and extraction is carried out with ethyl acetate. The extract is dried and evaporated. After purifying by chromatography on silica (eluent: $CH_2Cl_2$-MeOH (gradient from 0% to 3%), 0.035 g of the expected compound is obtained.

Example 3

1-({5-(2,4-Dichlorophenyl)-4-[4-(3-(pyrrolidin-1-yl) propoxy)phenyl]thien-2-yl}carbonyl)-4-phenylpiperidine-4-carboxamide 0.12 ml of pyrrolidine is added to 0.2 g of the compound obtained in stage 2A) in 5 ml of DMF and then the mixture is heated to 70° C. for 2 hours. The reaction medium is poured onto distilled water and the compound is extracted with ethyl acetate. The extract is dried and evaporated. After washing with ether and filtering, 0.1 g of the expected compound is obtained.

Example 4

1-({4-(2,4-Dichlorophenyl)-5-[4-(3-hydroxypropoxy)phenyl]thien-2-yl}carbonyl)-4-phenylpiperidine-4-carboxamide 4A) 1-{[4-(2,4-Dichlorophenyl)-5-(4-methoxyphenyl)thien-2-yl]carbonyl}-4-phenylpiperidine-4-carboxamide 4-(2,4-dichlorophenyl)-5-(4-methoxyphenyethiophene-2-carboxylic acid is prepared, according to the procedure used in stages 1A)-1E), from (2,4-dichlorophenyl)acetic acid and methyl 4-methoxybenzoate. 3.8 g of 4-(2,4-dichlorophenyl)-5-(4-methoxyphenyl)thiophene-2-carboxylic acid, 2.53 g of 4-phenylpiperidine-4-carboxamide (preparation 2), 0.72 ml of $Et_3N$ and 3.53 g of TBTU are added at AT to 100 ml of $CH_2Cl_2$. The mixture is stirred overnight. It is evaporated to dryness, water is added and the compound obtained is extracted with ethyl acetate. The organic phase is dried and evaporated to dryness. After crystallizing, washing with ethyl ether, filtering and then drying, 5.1 g of the expected compound are obtained.

4B) 1-{[4-(2,4-Dichlorophenyl)-5-(4-hydroxyphenyl)thien-2-yl]carbonyl}-4-phenylpiperidine-4-carboxamide 5 g of the compound resulting from stage 4A) and then 35.37 ml of a 1M solution of $BBr_3$ in $CH_2Cl_2$ are added to 100 ml of $CH_2Cl_2$ at the temperature of melting ice. The temperature of the reaction medium is allowed to return to AT overnight. The reaction medium is subsequently poured onto distilled water and the compound obtained is extracted with $CH_2Cl_2$. The organic phase is dried and evaporated. After crystallizing from ethyl ether, 3.1 g of the expected compound are obtained.

4C) 1-({4-(2,4-Dichlorophenyl)-5-[4-(3-hydroxypropoxy)phenyl]thien-2-yl}carbonyl)-4-phenylpiperidine-4-carboxamide 1 g of the compound obtained in stage 4B), 0.376 g of potassium carbonate and 0.223 g of 3-chloropropan-1-ol are added to 6 ml of DMF. The reaction medium is heated at 110° C. for 3 hours. The reaction medium is subsequently poured onto distilled water and the compound obtained is extracted with ethyl acetate. The organic phase is dried and evaporated. After purifying by chromatography on silica (eluent: $CH_2Cl_2$-MeOH (gradient from 0% to 4%)), 0.6 g of the expected compound is obtained.

Example 5

1-({5-[4-(3-Aminopropoxy)phenyl]-4-(2,4-dichlorophenyl)thien-2-yl}carbonyl)-4-phenylpiperidine-4-carboxamide hydrochloride 5A) tert-Butyl[3-(4-{5-[(4-carbamoyl-4-phenylpiperidin-1-yl)carbonyl]dichlorophenyl)thien-2-yl}phenoxy)propyl]carbamate 1 g of the compound obtained in stage 4B), 0.504 g of potassium carbonate and 0.868 g of tert-butyl (3-bromopropyl)carbamate are added to 60 ml of acetone and then the reaction medium is heated at reflux for 4 hours. The insoluble materials are filtered off and the filtrate is evaporated to dryness. After purifying by chromatography on silica (eluent: $CH_2Cl_2$-MeOH (gradient from 0% to 7%)), 0.6 g of the expected compound is obtained.

5B) 1-({5-[4-(3-Aminopropoxy)phenyl]-4-(2,4-dichlorophenyl)thien-2-yl}carbonyl)-4-phenylpiperidine-4-carboxamide hydrochloride 0.4 g of the compound obtained in 5A) and 1.28 g of TFA are added to 5 ml of $CH_2Cl_2$ and the mixture is left stirring at AT for 1 hour. It is evaporated to dryness, a 1N sodium hydroxide solution is added and the compound is extracted with $CH_2Cl_2$. The organic phase is dried before adding ethereal hydrochloric acid in order to form the salt. After evaporating to dryness and drying under vacuum, 0.28 g of the expected compound is obtained.

Example 6

1-{[4-(2,4-Dichlorophenyl)-5-(4-{3-[(methylsulphonyl)amino]-propoxy}phenyl)thien-2-yl]carbonyl}-4-phenylpiperidine-4-carboxamide 0.19 g of the compound obtained in 5B), 0.063 ml of $Et_3N$ and then 0.03 ml of MsCl are added to 10 ml of $CH_2Cl_2$ and the mixture is left stirring for 2 hours. It is evaporated to dryness, a sodium hydroxide solution is added and then the compound is extracted with $CH_2Cl_2$. The extract is dried and evaporated. After purifying by chromatography on silica (eluent: $CH_2Cl_2$-MeOH (gradient from 0% to 5%)), 0.085 g of the expected compound is obtained.

Example 7

1-{[4-(2,4-Dichlorophenyl)-5-{4-[3-(methylthio)propoxy]phenyl}-thien-2-yl]carbonyl}-4-phenylpiperidine-4-carboxamide 7A) 3-(4-{5-[(4-Carbamoyl-4-phenylpiperidin-1-yl)carbonyl]-3-(2,4-dichlorophenyl)thien-2-yl}phenoxy)propyl methanesulphonate 0.8 g of the compound obtained in 4C), 0.37 ml of $Et_3N$ and 0.12 ml of MsCl are added to 20 ml of $CH_2Cl_2$ at AT and then the mixture is left stirring for 1 hour. It is evaporated to dryness, a 0.1N HCl solution is added and the compound is extracted with ethyl acetate. After drying and evaporating, 0.79 g of the expected compound is obtained.

7B) 1-{[4-(2,4-Dichlorophenyl)-5-{4-[3-(methylthio)propoxy]phenyl}thien-2-yl]carbonyl}-4-phenylpiperidine-4-carboxamide 0.79 g of the compound obtained in 7A) and 0.097 g of sodium thiomethoxide are added to 4 ml of DMF and then the mixture is left stirring for 4 hours at AT. The reaction mixture is subsequently poured onto distilled water and the compound is extracted with ethyl acetate. The extract is dried and evaporated. After purifying by chromatography on silica (eluent: $CH_2Cl_2$-MeOH (gradient from 0% to 5%)), 0.55 g of the expected compound is obtained.

Example 8

1-{[4-(2,4-Dichlorophenyl)-5-{4-[3-(methyl sulphonyl)propoxy]phenyl}thien-2-yl]carbonyl}-4-phenylpiperidine-4-carboxamide 0.27 g of the compound obtained in 7B) and 0.26 g of 70% MCPBA are added to 20 ml of $CH_2Cl_2$ at AT and then the mixture is left stirring overnight. A 10% $Na_2CO_3$ solution is then added and the mixture is stirred vigorously for 30 minutes. The organic phase is separated, dried and evaporated. After purifying by chromatography on silica (eluent: $CH_2Cl_2$-MeOH (gradient from 0% to 4%)), 0.07 g of the expected compound is obtained.

Example 9

1-{[5-(2,4-Dichlorophenyl)-4-{4-[(4-hydroxybutyl)thio]phenyl}thien-2-yl]carbonyl}-4-phenylpiperidine-4-carboxamide 9A) 1-{[4-(4-Bromophenyl)-5-(2,4-dichlorophenylthien-2-yl]carbonyl}-4-phenylpiperidine-4-carboxamide 4-(4-Bromophenyl)-5-(2,4-dichlorophenyl)thiophene-2-carboxylic acid is prepared, according to the procedure used in stages 1A)-1E), from (4-bromophenyl)acetic acid and methyl 2,4-dichlorobenzoate. 7 g of 4-(4-bromophenyl)-5-(2,4-dichlorophenyl)thiophene-2-carboxylic acid, 3.94 g of 4-phenylpiperidine-4-carboxamide hydrochloride (preparation 2), 6.83 ml of $Et_3N$ and 5.77 g of TBTU are added at AT to 100 ml of $CH_2Cl_2$ and then the mixture is stirred overnight. It is evaporated to dryness, water is added and the expected compound is extracted with ethyl acetate. The organic phase is dried with $MgSO_4$, filtered and evaporated to dryness. After crystallizing, washing with ethyl ether, filtering and drying, 8.41 g of the expected compound are obtained.

9B) 1-{[5-(2,4-Dichlorophenyl)-4-{4-[(4-hydroxybutyl)thio]phenyl}thien-2-yl]carbonyl}-4-phenylpiperidine-4-carboxamide 0.455 g of 4-mercaptobutan-1-ol and 0.072 g of sodium hydride are added to 25 ml of xylene, degassed beforehand with argon for 15 minutes, at 0° C. and then the reaction mixture is left stirring for 1 hour while allowing to return to AT. 1 g of the compound obtained in 9A), 0.119 g of $Pd_2$(dba)$_3$ and 0.087 g of Xantphos are then added. The reaction medium is subsequently heated at 150° C. over night. The reaction medium is evaporated to dryness, water and ethyl acetate are added, the insoluble material is filtered off, the organic phase is washed with water and the organic phase is dried, filtered and concentrated. After purifying by chromatography on silica (eluent: $CH_2Cl_2$-MeOH (gradient from 0% to 3%)), 0.35 g of the expected compound is obtained.

Example 10

1-{[5-(2,4-Dichlorophenyl)-4-{4-[(4-hydroxybutyl)sulphinyl]phenyl}thien-2-yl]carbonyl}-4-phenylpiperidine-4-carboxamide 0.23 g of the compound obtained in 9B) and 0.109 g of 70% MCPRA are added to 20 ml of $CH_2Cl_2$ at AT and then the mixture is left stirring overnight. A 10% $Na_2CO_3$ solution is then added and the mixture is subsequently stirred for 15 minutes. The organic phase is separated, dried and evaporated. After purifying by chromatography on silica (eluent: $CH_2Cl_2$-MeOH (gradient from 0% to 4%)), 0.14 g of the expected compound is obtained.

Example 11

1-{[5-(2,4-Dichlorophenyl)-4-{4-[4-hydroxybutyl)sulphonyl]phenyl}thien-2-yl]carbonyl}-4-phenylpiperidine-4-carboxamide 0.16 g of the compound obtained in Example 10 and 0.121 g of 70% MCPBA are added to 20 ml of $CH_2Cl_2$ at AT and then the mixture is left stirring overnight. A 10% $Na_2CO_3$ solution is then added and the mixture is subsequently stirred for 15 minutes. The organic phase is separated, dried and evaporated. After purifying by chromatography on silica (eluent: $CH_7Cl_2$-MeOH (gradient from 0% to 4%)), 0.05 g of the expected compound is obtained.

Example 12

4-{5-[(4-Carbamoyl-4-phenylpiperidin-1-yl)carbonyl]-2-(2-chlorophenyl)thien-3-yl}phenylpropane-1-sulphonate 12A) 5-(2-Chlorophenyl)-4-(4-methoxyphenyl)thiophene-2-carboxylic acid 5-(2-Chlorophenyl)-4-(4-methoxyphenyl)thiophene-2-carboxylic acid is prepared, according to the procedure used in stages 1A)-1E), from (4-methoxyphenyl)acetic acid and methyl 2-chlorobenzoate. In the final stage of this procedure, 5 g of methyl 542-chlorophenyl)-4-(4-methoxyphenyl)-2-thiophenecarboxylate and 1.11 g of sodium hydroxide pellets are added to 30 ml of methanol and 3 ml of dioxane. The reaction medium is heated at 50-60° C. for 5 hours. It is evaporated to dryness, water is added and the impurities are extracted with ether. The aqueous phase is acidified and the expected compound is extracted with ether. After drying and evaporating, 3.5 g of the expected compound are obtained.

12B) 1-{[5-(2-Chlorophenyl)-4-(4-methoxyphenyl)thien-2-yl]carbonyl}-4-phenylpiperidine-4-carboxamide 1.5 g of the compound obtained in 12A), 1.047 g of 4-phenylpiperidine-4-carboxamide hydrochloride, 1.83 ml of $Et_3N$ and 1.56 g of TBTU are added at AT to 100 ml of $CH_2Cl_2$ and then the mixture is stirred overnight. It is evaporated to dryness, water is added and the expected compound is extracted with ethyl acetate. The organic phase is dried, filtered and evaporated to dryness. The compound which is crystallized is washed with ethyl ether and then filtered off and dried. 2 g of the expected compound are obtained.

12C) 1-{[5-(2-Chlorophenyl)-4-(4-hydroxyphenyl)thien-2-yl]carbonyl}-4-phenylpiperidine-4-carboxamide 1.7 g of the compound obtained in stage 12B) and then 12.8 ml of a 1M solution of $BBr_3$ in $CH_2Cl_2$ are added to 50 ml of $CH_2Cl_2$ at the temperature of melting ice and the temperature of the reaction medium is allowed to return to AT overnight. The reaction medium is subsequently poured onto distilled water and the expected compound is extracted with $CH_2Cl_2$. The organic phase is dried and evaporated. The compound crystallizes from ethyl ether. 1.2 g of the expected compound are obtained.

12D) 4-{5-[(4-Carbamoyl-4-phenylpiperidin-1-yl)carbonyl]-2-(2-chlorophenyl)thien-3-yl}phenylpropane-1-sulphonate 0.3 g of the compound obtained in 12C), 0.29 ml of $Et_3N$ and then 0.207 g of propane-1-sulphonyl chloride are added at AT to 30 ml of $CH_2Cl_2$. After 3 hours, the reaction medium is poured onto distilled water and the compound is extracted. After drying, evaporating and then washing with ether, 0.13 g of the expected compound is obtained.

Example 13

4-{5-[(4-Carbamoyl-4-phenylpiperidin-1-yl)carbonyl]-2-(2-chlorophenyl)thien-3-yl}phenyl 3,3,3-trifluoropropane-1-sulphonate 0.3 g of the compound obtained in stage 12C), 0.29 ml of $Et_3N$ and then 0.28 g of 3,3,3-trifluoropropane-1-sulphonyl chloride are added to 30 ml of $CH_2Cl_2$ at AT. After 3 hours, the mixture is evaporated to dryness. Water and ethyl acetate are added and then the combined mixture is stirred. After filtering, rinsing with ether and then drying, 0.13 g of the expected compound is obtained.

Example 14

1-{[5-(2,4-Dichlorophenyl)-4-{4-[(4,4,4-trifluorobutyl)thio]phenyl}thien-2-yl]carbonyl}-4-phenylpiperidine-4-carboxamide 0.455 g of 4,4,4-trifluorobutane-1-thiol and 0.072 g of sodium hydride are added to 25 ml of xylene, degassed beforehand with argon for 15 minutes, at 0° C. and then the mixture is left stirring for 1 hour while allowing to return to AT. 1 g of the compound obtained in 9A), 0.119 g of $Pd_2(dba)_3$ and 0.087 g of Xantphos are then added. The reaction medium is subsequently heated at 150° C. overnight. The reaction medium is evaporated to dryness, water and ethyl acetate are added, the insoluble material is filtered off, the organic phase is washed with water and the organic phase is dried, filtered and concentrated. After purifying by chromatography on silica (eluent: $CH_2Cl_2$-MeOH (gradient from 0% to 4%)), 0.16 g of the expected compound is obtained.

Example 15

1-{[5-(2,4-Dichlorophenyl)-4-{4-[(4,4,4-trifluorobutyl)sulphonyl]phenyl}thien-2-yl]carbonyl}-4-phenylpiperidine-4-carboxamide 0.36 g of the compound obtained in Example 14 and 0.385 g of 70% MCPBA are added to 20 ml of $CH_2Cl_2$ at AT and then the mixture is left stirring overnight. A 10% $Na_2CO_3$ solution is then added and the mixture is stirred vigorously for 30 minutes. The organic phase is separated, dried and evaporated. After purifying by chromatography on silica (eluent: $CH_2Cl_2$-MeOH (gradient from 0% to 4%)), 0.19 g of the expected compound is obtained.

Example 16

1-({5-(2-Chloro-4-fluorophenyl)-4-[4-(3-hydroxypropoxy)phenyl]thien-2-yl}carbonyl)-4-phenylpiperidine-4-carboxamide

16A) 1-(2-Chloro-4-fluorophenyl)-2-(4-methoxyphenyl)ethanone 230 ml of a 2M solution of NaHMDS in THF are introduced into 250 ml of THF under nitrogen. The solution is cooled to −60° C. and then 30.5 g of (4-methoxyphenyl)acetic acid in 120 ml of THF are added at this temperature. After 1 h 30 min at −60° C., 33 g of methyl 2-chloro-4-fluorobenzoate are added and the mixture is stirred at −60° C. for 45 min and then allowed to return to 0° C. The reaction medium is poured onto 500 ml of ice-cold 2N HCl and extracted with ether and the extract is washed with water and then with a saturated aqueous sodium chloride solution. After drying, concentrating to dryness and then crystallizing from pentane, 27.4 g of the expected compound are obtained.

16B) (2E)-1-(2-Chloro-4-fluorophenyl)-3-(dimethylamino)-2-(4-methoxyphenyl)prop-2-en-1-one 27.4 g of the compound obtained in 16A) and 35 g of 1,1-dimethoxy-N,N-dimethylmethanamine are added to 100 ml of THF and the mixture is brought to reflux for 3 hours. After concentrating to dryness and then crystallizing from isopropyl ether, 24.7 g of the expected compound are obtained.

16C) (2E)-3-Chloro-3-(2-chloro-4-fluorophenyl)-2-(4-methoxyphenyl)acrylaldehyde 24.7 g of the compound obtained in stage 16B) and then 17.3 g of $POCl_3$ are added to 200 ml of $CH_2Cl_2$. The mixture is heated at 45° C. overnight and is then concentrated to dryness. The residue is taken up in THF and then 50 ml of water are added. Extraction is carried out with ether and the extract is washed with water and with a saturated aqueous sodium chloride solution. After drying and concentrating to dryness, 24 g of the expected compound are obtained.

16D) Methyl 5-(2-chloro-4-fluorophenyl)-4-(4-methoxyphenyl)thiophene-2-carboxylate 24 g of the compound obtained in 16C) and then 16.5 ml of methyl mercaptoacetate are added to 240 ml of acetonitrile. The mixture is heated to 60° C. and 12 ml of DBU are added. The mixture is maintained at 60° C. for 2 hours and then at AT overnight. It is concentrated to dryness and the residue is taken up in ethyl acetate and washed with 1N HCl and then with water. After drying, concentrating to dryness and then crystallizing from methanol, 20.6 g of the expected compound are obtained.

16E) Methyl 5-(2-chloro-4-fluorophenyl)-4-(4-hydroxyphenyl)thiophene-2-carboxylate The compound obtained in stage 16D) is added to 100 ml of $CH_2Cl_2$, cooling is carried out to −50° C. and 40 ml of a 1M solution of $BBr_3$ in $CH_2Cl_2$ are added. The temperature is allowed to return to 20° C. and then 20 ml of methanol are added. The mixture is concentrated to dryness and the residue is taken up in $CH_2Cl_2$, washed with water, $MgSO_4$ and concentrated to dryness. After purifying by chromatography on silica (heptane up to heptane/AcOEt 75/25), 4.8 g of the expected compound are obtained.

16F) Methyl 5-(2-chloro-4-fluorophenyl)-4-{4-[3-(tetrahydro-2H-pyran-2-yloxy)propoxy]phenyl}thiophene-2-carboxylate 4.8 g of the compound obtained in stage 16E), 3.6 g of 2-(3-bromopropoxy)tetrahydro-2H-pyran and 2.2 g of potassium carbonate are added to 30 ml of DMF and then the mixture is heated at 60° C. for 7 hours. It is poured onto ice-cold water, extraction is carried out with ether and the extract is dried and concentrated to dryness. After purifying by chromatography on silica (heptane and then heptane/AcOEt: 90/10), 6.2 g of the expected compound are obtained.

16G) 5-(2-Chloro-4-fluorophenyl)-4-{4-[3-(tetrahydro-2H-pyran-2-yloxy)propoxy]phenyl}thiophene-2-carboxylic acid 3.1 g of the compound obtained in stage 16F) and then 800 mg of sodium hydroxide pellets are added to 30 ml of methanol and 1 ml of water. The reaction mixture is brought to reflux for 2 hours. It is concentrated to dryness, the residue is taken up in 500 ml of buffer solution at pH 2, extraction is carried out with ether and the extract is dried and concentrated to dryness. 3 g of the expected compound, crystallized from pentane, are obtained.

16H) 1-{[5-(2-Chloro-4-fluorophenyl)-4-{4-[3-(tetrahydro-2H-pyran-2-yl oxy)prop oxy]phenyl}thien-2-yl]carbonyl}-4-phenylpiperidine-4-carboxamide 0.5 g of the compound obtained in stage 16G), 0.25 g of 4-phenylpiperidine-4-carboxamide hydrochloride, 0.43 ml of $Et_3N$ and 0.36 g of TBTU are added to 10 ml of $CH_2Cl_2$ and then reaction is allowed to take place at AT for 2 hours. After concentrating to dryness, taking up the residue in a water/ether mixture and filtering, 0.6 g of the expected compound is obtained.

16I) 1-({5-(2-Chloro-4-fluorophenyl)-4-[4-(3-hydroxypropoxy)phenyl]thien-2-yl}carbonyl)-4-phenylpiperidine-4-carboxamide 0.6 g of the compound obtained in stage 16H) and 2 ml of 2N etheral hydrochloric acid are added to 15 ml of methanol. After 2 hours at AT, the expected compound is filtered off. 0.385 g of the expected compound is obtained.

Example 17

1'-({5-(2-Chloro-4-fluorophenyl)-4-[4-(3-hydroxypropoxy)phenyl]-2-thienyl}carbonyl)-4,4-difluoro-1,4'-bipiperidine-4'-carboxamide hydrochloride

17A) 1'-{[5-(2-Chloro-4-fluorophenyl)-4-{4-[3-(tetrahydro-2H-pyran-2-yloxy)propoxy]phenyl}thien-2-yl]carbonyl}-4,4-difluoro-1,4'-bipiperidine-4'-carboxamide 0.5 g of the compound obtained in stage 16G), 0.33 g of 4,4-difluoro-1,4'-bipiperidine-4'-carboxamide (described in Preparation 5, page 23, of Application WO 2008/068423), 0.57 ml of $Et_3N$ and 0.36 g of TBTU are added to 10 ml of $CH_2Cl_2$. After 2 hours at AT, concentrating to dryness, taking up the residue in a water/ether mixture and filtering, 0.63 g of the expected compound is obtained.

17B) 1'-({5-(2-Chloro-4-fluorophenyl)-4-[4-(3-hydroxypropoxy)phenyl]thien-2-yl}carbonyl)-4,4-difluoro-1,4'-bipiperidine-4'-carboxamide hydrochloride.

0.63 g of the compound obtained in stage 17A) and 2 ml of 2N ethereal hydrochloric acid are added to 15 ml of methanol. After 1 hour at AT, concentrating to dryness and then crystallizing from AcOEt, 0.612 g of the expected compound is obtained.

Example 18

1-({5-(2-Chloro-4-fluorophenyl)-4-[4-(3-hydroxypropoxy)phenyl]thien-2-yl}carbonyl)-4-[(3,3,3-trifluoropropyl)amino]piperidine-4-carboxamide hydrochloride

18A) 1-{[5-(2-Chloro-4-fluorophenyl)-4-{4-[3-(tetrahydro-2H-pyran-2-yloxy)propoxy]phenyl}thien-2-yl]carbonyl}-4-[(3,3,3-trifluoropropyl)amino]piperidine-4-carboxamide 0.5 g of the compound obtained in stage 16G), 0.41 g of 4-(3,3,3-trifluoropropylamino)piperidine-4-carboxamide (Preparation 1), 0.71 ml of $Et_3N$ and 0.36 g of TBTU are added to 10 ml of $CH_2Cl_2$. After 3 hours at AT, the mixture is concentrated to dryness and the residue is taken up in ether, washed with water, dried and concentrated to dryness. After purifying by chromatography on silica (elution gradient: heptane/AcOEt 90/10 up to pure AcOEt). 0.7 g of the expected compound is obtained.

18B) 1-({5-(2-Chloro-4-fluorophenyl)-4-[4-(3-hydroxypropoxy)phenyl]thien-2-yl}carbonyl)-4-[(3,3,3-trifluoropropyl)amino]piperidine-4-carboxamide hydrochloride 0.7 g of the compound obtained in stage 18A) and 3 ml of 2N ethereal hydrochloric acid are added to 15 ml of methanol. After 2 hours at AT, concentrating to dryness, taking up the residue in ether and then filtering, 0.57 g of the expected compound is obtained.

Example 19

1-{[5-(2-Chloro-4-fluorophenyl)-4-{4-[3-(methylthio)propoxy]phenyl}thien-2-yl]carbonyl-}4-phenylpiperidine-4-carboxamide

19A) Methyl 5-(2-chloro-4-fluorophenyl)-4-[4-(3-hydroxypropoxy)phenyl]thiophene-2-carboxylate 3.1 g of the compound obtained in stage 16F) and 1 ml of Amberlyst 15 resin are added to 40 ml of methanol. The mixture is brought to reflux for 2 hours, the resin is filtered off and the filtrate is concentrated to dryness. The residue is taken up in ether, washed with water, dried and then concentrated to dryness. After purifying by chromatography on silica (elution gradient: heptane up to heptane/AcOEt 60/40), 2.0 g of the expected compound are obtained.

19B) Methyl 5-(2-chloro-4-fluorophenyl)-4-(4-{3-[(methylsulphonyl)oxy]propoxy}phenyl)thiophene-2-carboxylate 2 g of the compound obtained in 19A) and then 0.79 ml of Et₃N are added to 40 ml of CH₂Cl₂. The mixture is cooled to 0° C. and then 0.44 ml of MsCl is added. After 15 minutes, washing is carried out with water and the organic phase is dried and concentrated to dryness. 2.38 g of the expected compound are obtained.

19C) Methyl 5-(2-chloro-4-fluorophenyl)-4-{-4-[3-(methylthio)propoxy]phenyl}thiophene-2-carboxylate 2.38 g of the compound obtained in 19B) and 0.83 g of sodium thiomethoxide are added to 12 ml of DMF and the mixture is stirred at AT for 2 hours. The mixture is poured onto water, extraction is carried out with ether and the extract is washed with HCl, diluted in water, dried and concentrated to dryness. After purifying by chromatography on silica (elution gradient: heptane up to heptane/AcOEt 93/7), 1.68 g of the expected compound are obtained.

19D) 5-(2-Chloro-4-fluorophenyl)-4-{4-[3-(methylthio)propoxy]phenyl}thiophene-2-carboxylic acid.

1.68 g of the compound obtained in 19C) and then 0.45 g of NaOH are added to 20 ml of MeOH and 1 ml of water. The mixture is brought to reflux for 2 hours and then concentrated to dryness. The residue is taken up in water, acidification is carried out with 2N HCl, extraction is carried out with ether and the extract is dried and concentrated to dryness. 1.51 g of the expected compound are obtained.

19E) 1-{[5-(2-Chloro-4-fluorophenyl)-4-{4-[3-(methylthio)propoxy]phenyl}thien-2-yl]carbonyl}-4-phenylpiperidine-4-carboxamide 0.5 g of the compound obtained in 19D), 0.28 g of 4-phenylpiperidine-4-carboxamide hydrochloride (Preparation 2), 0.48 ml of Et₃N and 0.405 g of TBTU are added to 10 ml of CH₂Cl₂. After 2 hours at AT, the mixture is concentrated to dryness, the residue taken up in a water/ether mixture and filtration is carried out. 0.635 g of the expected compound is obtained.

Example 20

1-{[5-(2-Chloro-4-fluorophenyl)-4-{4-[3-(methylsulphonyl)propoxy]phenyl}thien-2-yl]carbonyl}-4-phenylpiperidine-4-carboxamide 0.43 g of the compound obtained in stage 19E) and 0.425 g of MCPBA are added to 10 ml of CH₂Cl₂ and the mixture is stirred at AT for 3 hours. It is washed with an aqueous sodium bicarbonate solution, dried and concentrated to dryness. After purifying by chromatography on silica (elution gradient: CH₂Cl₂ up to CH₂Cl₂/MeOH 98/2), 0.216 g of the expected compound is obtained.

Example 21

1'-{[5-(2-Chloro-4-fluorophenyl)-4-{-4-[3-(methylthio)propoxy]phenyl}thien-2-yl]carbonyl}-4,4-difluoro-1,4'-bipiperidine-4'-carboxamide hydrochloride 0.5 g of the compound obtained in stage 19D), 0.51 g of 4,4-difluoro-1,4'-bipiperidine-4'-carboxamide (described in Preparation 5, page 23, of Application WO 2008/068423), 0.8 ml of Et₃N and 0.405 g of TBTU are added to 10 ml of CH₂Cl₂. After 3 hours at AT, the mixture is concentrated to dryness, taken up in ether, washed with water, dried and concentrated to dryness. After purifying by chromatography on silica (elution gradient: CH₂Cl₂ up to CH₂Cl₂/MeOH 98/2), the compound obtained is dissolved in CH₂Cl₂, ethereal hydrochloric acid is added down to a pH of 1 and then the mixture is concentrated to dryness. After taking up the residue in ether and filtering, 0.723 g of the expected compound is obtained.

Example 22

1'-{[5-(2-Chloro-4-fluorophenyl)-4-{4-[3-(methylsulphonyl)propoxy]phenyl}thien-2-yl]carbonyl}-4,4-difluoro-1,4'-bipiperidine-4'-carboxamide hydrochloride 22A) 5-(2-Chloro-4-fluorophenyl)-4-{4-[3-(methylsulphonyl)propoxy]phenyl}thiophene-2-carboxylic acid 0.5 g of the compound obtained in stage 19D) and 0.62 g of MCPBA are added to 15 ml of CH₂Cl₂ and then the mixture is stirred at AT for 4 hours. After concentrating, filtering and rinsing with isopropyl ether, 0.585 g of the expected compound is obtained.

22B) 1'-{[5-(2-Chloro-4-fluorophenyl)-4-{-4-[3-(methylsulphonyl)propoxy]phenyl}thien-2-yl]carbonyl}-4,4-difluoro-1,4'-bipiperidine-4'-carboxamide hydrochloride 0.3 g of the compound obtained in stage 22A), 0.3 g of 4,4-difluoro-1,4'-bipiperidine-4'-carboxamide (described in Preparation 5, page 23, of Application WO 2008/068423), 0.45 ml of Et₃N and 0.25 g of TBTU are added in order to 10 ml of CH₂Cl₂. After 3 hours at AT, the mixture is concentrated to dryness and the residue is taken up in AcOEt, washed with water, dried and concentrated to dryness. After purifying by chromatography on silica (elution gradient: CH₂Cl₂ up to CH₂Cl₂/MeOH 98/2), the compound obtained is dissolved in CH₂Cl₂, ethereal hydrochloric acid is added down to a pH of 1 and then the mixture is concentrated to dryness. 0.28 g of the expected compound is obtained.

Example 23

1-({5-(2-Chlorophenyl)-4-[4-(3-hydroxypropoxy) phenyl]thien-2-yl}carbonyl)-4-phenylpiperidine-4-carboxamide

23A)
1-(2-Chlorophenyl)-2-(4-methoxyphenyl)ethanone 230 ml of a 2M solution of NaHMDS in THF are introduced under nitrogen in a 250 ml of THF. The solution is cooled to −60° C. and then 30.5 g of (4-methoxyphenyl)acetic acid in 120 ml of THF are added at this temperature. After 1 h 30 min at −60° C., 29.8 g of methyl 2-chlorobenzoate are added and the mixture is stirred at −60° C. for 45 min and then allowed to return to 0° C. The reaction medium is poured on to 500 ml of ice-cold 2N HCl, extraction is carried out with ether and the extract is washed with water and then with a saturated aqueous sodium chloride solution. After drying and concentrating to dryness, purification is carried out by chromatography on silica (gradient: heptane up to heptane/AcOEt 80/20). 7.3 g of the expected compound are obtained.

23B) (2E)-1-(2-Chlorophenyl)-3-(dimethylamino)-2-(4-methoxyphenyl)prop-2-en-1-one 7.3 g of the compound obtained in 23A) and 9.5 g of 1,1-dimethoxy-N,N-dimethylmethanamine are added to 25 ml of THF and the mixture is brought to reflux for 3 hours. After concentrating to dryness, purification is carried out by chromatography on silica (gradient: $CH_2Cl_2$ up to $CH_2Cl_2$/AcOEt 80/20). 9.2 g of the expected compound are obtained.

23C) (2E)-3-Chloro-3-(2-chlorophenyl)-2-(4-methoxyphenyl)acrylaldehyde 9.2 g of the compound obtained in stage 23B) and then 6.8 g of $POCl_3$ are added to 75 ml of $CH_2Cl_2$. The mixture is heated at 45° C. overnight and then concentrated to dryness. The residue is taken up in THF and then 20 ml of water are added. Extraction is carried out with ether and the extract is washed with water and then with a saturated aqueous sodium chloride solution. After drying and concentrating to dryness, 9.1 g of the expected compound are obtained.

23D) Methyl 5-(2-chlorophenyl)-4-(4-methoxyphenyl)thiophene-2-carboxylate 9.1 g of the compound obtained in 23C) and then 6.62 ml of methyl mercaptoacetate are added to 90 ml of acetonitrile. The mixture is heated to 60° C. and 4.83 ml of DBU are added. The mixture is maintained at 60° C. for 2 hours and then at AT overnight. It is concentrated to dryness and the residue is taken up in ethyl acetate and washed with 1N HCl and then with water. After drying, concentrating to dryness and then crystallizing from methanol, 7.8 g of the expected compound are obtained.

23E) Methyl 5-(2-chlorophenyl)-4-(4-hydroxyphenyl)thiophene-2-carboxylate 5 g of the compound obtained in stage 23D) are added to 100 ml of $CH_2Cl_2$, cooling is carried out at −50° C. and 41.8 ml of 1M solution of $BBr_3$ in $CH_2Cl_2$ are added. The temperature is allowed to return to 20° C. and then 20 ml of methanol are added. The mixture is concentrated to dryness and the residue is taken up in $CH_2Cl_2$, washed with water, dried over $MgSO_4$ and concentrated to dryness. After purifying by chromatography on silica (heptane up to heptane/AcOEt 75/25), 4.57 g of the expected compound are obtained.

23F) Methyl 5-(2-chlorophenyl)-4-{4-[3-(tetrahydro-2H-pyran-2-yloxy)propoxy]phenyl}thiophene-2-carboxylate 2.3 g of the compound obtained in stage 23E), 1.95 g of 2-(3-bromopropoxy)tetrahydro-2H-pyran and 1.2 g of potassium carbonate are added to 15 ml of DMF and then the mixture is heated at 60° C. for 7 hours. It is poured onto ice-cold water, extraction is carried out with ether and the extract is dried and concentrated to dryness. After purifying by chromatography on silica (heptane and then heptane/AcOEt 80/20), 3.1 g of the expected compound are obtained.

23G) 5-(9-Chlorophenyl)-4-{4-[1-(tetrahydro-2H-pyran-2-yloxy)propoxy]phenyl}thiophene-2-carboxylic acid 3.1 g of the compound obtained in stage 23F) and then 800 mg of sodium hydroxide pellets are added to 30 ml of methanol and 1 ml of water. The reaction mixture is brought to reflux for 2 hours. It is concentrated to dryness, the residue is taken up in 500 ml of buffer solution at pH 2, the extraction is carried out with ether and the extract is dried and concentrated to dryness. 2.8 g of the expected compound, crystallized from the isopropyl ether/pentane mixture, are obtained.

23H) 1-{[5-(2-Chlorophenyl)-4-{4-[3-(tetrahydro-2H-pyran-2-yloxy)propoxy]phenyl}thien-2-yl]carbonyl}-4-phenylpiperidine-4-carboxamide 0.5 g of the compound obtained in stage 23G), 0.26 g of 4-phenylpiperidine-4-carboxamide hydrochloride, 0.44 ml of $Et_3N$ and 0.38 g of TBTU are added to 15 ml of $CH_2Cl_2$ and then the reaction is allowed to take place at AT for 2 hours. After concentrating to dryness, taking up the residue in a water/ether mixture and filtering, 0.45 g of the expected compound is obtained.

23I) 1-({5-(2-Chlorophenyl)-4-[4-(3-hydroxypropoxy)phenyl]thien-2-yl}carbonyl)-4-phenylpiperidine-4-carboxamide 0.45 g of the compound obtained in stage 23H) and 2 ml of 2N ethereal hydrochloric acid are added to 10 ml of methanol. After 2 hours at AT, the expected compound is filtered off 0.26 g of the expected compound is obtained.

The chemical structures of a few compounds according to the invention and their physical properties (analysis by coupled LC/UV/MS: liquid chromatography/UV detection/mass spectrometry) are shown in Tables 1 and 2. These compounds are given in the examples above or are prepared according to procedures similar to those of the compounds given in the examples (Examples 1 to 23).

In Tables 1 and 2, Me represents a methyl group.

TABLE 1

[Structure: thiophene core with 2,4-dichlorophenyl group, C(O)NR₁R₂ carboxamide, and phenyl-Y-A-R₉ substituent]

| Compound | —NR₁R₂ | —Y—A—R₉ | LC/MS characterization (conditions) |
|---|---|---|---|
| 1 | 4-phenyl-1-methylpiperidine-4-carboxamide | —O—(CH₂)₃—OH | MH⁺ = 609, rt = 9.33 (A) |
| 2 | 4-phenyl-1-methylpiperidine-4-carboxamide | —O—(CH₂)₃—NH₂ | MH⁺ = 608, rt = 7.08 (A) |
| 3 | 4-phenyl-1-methylpiperidine-4-carboxamide | —O—(CH₂)₃—NH—SO₂—Me | MH⁺ = 686, rt = 9.41 (A) |
| 4 | 4-phenyl-1-methylpiperidine-4-carboxamide | —O—(CH₂)₃—S—Me | MH⁺ = 639, rt = 11.29 (A) |
| 5 | 4-phenyl-1-methylpiperidine-4-carboxamide | —O—(CH₂)₃—SO₂—Me | MH⁺ = 671, rt = 9.39 (A) |
| 6 | 4-phenyl-1-methylpiperidine-4-carboxamide | —O—(CH₂)₂—OH | MH⁺ = 595, rt = 9.04 (A) |
| 7 | 4-(4,4-difluoropiperidin-1-yl)-1-methylpiperidine-4-carboxamide | —O—(CH₂)₃—OH | MH⁺ = 652, rt = 1.49 (C) |

TABLE 2

[Structure: thiophene core with C(O)NR1R2 at position 2, a 4-(R9-A-Y-)phenyl group at position 3, and a 2-chloro-4-R6-phenyl group at position 5]

| Compound | —NR₁R₂ | —Y—A—R₉ | R₆ | LC/MS characterization (conditions) |
|---|---|---|---|---|
| 8 | 1-methyl-4-phenyl-piperidine-4-carboxamide | —O—(CH₂)₃—OH | Cl | MH⁺ = 609, rt = 9.55 (A) |
| 9 | 1-methyl-4-phenyl-piperidine-4-carboxamide | —O—(CH₂)₃—NH—SO₂—Me | Cl | MH⁺ = 686, rt = 9.68 (A) |
| 10 | 1-methyl-4-phenyl-piperidine-4-carboxamide | —O—(CH₂)₃—N(pyrrolidine) | Cl | MH⁺ = 662, rt = 7.48 (A) |
| 11 | 1-methyl-4-phenyl-piperidine-4-carboxamide | —S—(CH₂)₄—OH | Cl | MH⁺ = 639, rt = 1.79 (C) |
| 12 | 1-methyl-4-phenyl-piperidine-4-carboxamide | —SO—(CH₂)₄—OH | Cl | MH⁺ = 655, rt = 8.15 (B) |
| 13 | 1-methyl-4-phenyl-piperidine-4-carboxamide | —SO₂—(CH₂)₄—OH | Cl | MH⁺ = 671, rt = 1.53 (C) |
| 14 | 1-methyl-4-phenyl-piperidine-4-carboxamide | —O—SO₂—(CH₂)₂—CH₃ | H | MH⁺ = 623, rt = 9.93 (A) |

TABLE 2-continued
| Compound | —NR₁R₂ | —Y—A—R₉ | R₆ | LC/MS characterization (conditions) |
|---|---|---|---|---|
| 15 | 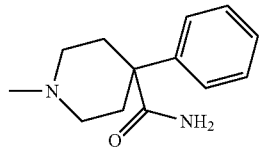 | —O—SO₂—(CH₂)₂—CF₃ | H | MH⁺ = 677<br>rt = 10.13<br>(A) |
| 16 | 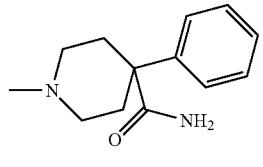 | —S—(CH₂)₃—CF₃ | Cl | MH⁺ = 677<br>rt = 11.25<br>(B) |
| 17 | 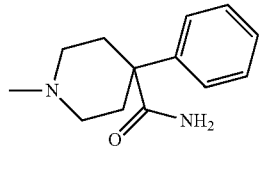 | —SO₂—(CH₂)₃—CF₃ | Cl | MH⁺ = 709<br>rt = 1.83<br>(C) |
| 18 | 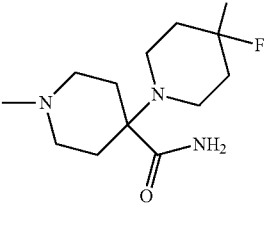 | —O—(CH₂)₃—OH | F | MH⁺ = 593<br>rt = 1.55<br>(C) |
| 19 | 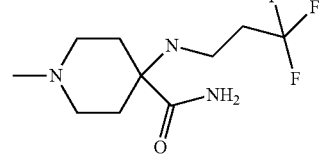 | —O—(CH₂)₃—OH | F | MH⁺ = 636<br>rt = 1.42<br>(C) |
| 20 | 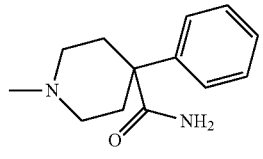 | —O—(CH₂)₃—OH | F | MH⁺ = 628<br>rt = 1.25<br>(C) |
| 21 |  | —O—(CH₂)₃—S—CH₃ | F | MH⁺ = 623<br>rt = 1.95<br>(C) |

TABLE 2-continued

| Compound | —NR$_1$R$_2$ | —Y—A—R$_9$ | R$_6$ | LC/MS characterization (conditions) |
|---|---|---|---|---|
| 22 | *N-methyl-4-phenylpiperidine-4-carboxamide* | —O—(CH$_2$)$_3$—SO$_2$—CH$_3$ | F | MH$^+$ = 655<br>rt = 1.56<br>(C) |
| 23 | *N-methyl-4-(4,4-difluoropiperidin-1-yl)piperidine-4-carboxamide* | —O—(CH$_2$)$_3$—S—CH$_3$ | F | MH$^+$ = 666<br>rt = 1.82<br>(C) |
| 24 | *N-methyl-4-(4,4-difluoropiperidin-1-yl)piperidine-4-carboxamide* | —O—(CH$_2$)$_3$—SO$_2$—CH$_3$ | F | MH$^+$ = 698<br>rt = 1.42<br>(C) |
| 25 | *N-methyl-4-phenylpiperidine-4-carboxamide* | —S—(CH$_2$)$_2$—NH$_2$ | Cl | MH$^+$ = 611<br>rt = 7.34<br>(A) |
| 26 | *N-methyl-4-phenylpiperidine-4-carboxamide* | —S—(CH$_2$)$_2$—NH—SO$_2$—CH$_3$ | Cl | MH$^+$ = 688<br>rt = 9.79<br>(A) |
| 27 | *N-methyl-4-phenylpiperidine-4-carboxamide* | —O—(CH$_2$)$_2$—OH | Cl | MH$^+$ = 595<br>rt = 9.26<br>(A) |

TABLE 2-continued

| Compound | —NR₁R₂ | —Y—A—R₉ | R₆ | LC/MS characterization (conditions) |
|---|---|---|---|---|
| 28 | N-methylpiperidine linked to 4,4-difluoropiperidine with CONH₂ | —O—(CH₂)₃—OH | Cl | MH⁺ = 652 rt = 1.53 (C) |
| 29 | N-methylpiperidine with CONH₂ and N-CH₂CF₃ | —O—(CH₂)₃—OH | Cl | MH⁺ = 630 rt = 1.6 (C) |
| 30 | N-methylpiperidine linked to 4,4-difluoropiperidine with CONH₂ | —O—(CH₂)₂—OH | Cl | MH⁺ = 638 rt = 1.45 (C) |
| 31 | N-methyl-4-phenylpiperidine-4-carboxamide | —O—SO₂—(CH₂)₂—CH₃ | Cl | MH⁺ = 657 rt = 10.62 (A) |
| 32 | N-methyl-4-phenylpiperidine-4-carboxamide | —SO₂—(CH₂)₃—OH | Cl | MH⁺ = 657 rt = 1.52 (C) |
| 33 | N-methyl-4-phenylpiperidine-4-carboxamide | —S—(CH₂)₃—OH | Cl | MH⁺ = 625 rt = 1.74 (B) |

TABLE 2-continued

| Compound | —NR$_1$R$_2$ | —Y—A—R$_9$ | R$_6$ | LC/MS characterization (conditions) |
|---|---|---|---|---|
| 34 | 1-methyl-4-phenylpiperidine-4-carboxamide | —O—(CH$_2$)$_2$—CO—NH$_2$ | H | MH$^+$ = 588 rt = 8.32 (A) |
| 35 | 1-methyl-4-phenylpiperidine-4-carboxamide | —O—(CH$_2$)$_3$—S—CH$_3$ | Cl | MH$^+$ = 639 rt = 11.43 (A) |
| 36 | 1-methyl-4-phenylpiperidine-4-carboxamide | —O—(CH$_2$)$_3$—SO$_2$—CH$_3$ | Cl | MH$^+$ = 671 rt = 9.64 (A) |
| 37 | 1-methyl-4-[(3,3,3-trifluoropropyl)amino]piperidine-4-carboxamide | —S—(CH$_2$)$_4$—OH | Cl | MH$^+$ = 674 rt = 9.62 (B) |
| 38 | 1-methyl-4-[(3,3,3-trifluoropropyl)amino]piperidine-4-carboxamide | —O—(CH$_2$)$_2$—OH | Cl | MH$^+$ = 629 rt = 8.71 (B) |
| 39 | 1-methyl-4-phenylpiperidine-4-carboxamide | —SO$_2$—(CH$_2$)$_3$—CH$_3$ | Cl | MH$^+$ = 655 rt = 1.84 (C) |

TABLE 2-continued

| Compound | —NR₁R₂ | —Y—A—R₉ | R₆ | LC/MS characterization (conditions) |
|---|---|---|---|---|
| 40 | 1-methylpiperidin-4-yl linked to 4,4-difluoropiperidinyl with carboxamide | —S—(CH$_2$)$_4$—OH | Cl | MH$^+$ = 682<br>rt = 1.64 |
| 41 | 1-methyl-3-phenylazetidine-3-carboxamide | —O—(CH$_2$)$_3$—OH | F | MH$^+$ = 565<br>rt = 1.52<br>(C) |
| 42 | 1-methylpiperidin-4-yl linked to 4,4-difluoropiperidinyl with carboxamide | —S—(CH$_2$)$_3$—OH | Cl | MH$^+$ = 668<br>rt = 1.63<br>(C) |
| 43 | 1-methyl-3-phenylazetidine-3-carboxamide | —O—(CH$_2$)$_2$—OH | Cl | MH$^+$ = 567<br>rt = 1.52<br>(C) |
| 44 | 1-methyl-3-phenylazetidine-3-carboxamide | —O—(CH$_2$)$_3$—OH | Cl | MH$^+$ = 581<br>rt = 1.68<br>(C) |
| 45 | 1-methyl-4-phenylpiperidine-4-carboxamide | —O—(CH$_2$)$_3$—OH | H | MH$^+$ = 575<br>rt = 1.49<br>(C) |

TABLE 2-continued

| Compound | —NR₁R₂ | —Y—A—R₉ | R₆ | LC/MS characterization (conditions) |
|---|---|---|---|---|
| 46 | 1-methylpiperidin-4-yl with 4-(4-fluorobenzyl)amino and 4-carboxamide substituents | —O—(CH$_2$)$_3$—OH | H | MH$^+$ = 622<br>rt = 1.20<br>(C) |
| 47 | 1-methylpiperidin-4-yl with 4-phenyl and 4-carboxamide substituents | —O—(CH$_2$)$_2$—OH | H | MH$^+$ = 561<br>rt = 1.43<br>(C) |
| 48 | 1-methylpiperidin-4-yl with 4-(4-fluorobenzyl)amino and 4-carboxamide substituents | —O—(CH$_2$)$_2$—OH | H | MH$^+$ = 608<br>rt = 1.15<br>(C) |

The analyses carried out by NMR for compounds 6, 8, 13, 27, 31 and 45 are given below:

Compound 6: $^1$H NMR: d$_6$-DMSO (250 MHz): δ (ppm): 1.67-1.90: m: 2H, 2.39-2.58: m: 2H, 3.13-3.38: m: 2H, 3.63: q: 2H, 3.91: t: 2H, 4.03-4.22: m: 2H, 4.81: t: 1H, 6.86: d: 2H, 7.00-7.12: m: 3H, 7.15-7.47: m: 9H, 7.68: d: 1H.

Compound 8: $^1$H NMR: d$_6$-DMSO (250 MHz): δ (ppm): 1.60-2.04: m: 4H, 2.37-2.62: m: 2H, 3.15-3.41: m: 2H, 3.48: q: 2H, 3.94: t: 2H, 4.02-4.21: m: 2H, 4.46: t: 1H, 6.80: d: 2H, 6.97-7.13: m: 3H, 7.14-7.25: m: 2H, 7.27-7.41: m: 4H, 7.44: s: 2H, 7.55: s: 1H, 7.68: s: 1H.

Compound 13: $^1$H NMR: d$_6$-DMSO (250 MHz): δ (ppm): 1.31-1.66: m: 4H, 1.76-1.97: m: 2H, 2.48-2.63: m: 2H, 3.19-3.50: m: 6H, 4.10-4.25: m: 2H, 4.42: t: 1H, 7.12: s: 1H, 7.20-7.60: m: 10H, 7.75: d: 2H, 7.82: d: 2H.

Compound 27: $^1$H NMR: d$_6$-DMSO (250 MHz): δ (ppm): 1.77-2.02: m: 2H, 2.46-2.62: m: 2H, 3.20-3.53: m: 2H, 3.68: q: 2H, 3.95: t: 2H, 4.10-4.25: m: 2H, 4.83: t: 1H, 6.85: d: 2H, 7.07-7.17: m: 3H, 7.22-7.30: m: 2H, 7.32-7.47: m: 4H, 7.49: d: 2H, 7.61: s: 1H, 7.73: t: 1H.

Compound 31: $^1$H NMR: d$_6$-DMSO (400 MHz): δ (ppm): 1.00: t: 3H; 1.71-1.85: m: 2H, 1.84-1.95: m: 2H, 2.53: d: 2H, 3.32-3.44: m: 2H, 3.47: t: 2H, 4.15: d: 2H, 7.09: s: 1H, 7.20-7.32: m: 6H, 7.34: t: 2H, 7.41: d: 2H, 7.48: dd: 1H, 7.52: d: 1H, 7.67: s: 1H, 7.73: d: 1H.

Compound 45: $^1$H NMR: d$_6$-DMSO (250 MHz): δ (ppm): 1.70-1.99: m: 4H, 2.45-2.63: m: 2H, 3.31: br s: 2H, 3.53: q: 2H, 3.98: t: 2H, 4.17: dt: 2H, 4.51: t: 1H, 6.82: d: 2H, 7.06-7.18: m: 3H, 7.20-7.65: m: 11H.

The compounds of formula (I) have a very good in vitro affinity (IC$_{50}$≦5×10$^{-7}$M) for CB$_1$ cannabinoid receptors under the experimental conditions described by M. Rinaldi-Carmona et al. (FEBS Letters, 1994, 350, 240-244).

The antagonist nature of the compounds of formula (I) was demonstrated in vitro by the results obtained in the models of the inhibition of adenylate cyclases as described in M. Bouaboula et al., J. Biol. Chem., 1995, 270, 13973-13980, M. Rinaldi-Carmona et al., J. Pharmacol. Exp. Ther., 1996, 278, 871-878, and M. Bouaboula et al., J. Biol. Chem., 1997, 272, 22330-22339.

The low penetration of the compounds of formula (I) at the haematoencephalic barrier (HEB) was evaluated in vivo by:

Measurement (1): the quantification of the compounds of formula (I) (unchanged) in mouse brain samples after intravenous (iv, 3 mg/kg) or oral administration, using the LC-MS/MS analytical technique.

The $$\frac{\text{amount present in the brain}}{\text{amount present in the plasma}}$$

ratio of less than 0.2 reflects a low penetration of the compound with regard to the brain.

Measurement (2): the measurement of the interaction of the compounds of formula (I) with the $CB_1$ receptors present in the brain of the mouse using an ex vivo [$^3$H]-CP55940 ($CB_1$ agonist) binding assay after intravenous administration (10 mg/kg), as described in M. Rinaldi-Carmona et al., FEBS Letters, 1994, 350, 240-244, M. Rinaldi-Carmona et al., Life Sciences, 1995, 56, 1941-1947, and M. Rinaldi-Carmona et al., J. Pharmacol. Exp. Ther., 2004, 310, 905-914. A percentage of inhibition of the binding of [$^3$H]-CP55940 with regard to the brain of less than 50% at 10 mg/kg reflects a low penetration with regard to the brain. Preferably, this percentage is less than 40% and more preferably less than 30%.

Measurement (3): the measurement of the blocking by the compounds of formula (I) of the hypothermic effect induced by an agonist of the $CB_1$ receptors (CP55940), after intravenous administration (10 mg/kg), as described in M. Rinaldi-Carmona et al., JPET, 2004, 310, 905-914.

A percentage of reversion of the hypothermic effect of CP55940 of less than or equal to 60% at 10 mg/kg reflects a low penetration with regard to the brain. Preferably, this percentage is less than 40% and more preferably less than 30%.

The interaction of a compound of formula (I) according to the invention with the $CB_1$ receptors present at the periphery was demonstrated in the mouse by the measurement of the blocking of the inhibitory effect induced by CP55940 on the gastrointestinal transit (GIT) after oral administration (po, 10 mg/kg), as described in M. Rinaldi-Carmona et al., J. Pharmacol. Exp. Ther., 2004, 310, 905-914.

A percentage of reversion of the hypothermic effect of CP55940 of greater than 50% at 10 mg/kg reflects a significant antagonist power with regard to the $CB_1$ receptors present at the periphery. Preferably, the percentage of reversion is between 70% and 100%.

By way of examples, the following measurements were carried out for compounds No. 8 and 45 of Table 3.

The compounds of formula (I) are compatible with a use as medicament.

Thus, according to another of its aspects, the subject-matter of the invention is medicaments for human or veterinary medicine which comprise a compound of formula (I) or an addition salt of the latter with a pharmaceutically acceptable acid or base of the compound of formula (I).

Thus, the compounds according to the invention can be used in man or animals (in particular in mammals, including, without limitation, dogs, cats, horses, cattle or sheep) in the treatment and/or prevention of diseases involving $CB_1$ cannabinoid receptors.

For example, without limitation, the compounds of formula (I) are of use as psychotropic medicaments, in particular in the treatment and/or prevention of psychiatric disorders, including anxiety, depression, mood disorders, insomnia, delusion disorders, obsessive disorders, psychoses in general, schizophrenia or attention deficit hyperactivity disorders (ADHD) in hyperkinetic children, and in the treatment and/or prevention of disorders related to the use of psychotropic substances, in particular in the case of abuse of a substance and/or of dependency on a substance, including alcohol dependence and nicotine dependence.

The compounds of formula (I) according to the invention can be used as medicaments in the treatment and/or prevention of migraine, stress, illnesses of psychosomatic origin, panic attacks, epilepsy, movement disorders, in particular dyskinesias or Parkinson's disease, trembling and dystonia.

The compounds of formula (I) according to the invention can also be used as medicaments in the treatment and/or prevention of memory disorders or cognitive disorders, in particular in the treatment and/or prevention of senile dementia or Alzheimer's disease, and in the treatment and/or prevention of disorders of attention or of vigilance.

Furthermore, the compounds of formula (I) can be of use as neuroprotectants, in the treatment of ischemia, brain trauma and the treatment and/or prevention of acute or chronic neurodegenerative diseases, including chorea, Huntington's chorea or Tourrette's syndrome.

The compounds of formula (I) according to the invention can be used as medicaments in the treatment and/or prevention of pain, including in particular neuropathic pain, acute peripheral pain, chronic pain of inflammatory origin or pain brought about by an anticancer treatment.

The compounds of formula (I) according to the invention can be used as medicaments in human or veterinary medicine

TABLE 3

| | Quantification of the compounds of formula (I) Ratio: amount present in the brain/amount present in the plasma [iv at 3 mg/kg, according to measurement (1)] | % of inhibition of the binding of [$^3$H]-CP55940 with regard to the $CB_1$ receptors present in the brain [iv at 10 mg/kg, according to measurement (2)] | % of reversion of the hypothermic effect of CP55940 with regard to the $CB_1$ receptors present in the brain [iv at 10 mg/kg, according to measurement (3)] | % of reversion of the inhibitory effect of CP55940 with regard to the $CB_1$ receptors present at the peripheryl (GIT) [po at 10 mg/kg] |
|---|---|---|---|---|
| Control: rimonabant | 1.8 | 100% | 100% [effective dose 50 ($DE_{50}$) = 0.3 mg/kg] | 100% |
| Compound No. 8 | 0.04 | 13% | 17.5% | 75.5% |
| Compound No. 45 | nd | 32% | 35.5% | 64.5% | in the treatment and/or prevention of disorders of metabolism, of appetite, of appetency (for sugars, carbohydrates, drugs, alcohol or any appetizing substance) and/or eating behaviour, in particular in the treatment and/or prevention of obesity or of bulimia, as well as in the treatment and/or prevention of diabetes, in particular type II diabetes or non-insulin-dependent diabetes, and in the treatment and/or prevention of dyslipidaemias or metabolic syndrome. Thus, the compounds of formula (I) according to the invention are of use in the treatment and/or prevention of obesity and of the risks associated with obesity, in particular the cardiovascular risks.

Furthermore, the compounds of formula (I) according to the invention can be used as medicaments in the treatment and/or prevention of gastrointestinal disorders, diarrhea, ulcers, vomiting, bladder and urinary disorders, liver diseases of alcoholic or nonalcoholic origin, such as chronic cirrhosis, fibrosis, hepatic steatosis or steatohepatitis, as well as disorders of endocrine origin, cardiovascular disorders, hypotension, atherosclerosis, haemorrhagic shock, septic shock, asthma, chronic bronchitis, chronic obstructive pulmonary disease, Raynaud syndrome, glaucoma, fertility disorders, premature labour, pregnancy interruption, inflammatory phenomena, diseases of the immune system, in particular autoimmune and neuroinflammatory diseases, such as rheumatoid arthritis, reactive arthritis, diseases which bring about demyelination, multiple sclerosis, infectious and viral diseases, such as encephalitis, or strokes and as medicaments for anticancer chemotherapy, in the treatment of Guillain-Barré syndrome and in the treatment and/or prevention of bone diseases and osteoporosis.

Furthermore, the compounds of formula (I) according to the invention can be used for their protective effects against cardiotoxicity induced by medicaments.

According to the present invention, the compounds of formula (I) are very particularly of use in the preparation of medicaments of use in the treatment and/or prevention of psychiatric disorders, in particular schizophrenia, disorders of attention and of vigilance, or attention deficit hyperactivity disorders (ADHD) in hyperkinetic children; in the treatment and/or prevention of memory deficits and cognitive disorders; of dependence on and withdrawal from a substance, in particular alcohol dependence, nicotine dependence, alcohol withdrawal and tobacco withdrawal; or of acute or chronic neurodegenerative diseases.

According to the present invention, the compounds of formula (I) are also very particularly of use in the preparation of medicaments of use in the treatment and/or prevention of disorders of appetite, disorders of appetency, metabolic disorders, obesity, type II diabetes, metabolic syndrome, dyslipidemia, gastrointestinal disorders, inflammatory phenomena, diseases of the immune system, psychotic disorders, alcohol dependence or nicotine dependence.

According to one of its aspects, the present invention relates to the use of a compound of formula (I) and of its pharmaceutically acceptable salts in the treatment and/or prevention of the disorders and diseases indicated above.

According to another of its aspects, the present invention relates to pharmaceutical compositions comprising, as active principle, a compound of formula (I) according to the invention. These pharmaceutical compositions comprise an effective dose of at least one compound according to the invention or one pharmaceutically acceptable salt of the said compound and at least one pharmaceutically acceptable excipient.

The said excipients are chosen, according to the pharmaceutical form and the method of administration desired, from the usual excipients which are known to a person skilled in the art.

The pharmaceutical compositions according to the present invention can comprise, in addition to a compound of formula (I), one (or more) other active principle(s) of use in the treatment and/or prevention of the disorders and diseases indicated above.

Thus, another subject-matter of the present invention is pharmaceutical compositions comprising a compound of formula (I) according to the present invention in combination with one (or more) active principle(s) chosen from one of the following therapeutic categories:

another antagonist or allosteric modulators of $CB_1$ cannabinoid receptors;
a modulator of $CR_2$ cannabinoid receptors;
an angiotensin II $AT_1$ receptor antagonist;
a converting enzyme inhibitor;
a calcium antagonist;
a diuretic;
a beta-blocker;
an antihyperlipidaemic or an antihypercholesterolaemic;
an antidiabetic;
another antiobesity agent or agent effective against metabolic disorders;
a nicotinic agonist or a partial nicotinic agonist;
an antidepressant, an antipsychotic or an anxiolytic;
an antineoplastic or an antiproliferative agent;
an opioid antagonist;
and:
an agent which improves the memory;
an agent of use in the treatment of alcoholism or symptoms of withdrawal;
an agent of use in the treatment of osteoporosis;
a nonsteroidal or steroidal anti-inflammatory;
an anti-infective;
an analgesic;
an antiasthmatic.

According to another aspect of the invention, the compound of formula (I), one of its pharmaceutically acceptable salts and the other associated active principle can be administered simultaneously, separately or spread out over time.

"Simultaneous use" is understood to mean the administration of the compounds of the composition according to the invention comprised within one and the same pharmaceutical form.

"Separate use" is understood to mean the administration, at the same time, of the two compounds of the composition according to the invention, each comprised within a separate pharmaceutical form.

"Use spread out over time" is understood to mean the successive administration of a first compound of the composition according to the invention, comprised within a pharmaceutical form, and then of a second compound of the composition according to the invention, comprised within a separate pharmaceutical form. In this case, the period of time elapsed between the administration of the first compound of the composition according to the invention and the administration of the second compound of the same composition according to the invention generally does not exceed 24 hours.

In the pharmaceutical compositions of the present invention for oral, sublingual, subcutaneous, intramuscular, intravenous, topical, local, intratracheal, intranasal, transdermal or rectal administration, the active principle of formula (I) above or its optional salt can be administered in unit administration form, as a mixture with conventional pharmaceutical excipients, to animals and to human beings for the prophylaxis, treatment and/or prevention of the above disorders or diseases.

The appropriate unit administration forms comprise oral forms, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. For the topical application, the compounds according to the invention can be used in creams, gels, ointments or lotions.

By way of example, a unit administration form of a compound according to the invention in tablet form can comprise the following components:

Compound according to the invention: 50.0 mg
Mannitol: 223.75 mg
Croscarmellose sodium: 6.0 mg
Maize starch: 15.0 mg
Hydroxypropylmethylcellulose: 2.25 mg
Magnesium stearate: 3.0 mg Orally, the dose of active principle administered per day can reach 0.01 to 100 mg/kg, taken all at once or spread over the day, preferably 0.02 to 50 mg/kg.

There may be specific cases where higher or lower dosages are appropriate; such dosages do not depart from the scope of the invention. According to the usual practice, the dosage appropriate to each patient is determined by the doctor according to the method of administration and the weight and the response of the said patient.

The present invention, according to another of its aspects, also relates to a method for the treatment and/or prevention of the pathologies indicated above which comprises the administration, to a patient, of an effective dose of a compound according to the invention or one of its pharmaceutically acceptable salts.

The invention claimed is:
1. Compound of formula (I):

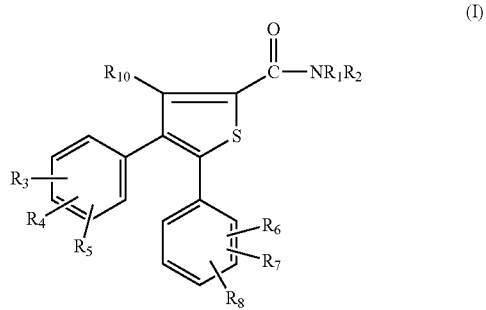

in which:
$R_1$ and $R_2$, together with the nitrogen atom to which they are bonded, form:
a saturated heterocyclic radical of 4 to 7 atoms comprising a nitrogen atom which is unsubstituted or substituted once or twice by a substituent each independently chosen from:
a cyano, —$COR_{11}$, —$CH_2NHR_{12}$, —$(C_3-C_7)$cycloalkyl, —$CH_2COR_{11}$, —$NR_{12}R_{13}$, —$NHCOR_{14}$, —$SO_2R_{14}$ and/or —$SO_2NR_{12}R_{13}$ group;
and/or a phenyl, benzyl or pyridinyl group; the said groups being unsubstituted or substituted one or more times by a substituent each independently chosen from a halogen atom or a $(C_1-C_4)$alkyl, trifluoromethyl, hydroxyl, $(C_1-C_4)$alkoxy and/or cyano group;
and/or a piperidin-1-yl, pyrrolidin-1-yl or azetidin-1-yl group, the said groups being unsubstituted or substituted one or more times by a substituent each independently chosen from a fluorine atom or a $(C_1-C_4)$alkyl, $(C_1-C_4)$alkoxy, hydroxyl, trifluoromethyl and/or $OCF_3$ group;
and/or a phenylamino or benzylamino group, the said groups being unsubstituted or substituted one or more times by a substituent each independently chosen from a halogen atom or a $(C_1-C_4)$alkyl, trifluoromethyl, hydroxyl, $(C_1-C_4)$alkoxy and/or cyano group;
$R_3$, $R_4$, $R_5$, $R_6$, $R_7$ and $R_8$ each independently represent a hydrogen atom, a halogen atom, a —CN, —$S(O)_nR_{14}$, —$OSO_2R_{14}$ or $(C_1-C_6)$alkyl group and/or a $(C_1-C_6)$alkoxy group, the said groups being unsubstituted or substituted one or more times by a fluorine atom, provided that one of the two substituents $R_3$ and $R_6$ represents a Y-A-$R_9$ group;
Y represents an oxygen atom;
A represents a $(C_1-C_4)$alkylene group which is unsubstituted or substituted one or more times by a substituent each independently chosen from a $(C_1-C_3)$alkyl group and/or by a fluorine atom;
$R_9$ represents an —$OR_{19}$, —CN, —$CH_3$, —$CF_3$, —$NR_{19}R_{20}$, —$CO_2R_{19}$, —$CONR_{19}R_{20}$, —$NR_{15}COR_{19}$, —$CONHNH_2$, —$CONHOH$, —$CONHSO_2R_{21}$, —$S(O)_nR_{21}$, —$SO_2NR_{19}R_{20}$, —$NR_{18}SO_2R_{21}$ or —$NR_{15}SO_2NR_{19}R_{20}$ group;
$R_{10}$ represents a hydrogen atom or a $(C_1-C_4)$alkyl group and preferably a hydrogen atom;
$R_{11}$ represents:
a $(C_1-C_4)$alkyl, phenyl, benzyl, $(C_1-C_4)$alkoxy or $(C_1-C_3)$alkylene-O—$(C_1-C_3)$alkyl group, the said groups being unsubstituted or substituted by a substituent each independently chosen from a $(C_1-C_4)$alkoxy group and/or a hydroxyl group and/or by one or more fluorine atoms;
and/or an —$NR_{16}R_{17}$ group;
$R_{12}$ and $R_{13}$ each independently represent a hydrogen atom or a $(C_1-C_6)$alkyl group optionally substituted one or more times by a substituent each independently chosen from a fluorine atom, an —OH group and/or an —$OR_{14}$ group;
or $R_{12}$ and $R_{13}$, together with the nitrogen atom to which they are bonded, form a 4- to 7-membered heterocyclic radical which can comprise a second heteroatom chosen from a nitrogen, oxygen or sulphur atom;
n represents 0, 1 or 2;
n' represents 0, 1 or 2;
$R_{14}$ represents a $(C_1-C_4)$alkyl group which is unsubstituted or substituted one or more times by a fluorine atom;
$R_{15}$ represents a hydrogen atom or a $(C_1-C_4)$alkyl group;
$R_{16}$ and $R_{17}$ each independently represent:
a hydrogen atom;
and/or a benzyl group which is unsubstituted or substituted one or more times by a substituent each independently chosen from a halogen atom or a $(C_1-C_4)$alkyl, trifluoromethyl, hydroxyl, $(C_1-C_4)$alkoxy and/or cyano group;
and/or a $(C_1-C_6)$alkyl group optionally substituted one or more times by a substituent each independently chosen from a halogen atom or an —OH and/or an —$OR_{14}$ group;

$R_{18}$ represents a hydrogen atom or a $(C_1-C_4)$alkyl group which is unsubstituted or substituted one or more times by a fluorine atom;

$R_{19}$ and $R_{20}$ each independently represent a hydrogen atom or a $(C_1-C_6)$alkyl group optionally substituted one or more times by a substituent each independently chosen from a fluorine atom, an —OH group and/or an —$OR_{14}$ group;

or $R_{19}$ and $R_{20}$, together with the nitrogen atom to which they are bonded, form a 4- to 7-membered heterocyclic radical which can comprise a second heteroatom chosen from a nitrogen, oxygen or sulphur atom;

$R_{21}$ represents a $(C_1-C_4)$alkyl group which is unsubstituted or substituted one or more times by a fluorine atom;

or its salt.

2. Compound according to any one of claim 1, in which:
$R_3$ represents a Y-A-$R_9$ group;
$R_6$ represents a hydrogen atom, a halogen atom, a —CN, —$S(O)_nR_{14}$ or —$OSO_2R_{14}$ group, a $(C_1-C_6)$alkyl group or a $(C_1-C_6)$alkoxy group, the said groups being unsubstituted or substituted one or more times by a fluorine atom;
and the other substituents are as defined for the compounds of formula (I);
or its salt.

3. Compound according to any one of claim 1, in which:
$R_6$ represents a Y-A-$R_9$ group,
$R_3$ represents a hydrogen atom, a halogen atom, a —CN, —$S(O)_nR_{14}$ or —$OSO_2R_{14}$ group, a $(C_1-C_6)$alkyl group or a $(C_1-C_6)$alkoxy group, the said groups being unsubstituted or substituted one or more times by a fluorine atom;
and the other substituents are as defined for the compounds of formula (I);
or its salt.

4. Compound according to claim 1, in which:
$R_3$ represents a Y-A-$R_9$ group;
$R_4$, $R_5$, $R_6$, $R_7$ and $R_8$ each independently represent a hydrogen atom, a halogen atom, a —CN group and/or a $(C_1-C_6)$alkyl group, the said group being unsubstituted or substituted one or more times by a fluorine atom;
and the other substituents are as defined for the compounds of formula (I);
or its salt.

5. Compound according to claim 1, in which:
$R_6$ represents a Y-A-$R_9$ group;
$R_3$, $R_4$, $R_5$, $R_7$ and $R_8$ each independently represent a hydrogen atom, a halogen atom, a —CN group and/or a $(C_1-C_6)$alkyl group, the said group being unsubstituted or substituted one or more times by a fluorine atom;
and the other substituents are as defined for the compounds of formula (I);
or its salt.

6. Compound of formula (I) according to claim 1, in which:
A represents an unsubstituted $(C_1-C_4)$alkylene group;
and the other substituents are as defined for the compounds of formula (I);
or its salt.

7. Compound of formula (I) according to claim 1, in which:
$R_9$ represents an —$OR_{19}$, —$CH_3$, —$CF_3$, —$NR_{19}R_{20}$, —$CONR_{19}R_{20}$, —$NR_{15}COR_{19}$, —$S(O)_nR_{21}$ or —$NR_{18}SO_2R_{21}$ group;
and the other substituents are as defined for the compounds of formula (I);
or its salt.

8. Compound of formula (I) according to claim 1, in which:
Y represents an oxygen atom or a sulphur atom;
and the other substituents are as defined for the compounds of formula (I);
or its salt.

9. Compound of formula (I) according to claim 1, in which:
$R_1$ and $R_2$, together with the nitrogen atom to which they are bonded, form a homopiperidin-1-yl, piperidin-1-yl, pyrrolidin-1-yl or azetidin-1-yl radical, the said radical being substituted once or twice by a substituent each independently chosen from:
a cyano, —$COR_{11}$, —$NR_{12}R_{13}$, —$NHCOR_{14}$, —$CH_2COR_{11}$, —$SO_2R_{14}$ and/or —$SO_2NR_{12}R_{13}$ group;
and/or a phenyl, benzyl or pyridinyl group; the said groups being unsubstituted or substituted one or more times by a substituent each independently chosen from a halogen atom or a $(C_1-C_4)$alkyl, trifluoromethyl, hydroxyl, $(C_1-C_4)$alkoxy and/or cyano group;
and/or a piperidin-1-yl, pyrrolidin-1-yl or azetidin-1-yl group, the said groups being unsubstituted or substituted one or more times by a substituent each independently chosen from a fluorine atom or a $(C_1-C_4)$alkyl, $(C_1-C_4)$alkoxy, hydroxyl, trifluoromethyl and/or $OCF_3$ group;
and/or a phenylamino or benzylamino group, the said groups being unsubstituted or substituted one or more times by a substituent each independently chosen from a halogen atom or a $(C_1-C_4)$alkyl, trifluoromethyl, hydroxyl, $(C_1-C_4)$alkoxy and/or cyano group;
and/or an amino$(C_1-C_6)$alkyl group which is unsubstituted or substituted one or more times by a substituent each independently chosen from a halogen atom or a hydroxyl, $(C_1-C_4)$alkoxy and/or cyano group;
and/or an amino$(C_3-C_7)$cycloalkyl group which is unsubstituted or substituted one or more times by a substituent each independently chosen from a halogen atom or a hydroxyl, $(C_1-C_4)$alkyl, $(C_1-C_4)$alkoxy and/or cyano group, the said $(C_1-C_4)$alkyl group being unsubstituted or substituted one or more times by a fluorine atom;
and the other substituents are as defined for the compounds of formula (I);
or its salt.

10. Compound of formula (I) according to claim 9, in which:
$R_1$ and $R_2$, together with the nitrogen atom to which they are bonded, form a homopiperidin-1-yl, piperidin-1-yl, pyrrolidin-1-yl or azetidin-1-yl radical, the said radical being gem-disubstituted:
the first substituent being chosen from a cyano, —$COR_{11}$, —$NHCOR_{14}$ or —$SO_2R_{14}$ group;
the second substituent being chosen from:
$NR_{12}R_{13}$;
and/or a phenyl group, the said group being unsubstituted or substituted one or more times by a substituent each independently chosen from a halogen atom or a $(C_1-C_4)$alkyl, trifluoromethyl, hydroxyl, $(C_1-C_4)$alkoxy and/or cyano group;
and/or a piperidin-1-yl group, the said group being unsubstituted or substituted one or more times by a substituent each independently chosen from a fluorine atom or a $(C_1-C_4)$alkyl, $(C_1-C_4)$alkoxy, hydroxyl, trifluoromethyl and/or $OCF_3$ group;
and/or a benzylamino group, the said group being unsubstituted or substituted one or more times by a substituent each independently chosen from a halogen atom or a $(C_1-C_4)$alkyl, trifluoromethyl, hydroxyl, $(C_1-C_4)$alkoxy and/or cyano group;

and the other substituents are as defined for the compounds of formula (I);

or its salt.

11. Compound of formula (I) according to claim 10, in which:
- $R_1$ and $R_2$, together with the nitrogen atom to which they are bonded, form a piperidin-1-yl or azetidin-1-yl radical, the said radical being gem-disubstituted:
- the first substituent being —$COR_{11}$;
- and the second substituent being chosen from —$NR_{12}R_{13}$, a phenyl group, a benzylamino group or a piperidin-1-yl group, the said piperidin-1-yl group being unsubstituted or substituted one or more times by a substituent each independently chosen from a fluorine atom or a ($C_1$-$C_4$) alkyl, ($C_1$-$C_4$)alkoxy, hydroxyl, trifluoromethyl and/or $OCF_3$ group;
- and the other substituents are as defined for the compounds of formula (I);

or its salt.

12. Pharmaceutical composition, characterized in that it comprises a compound of formula (I) according to claim 1 or an addition salt of this compound of formula (I) with a pharmaceutically acceptable acid and at least one pharmaceutically acceptable excipient.

\* \* \* \* \*

UNITED STATES PATENT AND TRADEMARK OFFICE
CERTIFICATE OF CORRECTION

PATENT NO.       : 8,410,137 B2                                                    Page 1 of 1
APPLICATION NO.  : 13/057043
DATED            : April 2, 2013
INVENTOR(S)      : Barth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 40 days.

Signed and Sealed this
First Day of September, 2015

Michelle K. Lee
*Director of the United States Patent and Trademark Office*